US012699097B2

(12) United States Patent
Santockyte et al.

(10) Patent No.: US 12,699,097 B2
(45) Date of Patent: Aug. 4, 2026

(54) M-PROTEIN ASSAYS

(71) Applicant: Bristol-Myers Squibb Company, Princeton, NJ (US)

(72) Inventors: Rasa Santockyte, Princeton, NJ (US); Jianing Zeng, Princeton, NJ (US); Oscar Puig, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1044 days.

(21) Appl. No.: 17/774,818

(22) PCT Filed: Nov. 4, 2020

(86) PCT No.: PCT/US2020/058927
§ 371 (c)(1),
(2) Date: May 5, 2022

(87) PCT Pub. No.: WO2021/092044
PCT Pub. Date: May 14, 2021

(65) Prior Publication Data
US 2022/0390455 A1 Dec. 8, 2022

Related U.S. Application Data

(60) Provisional application No. 62/931,063, filed on Nov. 5, 2019.

(51) Int. Cl.

| | |
|---|---|
| G01N 33/575 | (2026.01) |
| A61K 31/138 | (2006.01) |
| A61K 31/167 | (2006.01) |
| A61K 31/341 | (2006.01) |
| A61K 31/454 | (2006.01) |
| A61K 31/573 | (2006.01) |
| A61P 35/00 | (2006.01) |
| C07K 16/28 | (2006.01) |
| G01N 33/68 | (2006.01) |

(52) U.S. Cl.
CPC ....... *G01N 33/5758* (2026.01); *A61K 31/138* (2013.01); *A61K 31/167* (2013.01); *A61K 31/341* (2013.01); *A61K 31/454* (2013.01); *A61K 31/573* (2013.01); *A61P 35/00* (2018.01); *C07K 16/2803* (2013.01); *G01N 33/6851* (2013.01); *G01N 33/6854* (2013.01); *C07K 2317/24* (2013.01)

(58) Field of Classification Search
CPC ......... G01N 33/57484; G01N 33/6851; G01N 33/6854; G01N 2800/7028; G01N 33/6848; G01N 2030/027; A61P 35/00; A61P 35/02; C07K 16/2803
See application file for complete search history.

(56) References Cited

U.S. PATENT DOCUMENTS

| | | | |
|---|---|---|---|
| 6,808,710 B1 | 10/2004 | Wood et al. | |
| 7,488,802 B2 | 2/2009 | Collins et al. | |
| 8,008,449 B2 | 8/2011 | Korman et al. | |
| 8,168,757 B2 | 5/2012 | Finnefrock et al. | |
| 8,354,509 B2 | 1/2013 | Carven et al. | |
| 2005/0025763 A1 | 2/2005 | Williams et al. | |
| 2006/0024296 A1 | 2/2006 | Williams et al. | |
| 2008/0095768 A1 | 4/2008 | Afar et al. | |
| 2008/0124332 A1 | 5/2008 | Afar | |
| 2008/0152646 A1 | 6/2008 | Anderson et al. | |
| 2009/0238827 A1 | 9/2009 | Williams et al. | |
| 2009/0238835 A1 | 9/2009 | Williams et al. | |
| 2009/0246852 A1 | 10/2009 | Williams et al. | |
| 2010/0168397 A1 | 7/2010 | Williams et al. | |
| 2011/0165154 A1 | 7/2011 | Afar | |
| 2011/0206701 A1 | 8/2011 | Afar et al. | |
| 2012/0064067 A1 | 3/2012 | Williams et al. | |
| 2012/0064068 A1 | 3/2012 | Williams et al. | |
| 2012/0064069 A1 | 3/2012 | Williams et al. | |
| 2012/0064083 A1 | 3/2012 | Williams et al. | |
| 2012/0070440 A1 | 3/2012 | Williams et al. | |
| 2012/0148576 A1* | 6/2012 | Sharma ............ | A61K 39/39591 424/133.1 |
| 2013/0052158 A1 | 2/2013 | Van Rhee | |
| 2013/0058921 A1 | 3/2013 | Van Rhee | |
| 2014/0065063 A1 | 3/2014 | Williams et al. | |
| 2014/0322201 A1 | 10/2014 | Afar et al. | |
| 2015/0079109 A1 | 3/2015 | Li et al. | |

(Continued)

FOREIGN PATENT DOCUMENTS

| | | |
|---|---|---|
| WO | WO-2004100898 A2 | 11/2004 |
| WO | WO-2005102387 A2 | 11/2005 |

(Continued)

OTHER PUBLICATIONS

Mills et al. Detecting monoclonal immunoglobulins in human serum using mass spectrometry, Methods, 81, 56-65, 2015. (Year: 2015).*
Sekine et al. Upfront treatment for newly diagnosed transplant-ineligible multiple myeloma patients: A systematic review and network meta-analysis of 14,533 patients over 29 randomized clinical trials. Critical Reviews in Oncology/Hematology, 143, 102-116, 2019. (Year: 2019).*
Shao et al.—Evolving data on CAR T-cell therapy for multiple myeloma, novel targets, conditioning regimens and novel constructs: a systematic review. Blood 134 (Supplement 1) : 5547 2019. (Year: 2019).*

(Continued)

*Primary Examiner* — Elly-Gerald Stoica
(74) *Attorney, Agent, or Firm* — Sterne, Kessler, Goldstein & Fox P.L.L.C.

(57) ABSTRACT

The disclosure provides methods for measuring M-proteins in a biological sample obtained from a subject, comprising applying purified immunoglobulins to a liquid chromatography (LC) mass spectrometry (MS). In some aspects, the immunoglobulins are purified using an immunocapture (IC). In certain aspects, the subject has a plasma cell disorder, e.g., multiple myeloma.

11 Claims, 22 Drawing Sheets

(56) References Cited

U.S. PATENT DOCUMENTS

| | | | |
|---|---|---|---|
| 2015/0210769 A1* | 7/2015 | Freeman | A61P 1/04 |
| | | | 435/254.2 |
| 2016/0002335 A1 | 1/2016 | Williams et al. | |
| 2016/0137735 A1 | 5/2016 | Afar et al. | |
| 2016/0206734 A1 | 7/2016 | Afar | |
| 2016/0264670 A1 | 9/2016 | Graziano et al. | |
| 2016/0272708 A1 | 9/2016 | Chen | |
| 2017/0121409 A1* | 5/2017 | Verona | C07K 16/1063 |
| 2017/0281624 A1* | 10/2017 | Peters | A61K 31/55 |
| 2017/0340733 A1* | 11/2017 | Cao | A61K 38/13 |
| 2017/0342150 A1 | 11/2017 | Afar | |
| 2018/0222982 A1* | 8/2018 | Dranoff | C07K 16/2818 |
| 2018/0371093 A1* | 12/2018 | Bilic | A61K 45/06 |
| 2019/0100588 A1* | 4/2019 | Chaganty | A61P 35/00 |

FOREIGN PATENT DOCUMENTS

| | | |
|---|---|---|
| WO | WO-2008019376 A2 | 2/2008 |
| WO | WO-2008019378 A1 | 2/2008 |
| WO | WO-2008019379 A2 | 2/2008 |
| WO | WO-2008156712 A1 | 12/2008 |
| WO | WO-2010051391 A1 | 5/2010 |
| WO | WO-2011053321 A1 | 5/2011 |
| WO | WO-2011053322 A1 | 5/2011 |
| WO | WO-2012145493 A1 | 10/2012 |
| WO | WO-2014179664 A2 | 11/2014 |
| WO | WO-2014194302 A2 | 12/2014 |
| WO | WO-2014206107 A1 | 12/2014 |
| WO | WO-201535606 A1 | 3/2015 |
| WO | WO-2015085847 A1 | 6/2015 |
| WO | WO-2015112800 A1 | 7/2015 |
| WO | WO-2015112900 A1 | 7/2015 |
| WO | WO-2016106159 A1 | 6/2016 |
| WO | WO-2016197367 A1 | 12/2016 |
| WO | WO-201719846 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017040790 A1 | 3/2017 |
| WO | WO-2017106061 A1 | 6/2017 |
| WO | WO-2017123557 A1 | 7/2017 |
| WO | WO-2017132825 A1 | 8/2017 |
| WO | WO-2017132827 A1 | 8/2017 |
| WO | WO-2017133540 A1 | 8/2017 |

OTHER PUBLICATIONS

International Search Report and Written Opinion for International Application No. PCT/US2020/058927, European Patent Office, Netherlands, mailed on Feb. 22, 2021, 11 pages.

Jakubowiak, A.J., et al., "Phase I trial of anti-CS1 monoclonal antibody elotuzumab in combination with bortezomib in the treatment of relapsed/refractory multiple myeloma," J Clin Oncol 30(16):1960-1965, American Society of Clinical Oncology, United States (Jun. 2012).

Jian, W., et al., "A workflow for absolute quantitation of large therapeutic proteins in biological samples at intact level using LC-HRMS," Bioanalysis 8(16):1679-1691, Future Science, United Kingdom (Aug. 2016).

Kaplon, H., and Reichert, J., "Antibodies to watch in 2018," mAbs 10(2):183-203, Taylor & Francis, United Kingdom (Feb. 2018).

Liu, S.Y., and Wu, Y.L., "Ongoing clinical trials of PD-1 and PD-L1 inhibitors for lung cancer in China," J Hematol Oncol 10(1):136, Springer Nature, Germany (Jul. 2017).

Lonial, S., et al., "Elotuzumab in combination with lenalidomide and low-dose dexamethasone in relapsed or refractory multiple myeloma," J Clin Oncol 30(16):1953-1959, American Society of Clinical Oncology, United States (Jun. 2012).

Lonial, S., et al., "Phase (Ph) I/II study of elotuzumab (Elo) plus lenalidomide/dexamethasone (Len/dex) in relapsed/refractory multiple myeloma (RR MM): Updated Ph II results and Ph I/II long-term safety," J Clin Oncol (ASCO Annual Meeting I) 31(15): Abstract 8542, United States (May 2013) Accessed at http://www.ascopubs.org/doi/abs/10.1200/jco.2013.31.15_suppl.8542 on Feb. 1, 2023.

Mills, J.R., et al., "A universal solution for eliminating false positives in myeloma due to therapeutic monoclonal antibody interference," Blood 132(6):670-672, Elsevier, Netherlands (Aug. 2018).

Mills, J.R., et al., "High sensitivity blood-based M-protein detection in sCR patients with multiple myeloma," Blood Cancer J 7(8):e590, Springer Nature, Germany (Aug. 2017).

Richardson, P.G., et al., "Elotuzumab in Combination with Lenalidomide and Dexamethasone in Patients with Relapsed Multiple Myeloma: Interim Results of a Phase 2 Study," Blood 116(21):986, American Society of Hematology, United States (Nov. 2010).

Santockyte, R., et al., "High Sensitivity, Interference-Free Assay for Detection of M-Protein in Multiple Myeloma Minimal Residual Disease," Bioanalytical Sciences, pp. 1-26, Bristol-Myers Squibb, United States (Oct. 2019).

Santockyte, R., et al., "High-Throughput Therapeutic Antibody Interference-Free High-Resolution Mass Spectrometry Assay for Monitoring M-Proteins in Multiple Myeloma," Anal Chem 93(2):834-842, American Chemical Society, United States (Jan. 2021).

Santockyte, R., and Puig, O., "M protein Mass Spectrometry for Measurable Residual Disease (MRD) in multiple myeloma," BMS Internal Use Presentation, pp. 1-13, Bristol-Myers Squibb, United States (Oct. 2019).

Tai, Y.T., et al., "Anti-CS1 humanized monoclonal antibody HuLuc63 inhibits myeloma cell adhesion and induces antibody-dependent cellular cytotoxicity in the bone marrow milieu," Blood 112(4):1329-1337, American Society of Hematology, United States (Aug. 2008).

Trudel, S., et al., "Update on elotuzumab for the treatment of relapsed/refractory multiple myeloma: patients' selection and perspective," Onco Targets Ther 12:5813-5822, Dove Medical Press, United Kingdom (Jul. 2019).

Uniprotkb, "SLAM family member 7," Accession No. Q9NQ25, accessed at https://uniprot.org/uniprotkb/Q9NQ25/entry#names_and_taxonomy, accessed on Feb. 2, 2020, 1 page.

Van Rhee, F., et al., "Combinatorial efficacy of anti-CS1 monoclonal antibody elotuzumab (HuLuc63) and bortezomib against multiple myeloma," Mol Cancer Ther 8(9):2616-2624, American Association for Cancer Research, United States (Sep. 2009).

Zonder, J.A., et al., "A phase 1, multicenter, open-label, dose escalation study of elotuzumab in patients with advanced multiple myeloma," Blood 120(3):552-559, American Society of Hematology, United States (Jul. 2012).

Iida, S., "Multiple myeloma: from diagnosis to the up-to-date treatment," Journal of the Japanese Society of Internal Medicine 105(7):1199-1201, Japanese Society of Internal Medicine Secretariat, Japan (Jul. 2016).

Ishida, T., "Topics: II. The Diagnosis of Multiple Myeloma," Journal of the Japanese Society of Internal Medicine 105(7):1209-1215, Japanese Society of Internal Medicine Secretariat, Japan (Jul. 2016).

Morishita, K., "Combination of elotuzumab, lenalidomide, and low-dose dexamethasone for advanced multiple myeloma has a 92% response rate [EHA2012]," medical.nikkeibp.co.jp, accessed at https://medical.nikkeibp.co.jp/leaf/all/gakkai/sp/eha2012/201206/525491.html, published Jun. 19, 2012, 3 pages.

Agency for Healthcare Research and Quality, "Evidence-based Practice Center Systematic Review Protocol Project Title: Serum-Free Light Chain Analysis for the Diagnosis, Management, and Prognosis of Plasma Cell Dyscrasias," Effective Health Care Program, accessed at https://effectivehealthcare.ahrq.gov/sites/default/files/pdf/plasma-cell-dyscrasias-sflc-assay_research-protocol.pdf, dated May 2, 2011, 14 pages.

Ailawadhi, S., et al., "A Phase I Study to Assess the Safety and Pharmacokinetics of Single-agent Lorvotuzumab Mertansine (IMGN901) in Patients with Relapsed and/or Refractory CD-56-positive Multiple Myeloma," Clin Lymphoma Myeloma Leuk 19(1):29-34, Elsevier, Netherlands (Jan. 2019).

(56)  References Cited

OTHER PUBLICATIONS

Atanackovic, D., et al., "Surface molecule CD229 as a novel target for the diagnosis and treatment of multiple myeloma," Haematologica 96(10):1512-1520, Ferrata-Storti Foundation, Italy (Oct. 2011).

Bristol-Myers Squibb, "EMPLICITI® (elotuzumab)," accessed at https://packageinserts.bms.com/pi/pi_empliciti.pdf, dated Oct. 13, 2019, 11 pages.

Brudno, J.N., et al., "T Cells Genetically Modified to Express an Anti-B-Cell Maturation Antigen Chimeric Antigen Receptor Cause Remissions of Poor-Prognosis Relapsed Multiple Myeloma," J Clin Oncol 36(22):2267-2280, American Society of Clinical Oncology, United States (Aug. 2018).

Costa, F., et al., "Checkpoint Inhibition in Myeloma: Opportunities and Challenges," Front Immunol 9:2204, Frontiers Media SA, Switzerland (Sep. 2018).

De Weerdt, O., et al., "Continuous low-dose cyclophosphamide-prednisone is effective and well tolerated in patients with advanced multiple myeloma," Neth J Med 59(2):50-56, Elsevier, Netherlands (Aug. 2001).

Fernández De Larrea, C., et al., "Plasma cell leukemia: consensus statement on diagnostic requirements, response criteria and treatment recommendations by the International Myeloma Working Group," Leukemia 27(4):780-791, Springer Nature, Germany (Apr. 2013).

Gebski, C., et al. "Affinity Chromatography Applications with Single-Domain Antibodies," BioProcess International, accessed at https://www.bioprocessintl.com/chromatography/affinity-chromatography-applications-with-single-domain-antibodies?utm_source=chatgpt.com, dated Aug. 1, 2013, 4 pages.

Görgün, G., et al., "Lenalidomide Enhances Immune Checkpoint Blockade-Induced Immune Response in Multiple Myeloma," Clin Cancer Res 21(20):4607-4618, American Association for Cancer Research, United States (Oct. 2015).

Jelinek, T., et al., "Update on PD-1/PD-L1 Inhibitors in Multiple Myeloma," Front Immunol 9:2431, Frontiers Media SA, Switzerland (Nov. 2018).

Kumar, S., et al., "International Myeloma Working Group consensus criteria for response and minimal residual disease assessment in multiple myeloma," Lancet Oncol 17(8):e328-e346, Elsevier, Netherlands (Aug. 2016).

Lakshman, A., et al., "Efficacy of VDT PACE-like regimens in treatment of relapsed/refractory multiple myeloma," Am J Hematol 93(2):179-186, Wiley, United States (Feb. 2018).

Lonial, S., et al., "Elotuzumab Therapy for Relapsed or Refractory Multiple Myeloma," N Engl J Med 373(7):621-631, Massachusetts Medical Society, United States (Aug. 2015).

Mills, J.R., et al., "Comprehensive Assessment of M-Proteins Using Nanobody Enrichment Coupled to MALDI-TOF Mass Spectrometry," Clin Chem 62(10):1334-1344, Oxford University Press, United Kingdom (Oct. 2016).

NCT02462525, "Dose-Escalation Study of ABBV-838, an Antibody Drug Conjugate, in Subjects With Relapsed and Refractory Multiple Myeloma," ClinicalTrials.gov, accessed at https://clinicaltrials.gov/study/NCT02462525, Last Update Posted Sep. 13, 2018, 13 pages.

Oliva, S., et al., "Promises and Pitfalls in the Use of PD-1/PD-L1 Inhibitors in Multiple Myeloma," Front Immunol 9:2749, Frontiers Media SA, Switzerland (Nov. 2018).

Segeren, C.M., et al., "Vincristine, doxorubicin and dexamethasone (VAD) administered as rapid intravenous infusion for first-line treatment in untreated multiple myeloma," Br J Haematol 105(1):127-130, Blackwell Science Ltd, United Kingdom (Apr. 1999).

* cited by examiner

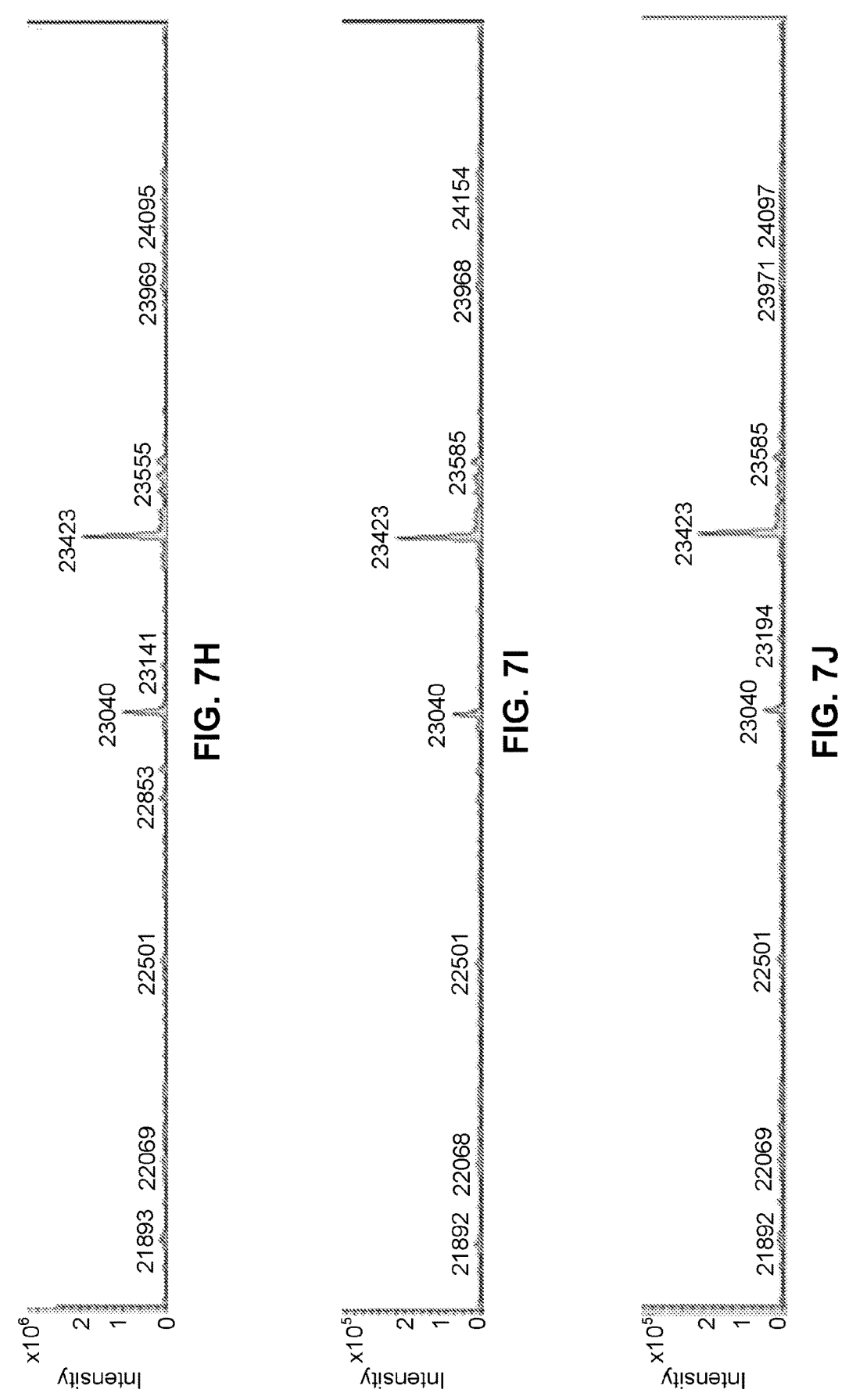

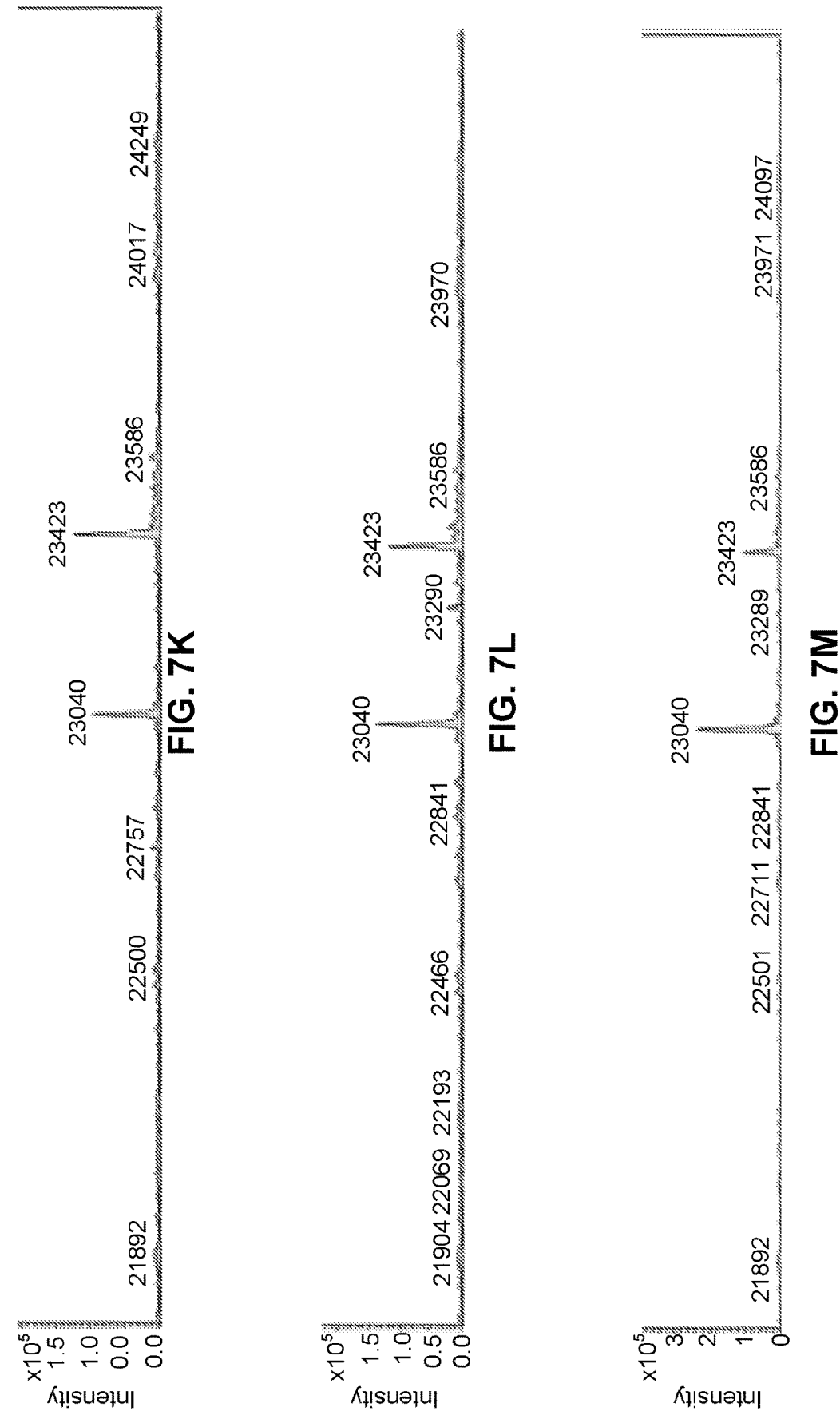

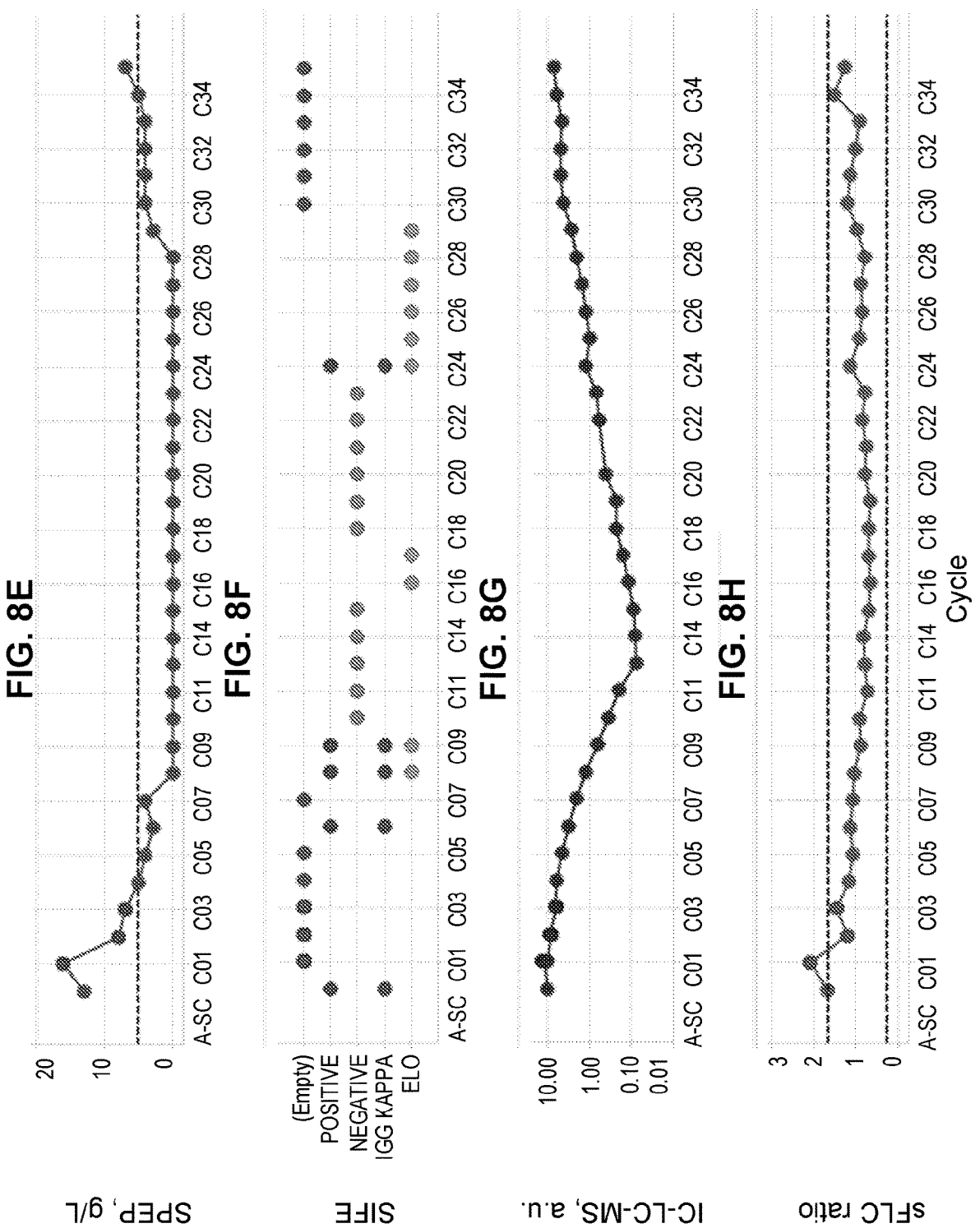

M-PROTEIN ASSAYS

CROSS REFERENCE TO RELATED APPLICATIONS

This PCT application claims the priority benefit of U.S. Provisional Application No. 62/931,063, filed Nov. 5, 2019, which is incorporated herein by reference in its entirety.

FIELD OF THE DISCLOSURE

The present disclosure provides methods for measuring M-protein in a biological sample.

BACKGROUND OF THE DISCLOSURE

Monoclonal gammopathies are hematologic disorders characterized by abnormal production of one or more monoclonal immunoglobulins commonly known as M-protein. M-protein is expressed by rapidly dividing clonal plasma cells in the bone marrow and secreted into the bloodstream, therefore malignant plasma cells can be detected by measuring M-proteins in serum. M-proteins are inherently diverse: variable region of each patient's over-produced antibody is different; however, individual's malignant plasma cell expresses a defined immunoglobulin with a molecular mass identical to its original precursor cell.

Measurement of M-protein is necessary for the diagnosis and monitoring of multiple myeloma patients. Current gel electrophoresis-based M-protein assays have poor sensitivity, specificity and are not quantitative at very low M-protein concentrations due to the presence of immunoglobulins or other serum proteins that co-migrate with M-protein. Accordingly, there is a need for improved methods for measuring M-protein in biological samples.

SUMMARY OF THE DISCLOSURE

Certain aspects of the present disclosure are directed to a method of measuring M-protein in a sample obtained from a subject having a plasma cell disorder, comprising: (i) purifying immunoglobulins and free light chains in the sample by immunocapture, and (ii) applying the immunoglobulins and free light chains to a liquid chromatography (LC) mass spectrometry (MS).

Certain aspects of the present disclosure are directed to a method of reducing a false positive in determining a complete responder after a therapy for a plasma cell disorder, comprising: (i) purifying immunoglobulins and free light chains in the biological sample by immunocapture, and (ii) applying the purified immunoglobulins and free light chains to a liquid chromatography (LC) mass spectrometry (MS).

Certain aspects of the present disclosure are directed to a method of identifying a subject having a residual disease, comprising measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); wherein the subject was previously identified as having a plasma cell disorder.

Certain aspects of the present disclosure are directed to a method of identifying a subject suitable for a therapy to treat a plasma cell disorder, comprising: (i) measuring M-proteins in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS). In some aspects, the method further comprises: (ii) administering to a subject identified as having M-protein a therapy to treat the plasma cell disorder.

In some aspects, the subject has a plasma cell disorder.

Certain aspects of the present disclosure are directed to a method of treating a subject having a plasma cell disorder, comprising: measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); and administering to a subject identified as having M-protein a therapy for the plasma cell disorder.

Certain aspects of the present disclosure are directed to a method of treating a subject having a plasma cell disorder, comprising: (i) administering to the subject a therapy for the plasma cell disorder; (ii) measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); and (iii) administering to the subject an additional therapy for the plasma cell disorder.

In some aspects, the biological sample is a urine sample or a serum sample.

Certain aspects of the present disclosure are directed to a method of treating a subject having a plasma cell disorder, comprising administering to the subject a therapy for the plasma cell disorder, wherein the subject has been identified as having serum and/or urine M-protein, and wherein the serum and/or urine M-protein was measured in a biological sample obtained from the subject by applying immunoglobulins and free light chains purified using immunocapture to a liquid chromatography (LC) mass spectrometry (MS).

In some aspects, the subject received a previous therapy to treat a plasma cell disorder. In some aspects, the previous therapy comprises an immunotherapy. In some aspects, the therapy for a plasma cell disorder comprises an immunotherapy. In some aspects, the immunotherapy comprises an antibody therapy. In some aspects, the immunotherapy comprises a therapy of a checkpoint inhibitor. In some aspects, the antibody comprises an antibody or an antigen binding portion thereof that specifically binds a protein selected from the group consisting of SLAMF7, PD-1, CTLA-4, LAG3, TIGIT, TIM3, NKG2a, OX40, ICOS, CD137, KIR, TGFβ, IL-10, IL-8, IL-2, CD96, VISTA, B7-H4, Fas ligand, CXCR4, mesothelin, CD27, GITR, CD40, CD56, CD38, CD229, CD200, CD28, CD19, BCMA, CD317, CD70, B2M and any combination thereof. In some aspects, the therapy for a plasma cell disorder comprises an anti-SLAMF7 antibody.

In some aspects, the therapy for a plasma cell disorder comprises cyclophosphamide, doxorubicin, etoposide, liposomal doxorubicin, melphalan, vincristine, bortezomib, lenalidomide, carfilzomib, pomalidomide, panobinostat, thalidomide, stem cell transplant, a CAR-T therapy, or any combination thereof.

In some aspects, the M-protein comprises an IgG, an IgA, and IgM, an IgD, a fragment thereof, or any combination thereof. In some aspects, the M-protein comprises a kappa isotype or a lambda isotype. In some aspects, the M-protein comprises one or more free light chain.

In some aspects, the MS comprises an electrospray (ESI) time-of-flight (TOF) MS. In some aspects, the MS comprises a laser desorption ionization (MALDI) TOF. In some aspects, the MS comprises a MALDI TOF MS.

In some aspects, the immunocapture is an automated immunocapture. In some aspects, the purified immunoglobulins are dissociated into light chains and heavy chains. In some aspects, the method further comprises dissociating the purified immunoglobulins into light chains and heavy chains. In some aspects, the purified immunoglobulins are dissociated by chemical reduction. In some aspects, the purified immunoglobulins are dissociated by contacting the purified immunoglobulins with a reagent selected from the group consisting of tris(2-carboxyethyl)phosphine (TCEP); TCEP-HCl and other TCEP salts; DTT (2,3 dihydroxybutane-1,4-dithiol), DTE (2,3 dihydroxybutane-1,4-dithiol); thioglycolates; sulfites; bisulfites; sulfides; bisulfides; 2-Mercaptoethanol; 2-Mercaptoethanol-HCl; Bond-Breaker TCEP Solution, Neutral pH; Cysteine-HCl; Guanidine-HCl; urea; and any combination thereof.

In some aspects, the LC is an ultra-performance (UC) LC. In some aspects, the LC is on-line with the MS.

In some aspects, the plasma cell disorder comprises multiple myeloma. In some aspects, the multiple myeloma comprises a light chain multiple myeloma. In some aspects, the multiple myeloma comprises a plasma cell leukemia. In some aspects, the plasma cell leukemia comprises a primary plasma cell leukemia or a secondary plasma cell leukemia.

In some aspects, the anti-SLAMF7 antibody cross-competes with elotuzumab for binding to human SLAMF7. In some aspects, the anti-SLAMF7 antibody binds the same or an overlapping epitope on human SLAMF7 as elotuzumab. In some aspects, the anti-SLAMF7 antibody is a human antibody, a humanized antibody, or a chimeric antibody. In some aspects, the anti-SLAMF7 antibody is elotuzumab. In some aspects, the anti-SLAMF7 antibody is administered intravenously.

In some aspects, the method further comprises administering an additional anti-cancer agent to the subject. In some aspects, the method further comprises administering lenalidomide to the subject. In some aspects, the method further comprises administering pomalidomide to the subject. In some aspects, the method further comprises administering dexamethasone to the subject. In some aspects, the method further comprises administering diphenhydramine to the subject. In some aspects, the method further comprises administering ranitidine to the subject. In some aspects, the method further comprises administering acetaminophen to the subject.

In some aspects, the residual disease comprises a minimal residual disease (MRD).

Figure 2A:
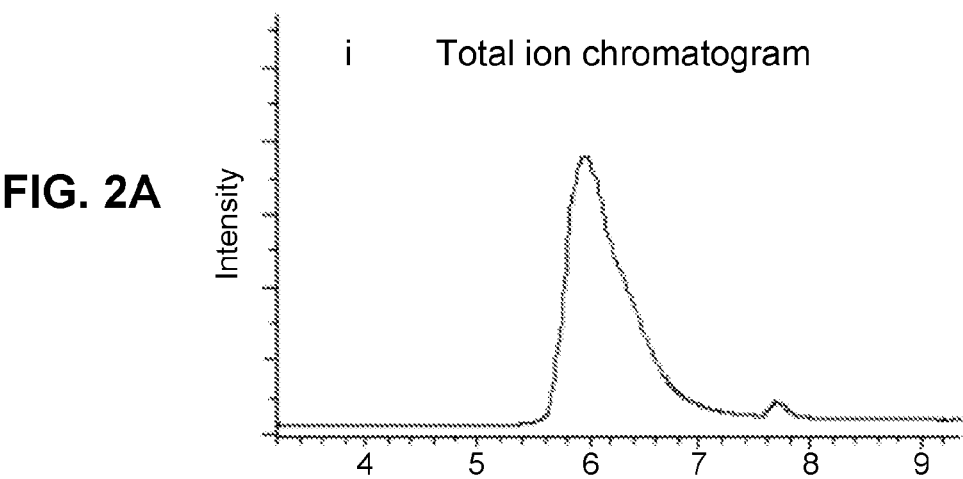
FIGS. 2A-2I are graphical representations showing results of a simplified separation of immunoglobulins by liquid chromatography (FIGS. 2A, 2D, and 2G), representative mass spectra (FIGS. 2B, 2E, and 2H), and reconstructed spectra (FIGS. 2C, 2F, and 2I) for: immunocaptured immunoglobulins from normal human serum (FIGS. 2A-2C); immunocaptured immunoglobulins from a serum sample
Figure 2B:
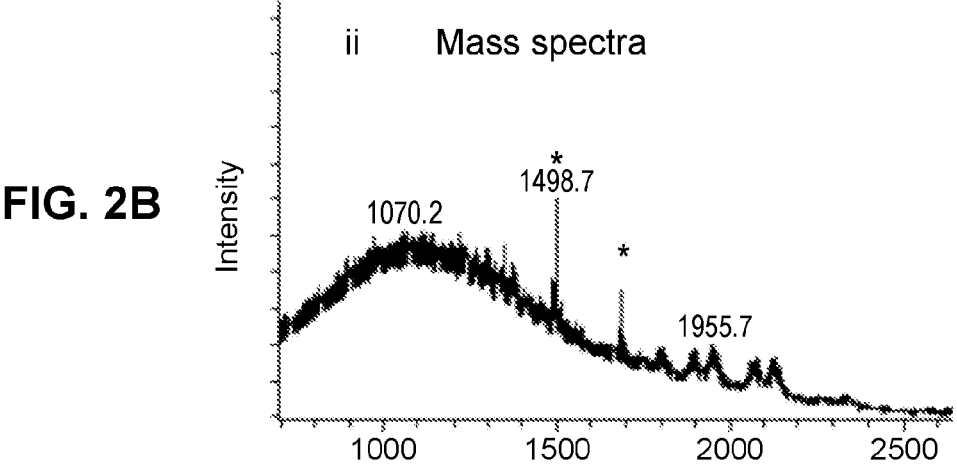
Figure 2C:
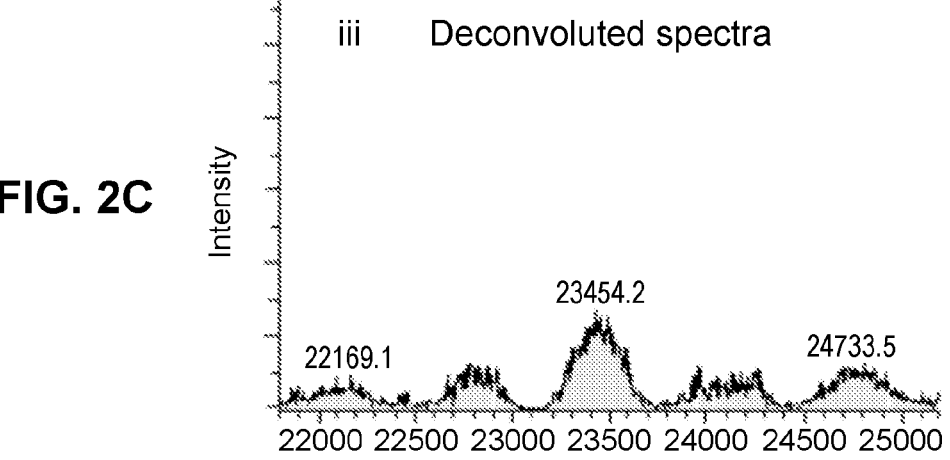
Figure 2D:
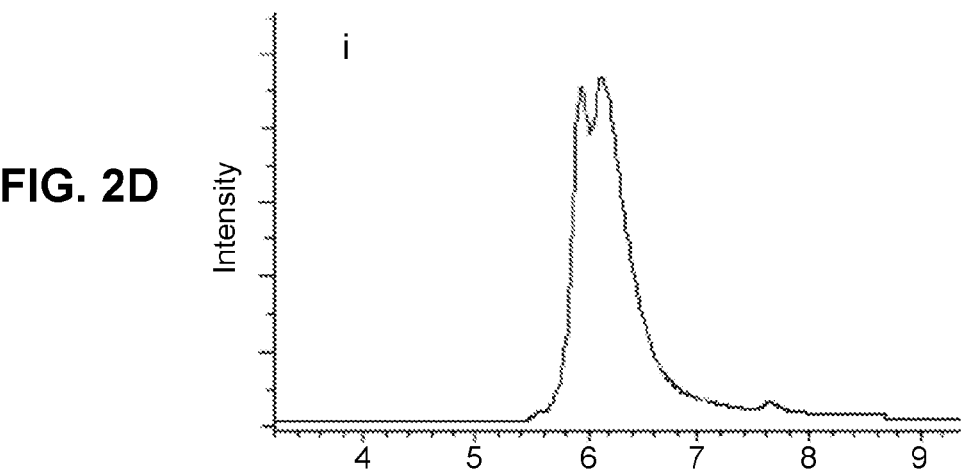
Figure 2E:
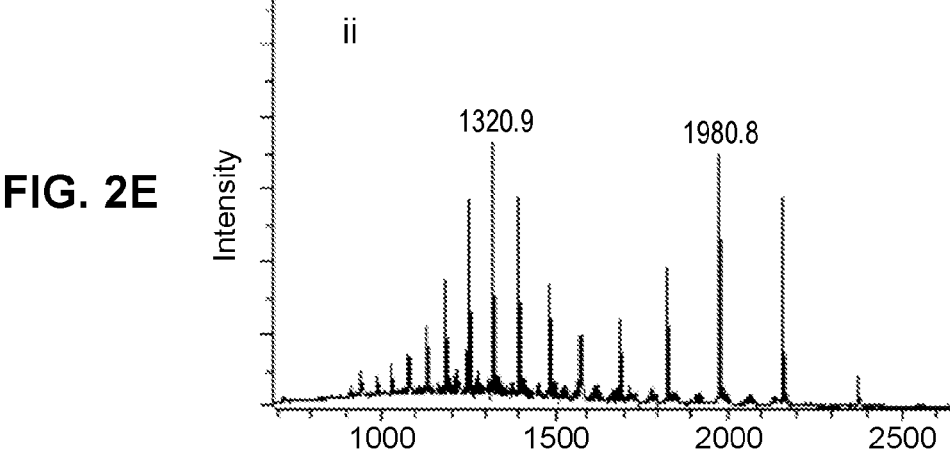
Figure 2F:
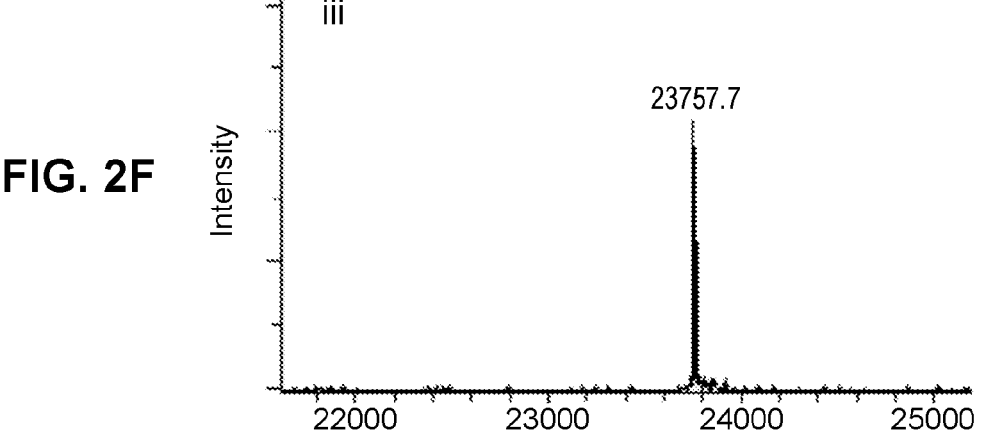
Figure 2G:
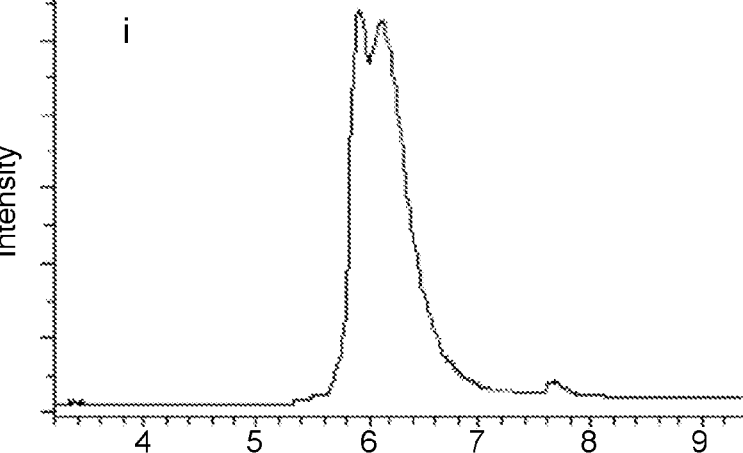
Figure 2H:
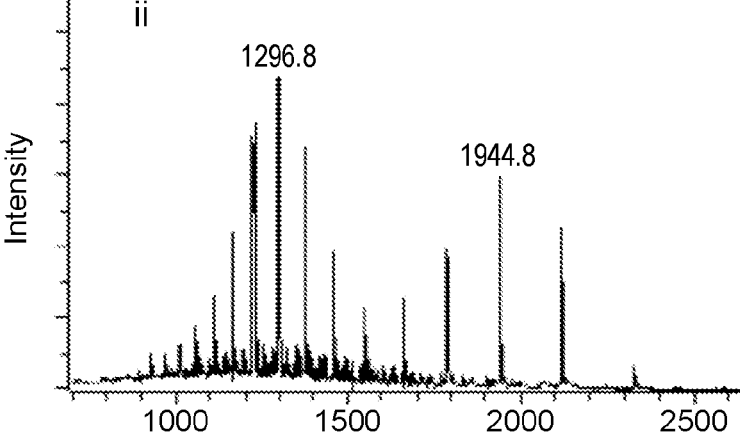
Figure 2I:
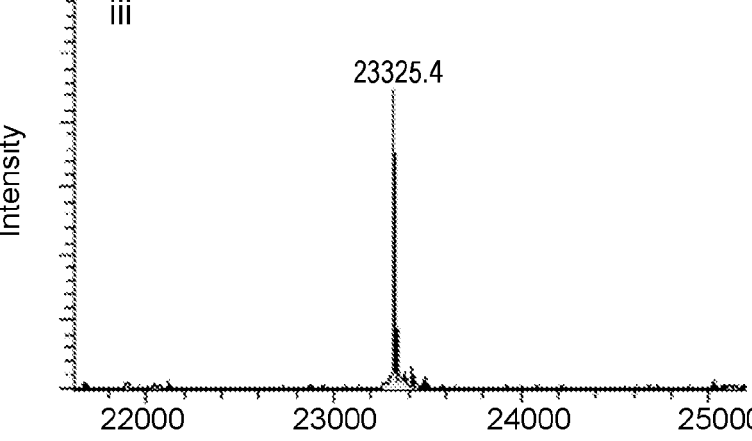

4 obtained from a first multiple myeloma patient serum (FIGS. 2D-2F); and immunocaptured immunoglobulins from a serum sample obtained from a second multiple myeloma patient (FIGS. 2G-2I).

Figure 3:
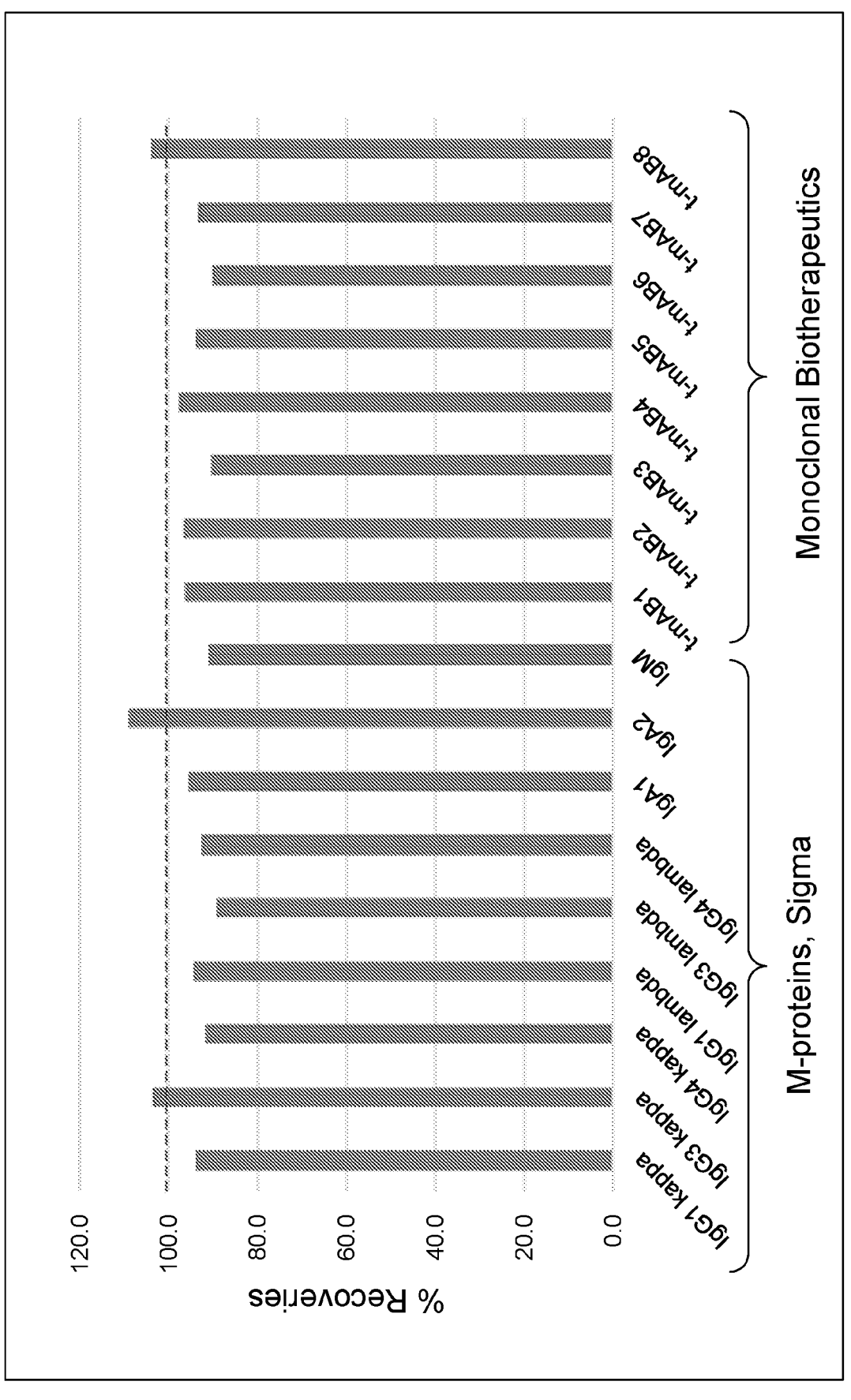

FIG. 3 is a graphical representation of consistent high-yield recoveries of M-proteins and monoclonal therapeutic antibodies (t-mAb) using the PHYTIP™ anti-lambda/kappa capture approach.

Figure 4:
Figure 4:
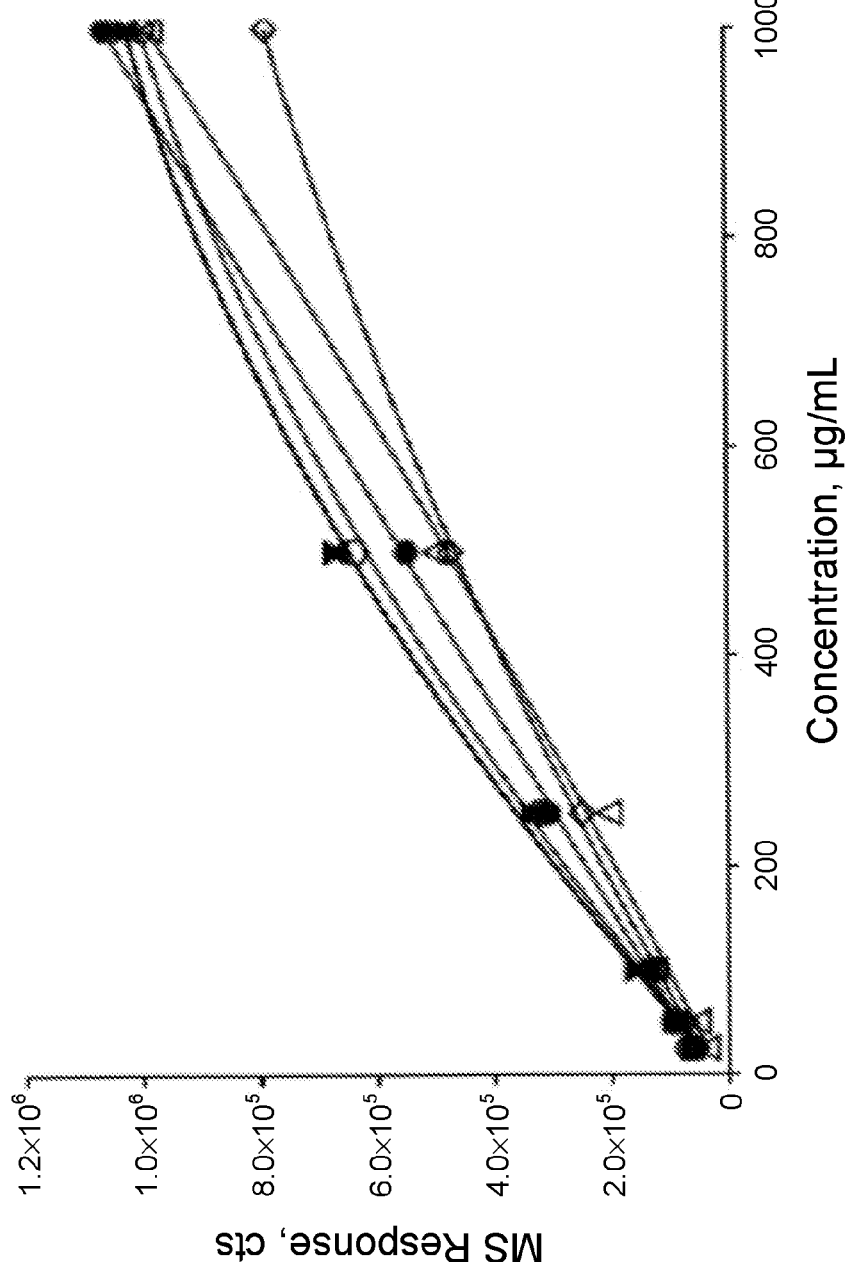

FIG. 4 shows a graph of deconvoluted light chain standard curves for five non-identical therapeutic mAbs (t-mAbs), as indicated.

Figure 5A:
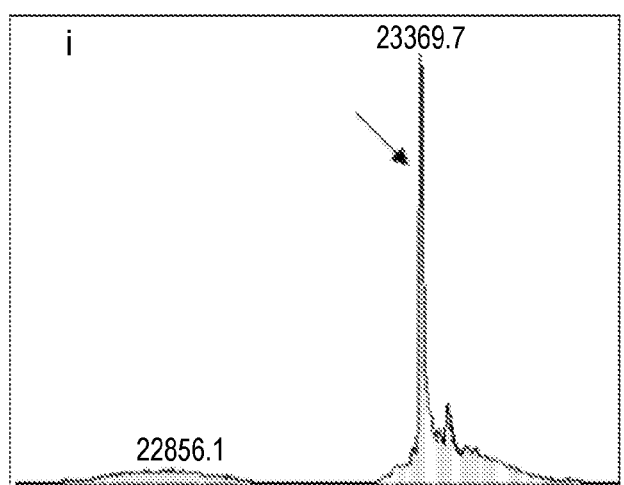
Figure 5B:
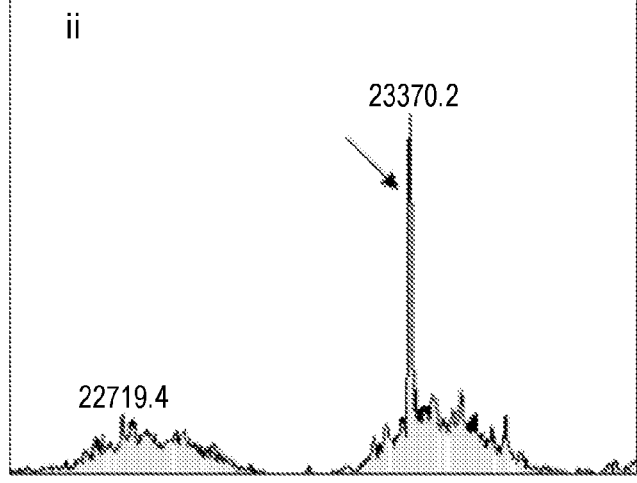
Figure 5C:
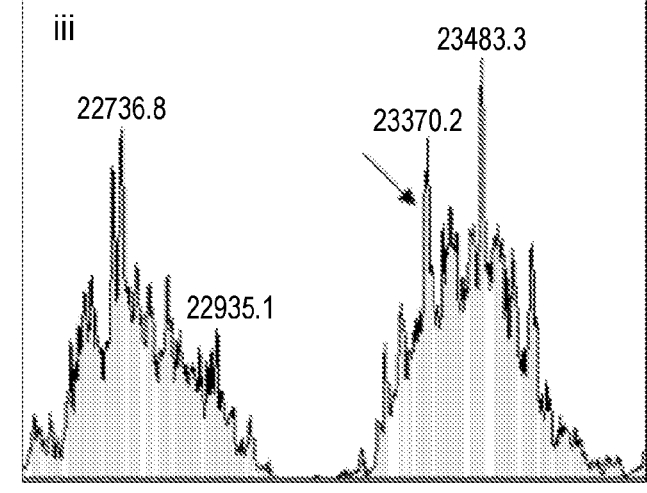
Figure 5D:
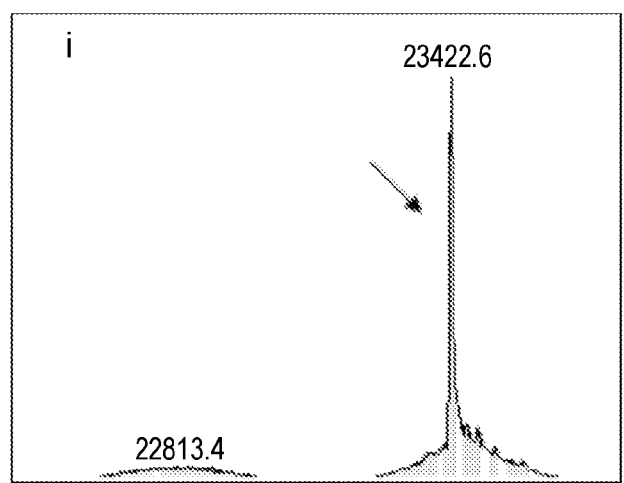
Figure 5E:
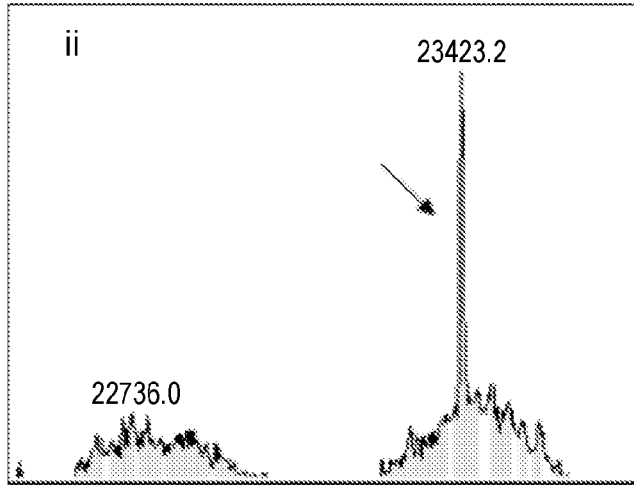
Figure 5F:
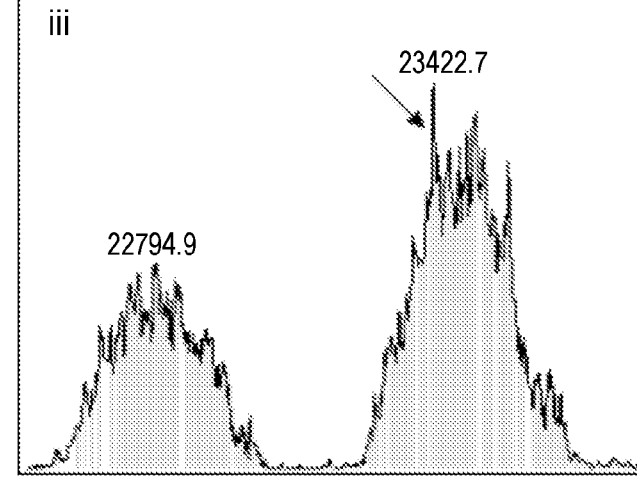
Figure 5G:
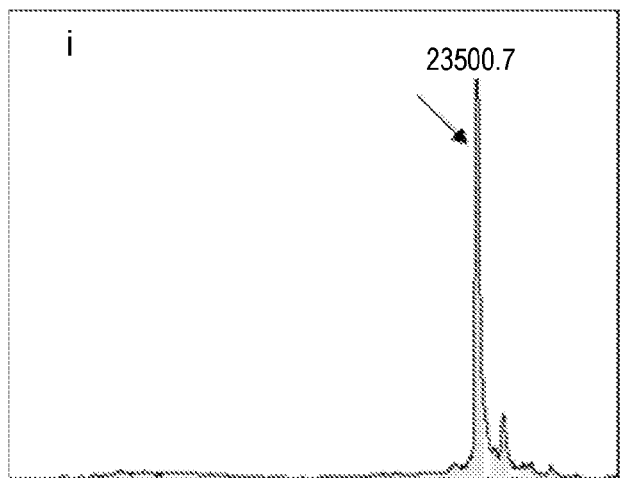
Figure 5H:
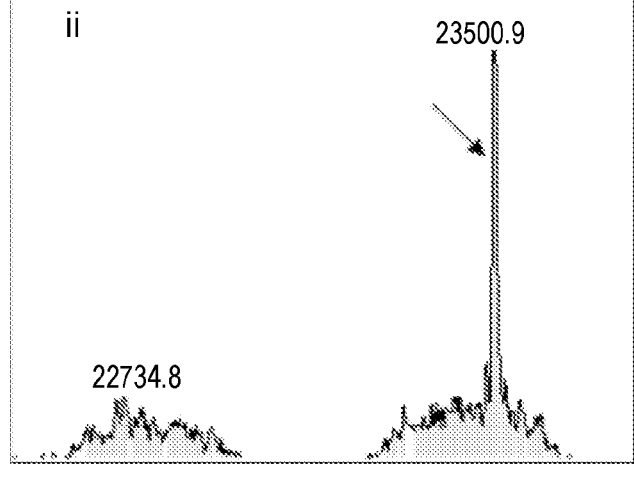
Figure 5I:
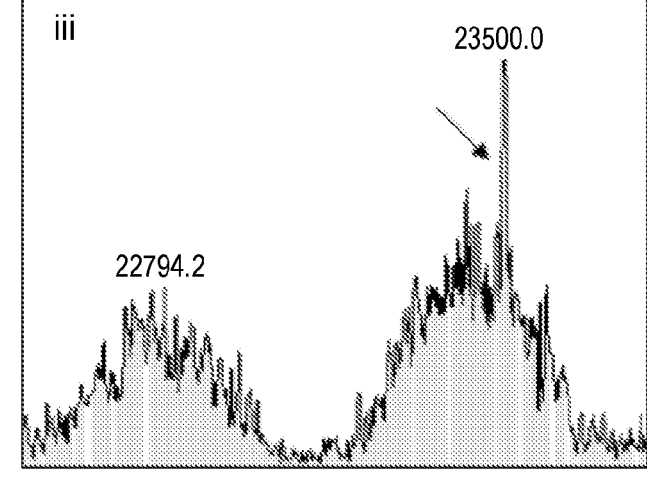

FIGS. 5A-5I show low-level quantification of a single monoclonal antibody light chain above the polyclonal background. Three individual monoclonal antibodies were spiked into normal human serums and tested using the immunocapture IC-LC-MS methodology. Results for mAb1 are shown in FIGS. 5A-5C, mAb2 in FIGS. 5D-5F, and mAb3 in FIGS. 5G-5I. Each antibody was tested at concentrations of 1000 μg/mL (FIGS. 5A, 5D, and 5G), 100 μg/mL (FIGS. 5B, 5E, and 5H), and 10 μg/mL (FIGS. 5C, 5F, and 5I). An estimated LOD for the immunocapture IC-LC-HRMS methodology is 100-fold lower than that of the clinical SPEP assay which has sensitivity of 1000 μg/mL. FIGS. 5J-5M show a limit of detection for IC-LC-MS on artificial samples composed by spiking different M-proteins (IgGK, FIG. 5J; IgGL, FIG. 5K; IgAK, FIG. 5L; and IgAL, FIG. 5M) into healthy serum. Limit of detection varies with the ratio of M-protein peak to polyclonal background.

Figure 6:
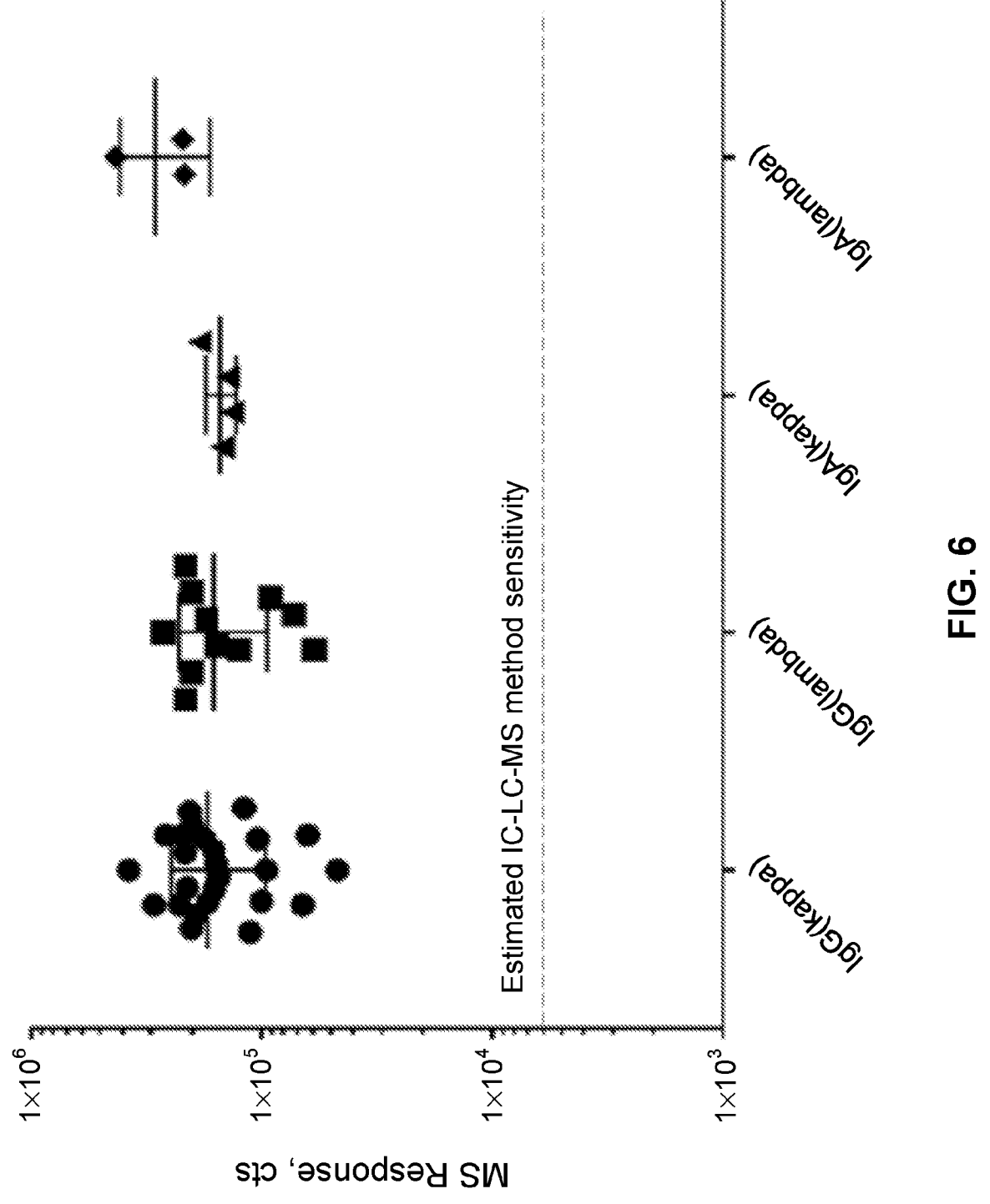

FIG. 6 is a plot representing the distribution of the M-protein MS responses measured by the IC-LC-MS method at the lowest serial dilution concentration measurable by SIFE. The estimated IC-LC-MS method LOD is 10-100-fold lower than the SIFE LOD.

Figure 7A:
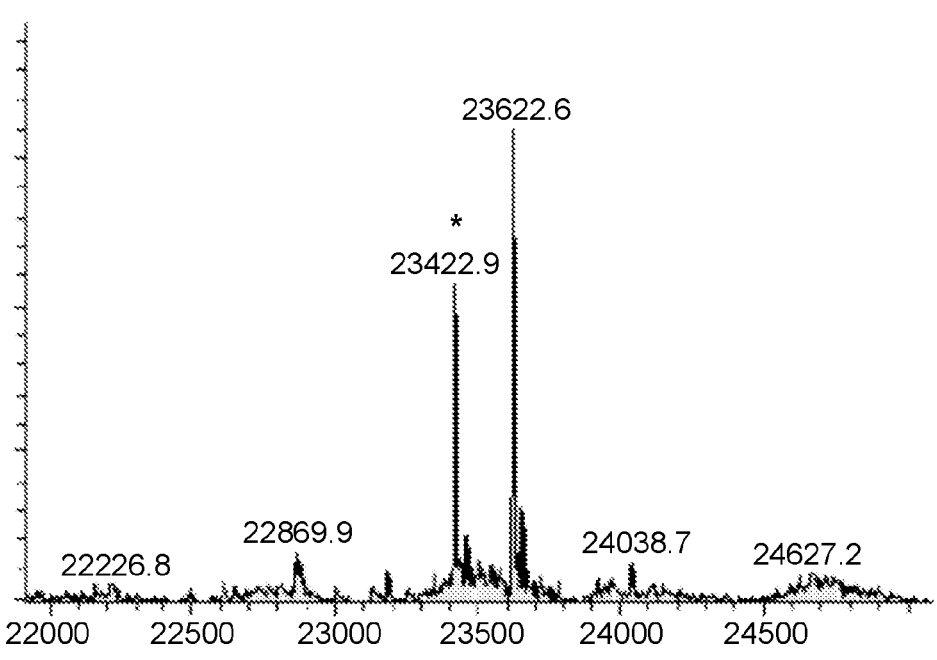
Figure 7B:
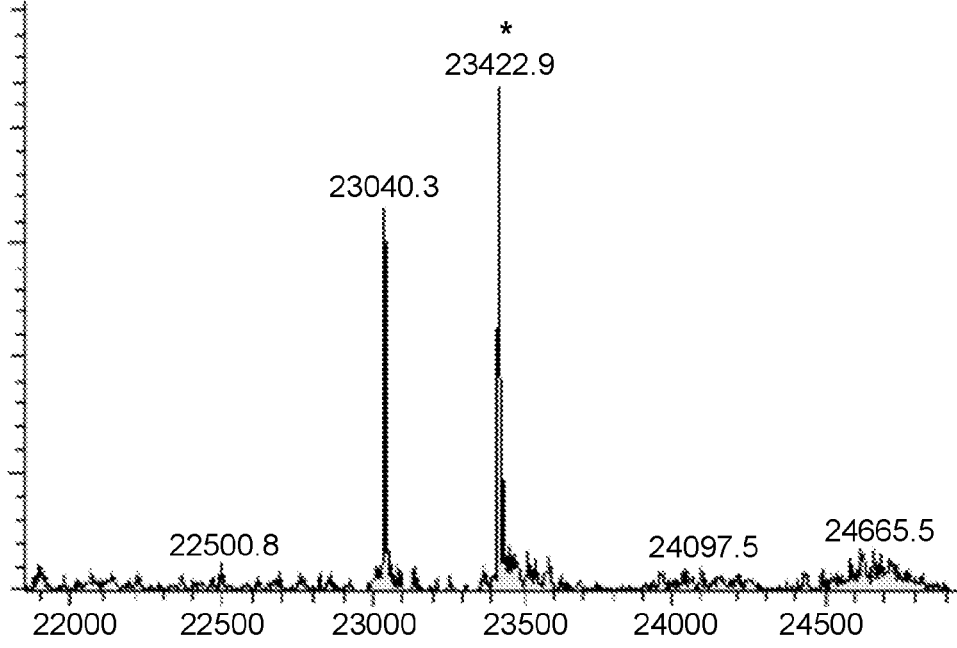
Figure 7C:
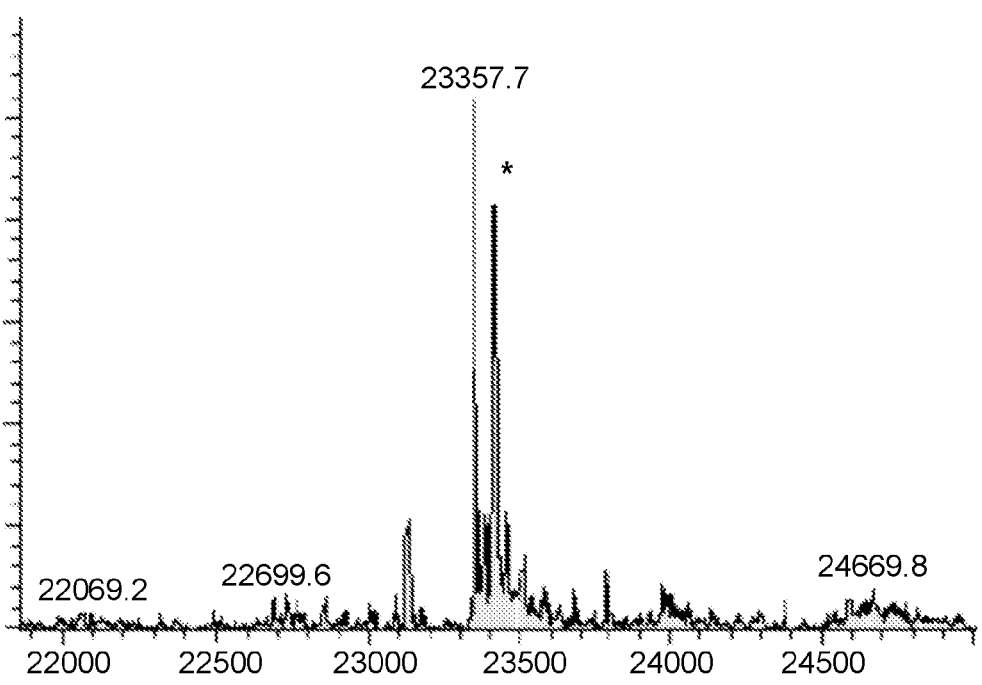
Figure 7D:
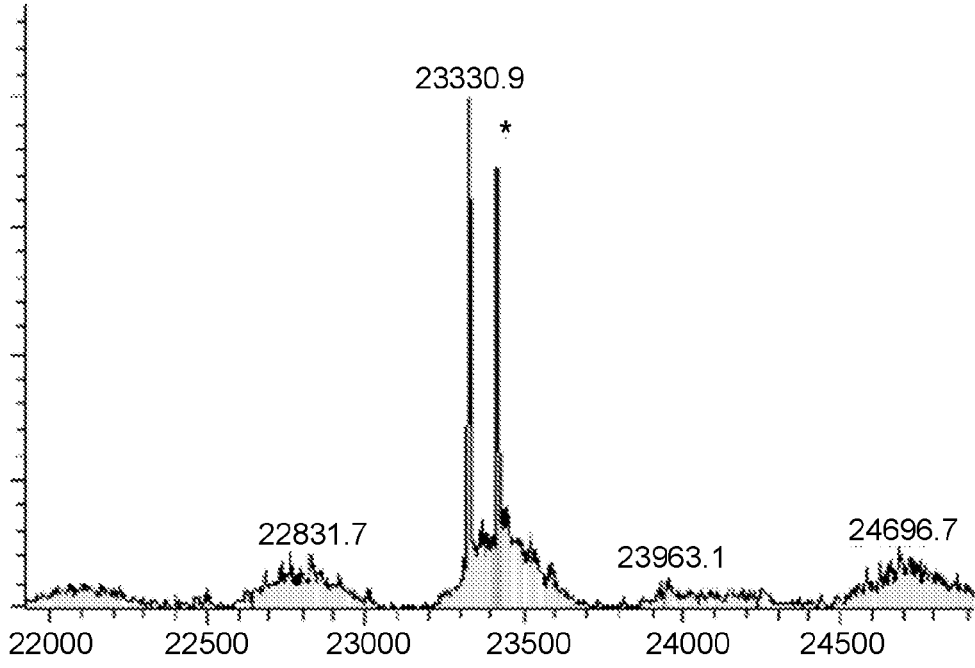
Figures 7E, 7F, 7G:
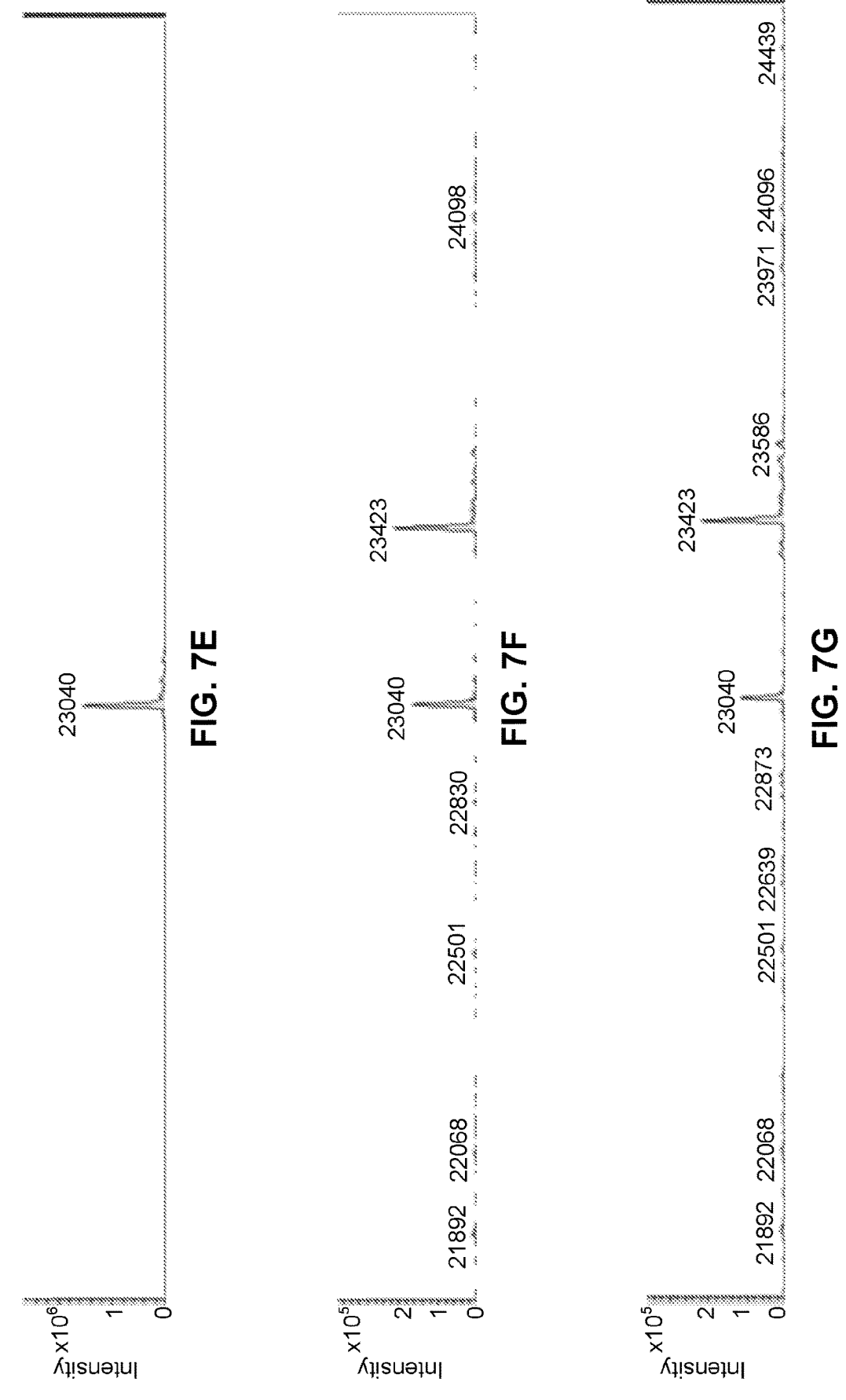
Figure 7N:
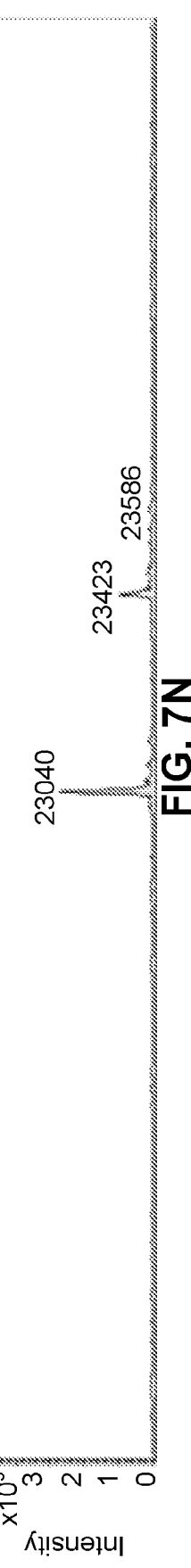

FIGS. 7A-7N are representative mass spectra showing that the IC-LC-MS method assay eliminates interference from therapeutic monoclonal antibodies when detecting M-proteins.

Figures 8A, 8B, 8C, 8D:
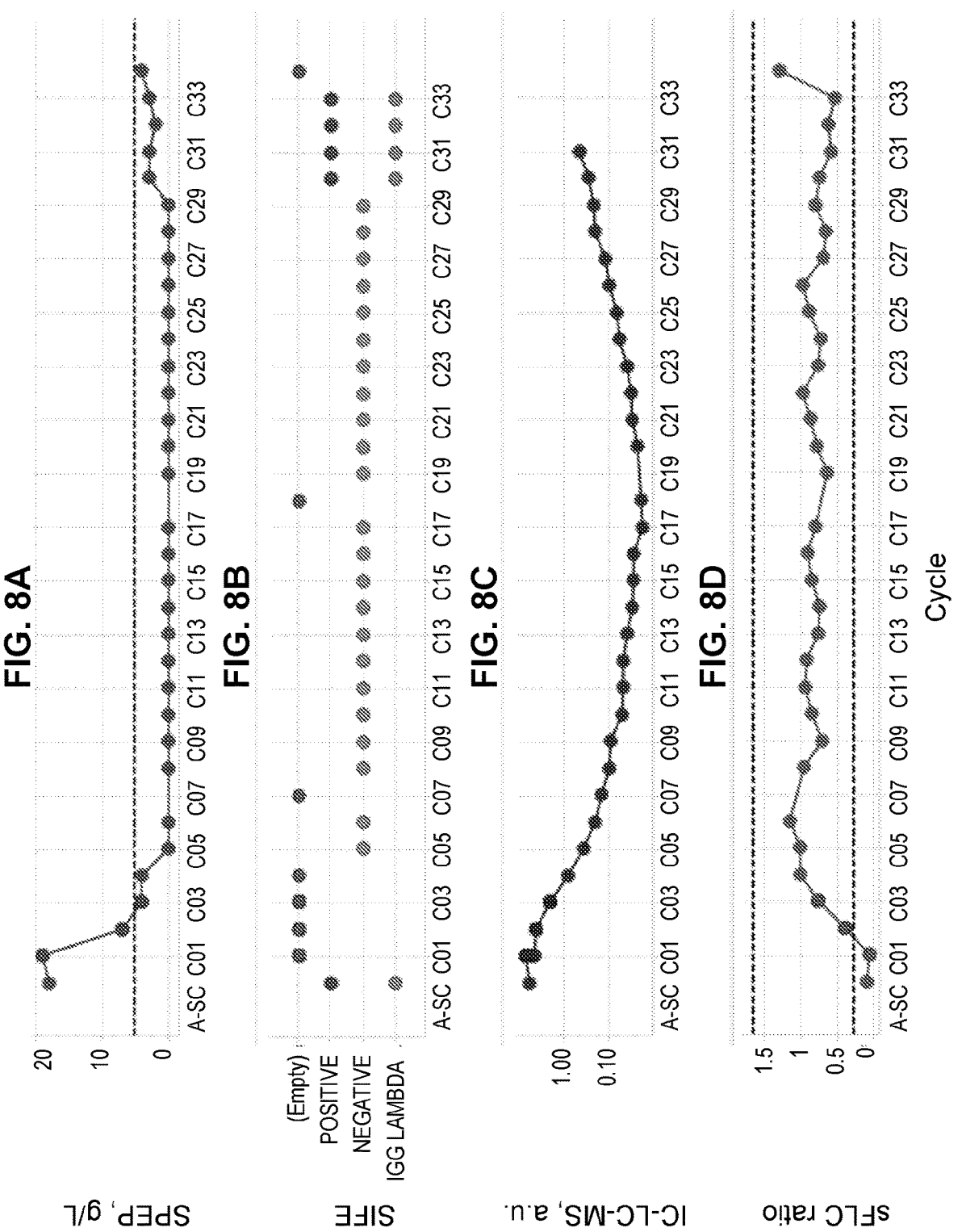
Figure 9A:
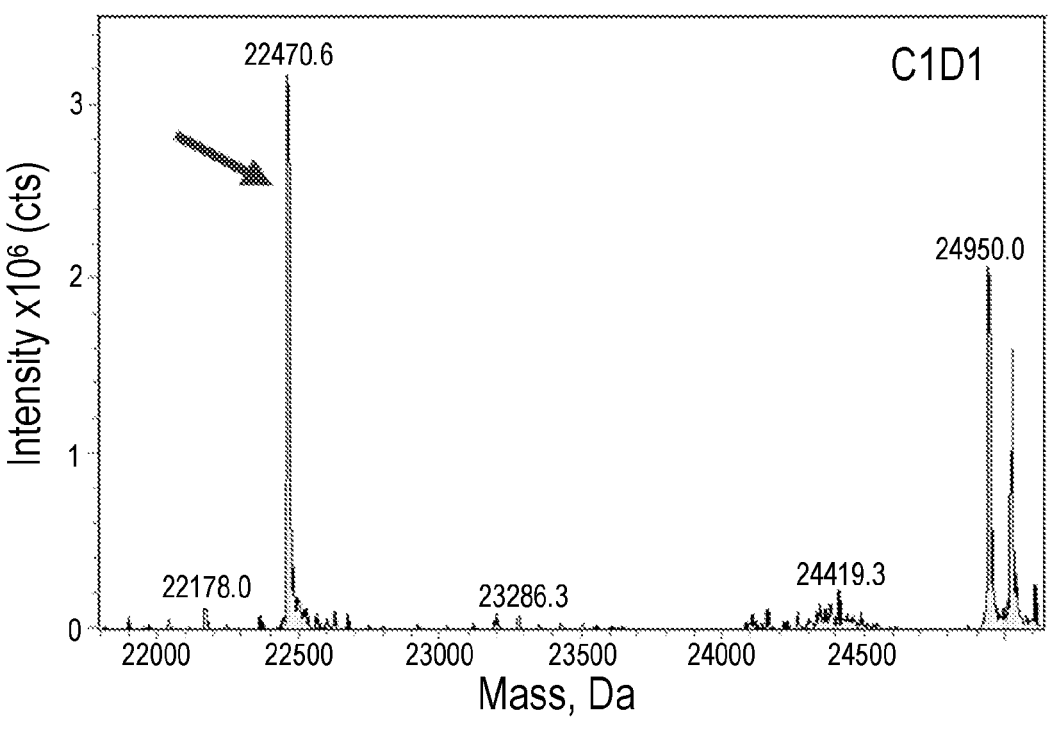
Figure 9B:
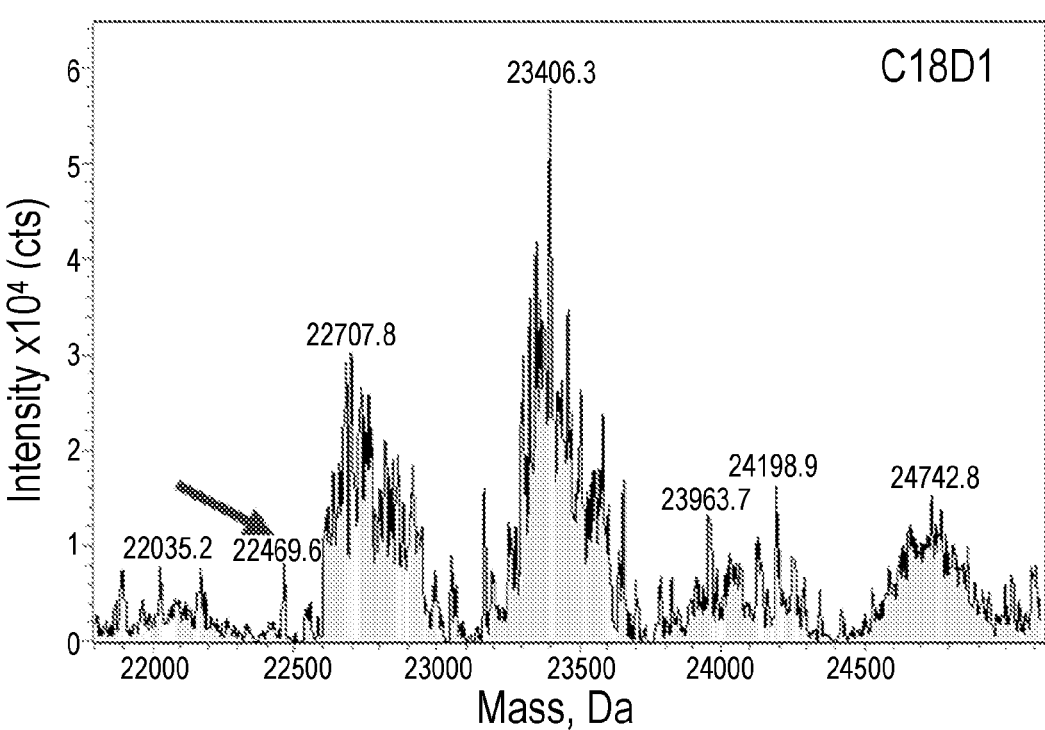
Figure 9C:
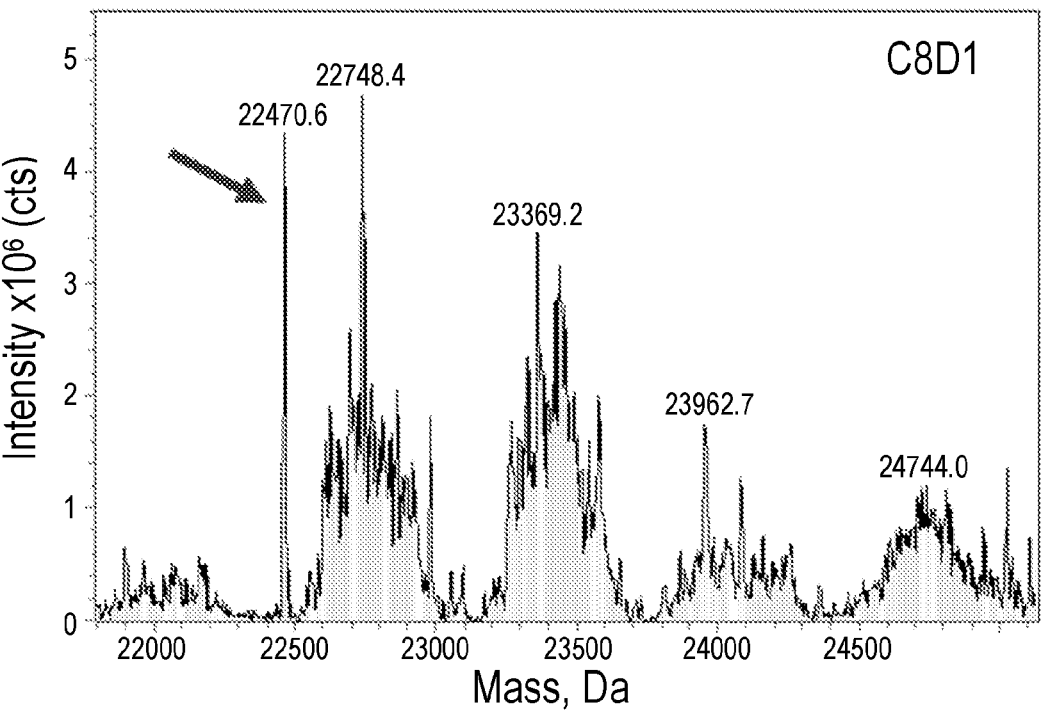
Figure 9D:
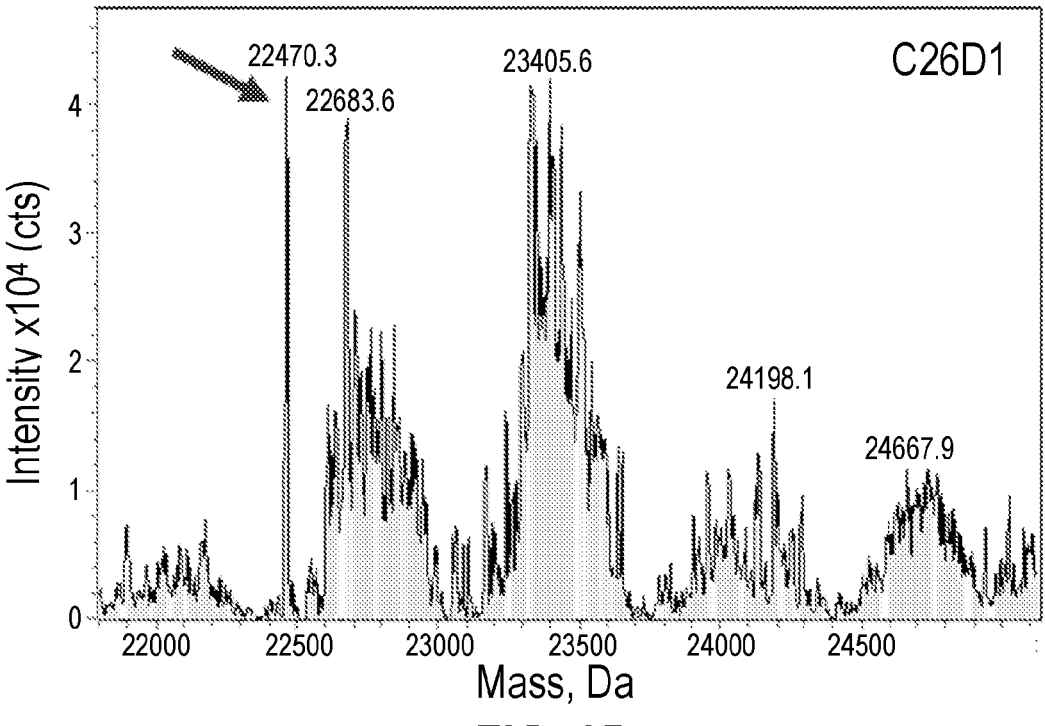
Figure 9E:
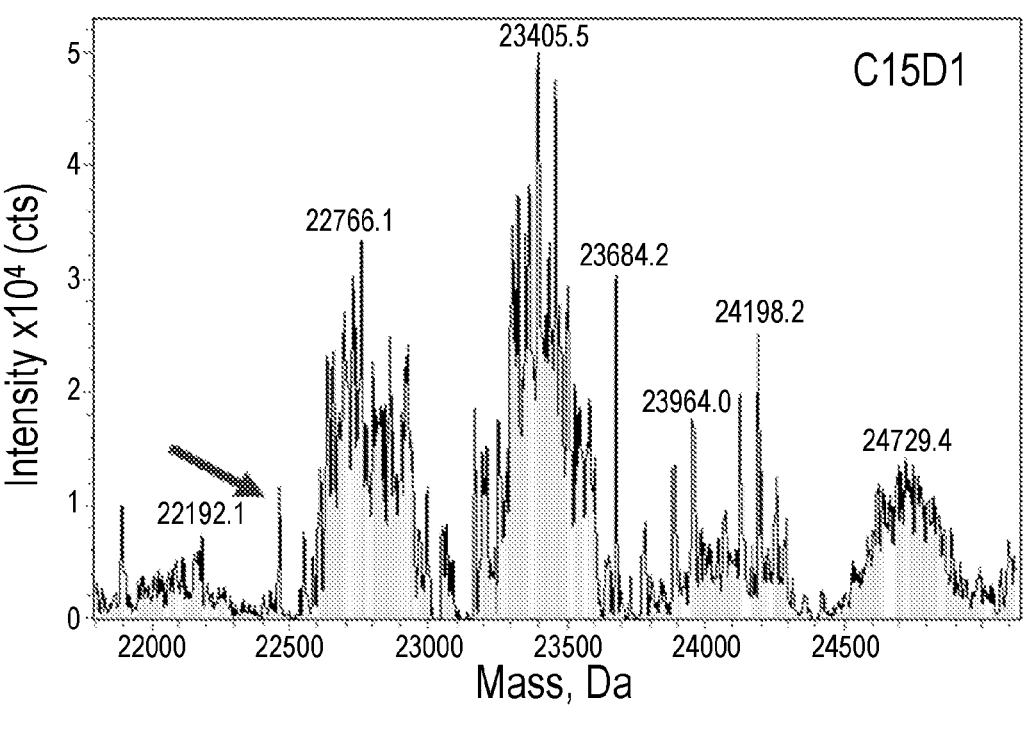
Figure 9F:
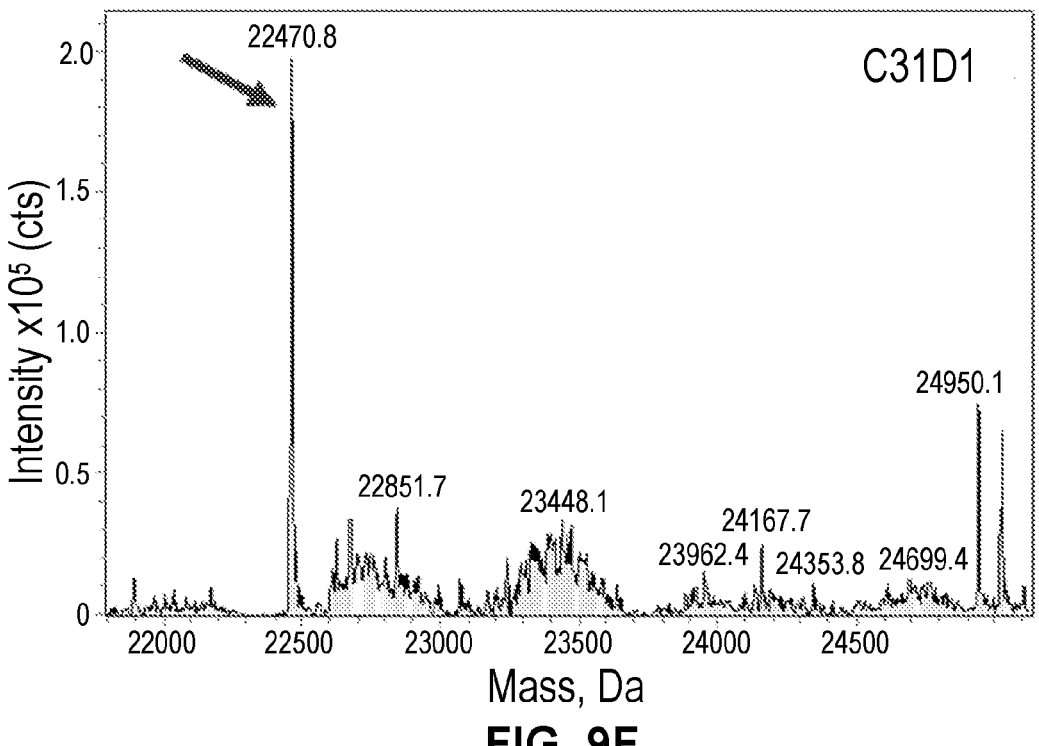

FIGS. 8A-8H are graphical representations showing sensitivities of standard clinical tests (SPEP, FIGS. 8A and 8E; SIFE, FIGS. 8B and 8F; and sFLC, FIGS. 8D and 8H) as compared to IC-LC-MS assay (FIGS. 8C and 8G). Serum samples collected from two multiple myeloma patients (patient 1, FIGS. 8A-8D; patient 2, FIGS. 8E-8H) at different treatment cycles (1 cycle is 28 days) were used for this analysis.

FIGS. 9A-9F are graphical representations of immunoglobulin profiles by IC-LC-MS assay for C1D1 (FIG. 9A), C18D1 (FIG. 9B), C8D1 (FIG. 9C), C26D1 (FIG. 9D), C15D1 (FIG. 9E), and C31D1 (FIG. 9F), in serum samples from a multiple myeloma patient, which show detectable monoclonal light chain peak at 22470±1.5 Da in all treatment time points.

DETAILED DESCRIPTION OF THE DISCLOSURE

The present disclosure provides a method for measuring M-protein in a sample obtained from a subject. The present disclosure also provides a method for identifying a subject suitable for a therapy for a plasma cell disorder, comprising measuring M-protein in a sample obtained from a subject. In some aspects, the M-protein is measured by purifying immunoglobulins and/or free light chains in the sample and applying the purified immunoglobulins and free light chains to a liquid chromatography (LC) mass spectrometry (MS). In some aspects, the immunoglobulins and/or free light chains are purified using immunocapture. In some aspects, the method further comprises administering a therapy for a plasma cell disorder. In some aspects, the method further comprises administering an antibody or an antigen-binding portion thereof that is useful to treat a plasma cell disorder, e.g., an antibody specifically binding human SLAMF7 (an anti-SLAMF7 antibody) to the subject.

I. Terms

In order that the present disclosure can be more readily understood, certain terms are first defined. As used in this application, except as otherwise expressly provided herein, each of the following terms shall have the meaning set forth below. Additional definitions are set forth throughout the application.

The term "M-protein," as used herein, refers to a diverse group of immunoglobulins, which are the result of the abnormal production of one or more monoclonal immunoglobulins by a monoclonal gammopathy, e.g., multiple myeloma, in a subject. M-protein is expressed by rapidly dividing clonal plasma cells in the bone marrow and secreted into the bloodstream. M-proteins are inherently diverse: variable region of each patient's over-produced antibody is different; however, individual's malignant plasma cell expresses a defined immunoglobulin with a molecular mass identical to its original precursor cell. Based on the constant region of heavy chain, M-proteins can belong to IgG, IgA, IgM, or IgD class. In multiple myeloma, IgG is the most common immunoglobulin with IgA being the second most common, and IgM comprising only less than 0.5% cases, and IgD being extremely rare. Based on the constant region of light chain, each immunoglobulin can be divided into kappa and lambda isotypes. Each M-protein can consist essentially of or consist of intact immunoglobulin molecule and/or immunoglobulin fragments such as "free light chains" (FLCs) also known as Bence Jones proteins. "Free light chains" refers to light chains of immunoglobulins that are not associated with a heavy chain. The presence of free light chains in the urine or serum is one of several markers for multiple myeloma. Free light chains can exist as low molecular weight monomers, dimers, or high molecular weight polymers in the urine and as tetramers in serum.

Because M-protein is typically secreted into the bloodstream, malignant plasma cells can be detected by measuring M-proteins in serum. The term "measuring" or "measured" or "measurement" means determining a measurable quantity of M-protein in a biological sample obtained from a subject. As used herein, the measuring is achieved using methods that comprise a mass spectrometry step. Mass spectrometry is an analytical tool useful for measuring the mass-to-charge ratio (m/z) of one or more molecules present in a sample. These measurements can often be used to calculate the exact molecular weight of the sample components as well. Typically, mass spectrometers can be used to identify unknown compounds via molecular weight determination, to quantify known compounds, and to determine structure and chemical properties of molecules. In the methods disclosed herein, purified and reduced immunoglobulins are applied to a mass spectrometer, increasing the ability to identify M-proteins in a biological sample.

The term "biological sample" as used herein refers to biological material isolated from a subject. The biological sample can contain any biological material that may comprise M-protein. The biological sample can be any suitable biological tissue or fluid such as, for example, blood, blood plasma, serum, a bone marrow biopsy, and/or urine. In one aspect, the sample is a serum sample. In one aspect, the sample is a urine sample. In one aspect, the sample is a bone marrow biopsy.

A "monoclonal gammopathy," as used herein, refers to a type of hematologic disorder, which is characterized by production of one or more M-proteins. Monoclonal gammopathies range from benign, such as monoclonal gammopathy of undetermined significance, to cancerous such as multiple myeloma.

As used herein, a "plasma cell disorder" refers to a spectrum of progressively more severe monoclonal gammopathies in which a clone or multiple clones of premalignant or malignant plasma cells (sometimes in association with lymphoplasmacytoid cells or B lymphocytes) over-produce and secrete M-protein into the blood stream. Nonexclusive examples of plasma cell disorders include monoclonal gammopathy of undetermined significance (MGUS) and hematological malignancies, including, multiple myeloma, Waldenström's macroglobulinemia, and other B cell-associated neoplasm.

As used herein, "multiple myeloma" or "plasma cell myeloma" refers to a cancer of plasma cells. Plasma cells are a class of white blood cell that produces antibodies. Multiple myeloma is further associated with accumulation of cancer cells in the bone marrow. The cancerous cells produce abnormal monoclonal antibodies (M-proteins).

"Administering" refers to the physical introduction of a composition comprising a therapeutic agent to a subject, using any of the various methods and delivery systems known to those skilled in the art. Non-limiting examples of routes of administration include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Other non-parenteral routes include an oral, topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) or "immunoglobulin" shall include, without limitation, a glycoprotein immunoglobulin that binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. In humans, immunoglobulin light chains are encoded by two loci: the immunoglobulin kappa locus and the immunoglobulin lambda locus. As such, a human immunoglobulin light chain is classified as either a kappa light chain or a lambda light chain. CaptureSelect™ LC-lambda and LC-kappa nanobodies (THERMOFISHER) as well as various commercial antibodies are available that can specifically bind either kappa light chain or lambda light chain, including, without limitation, Kappa-FITC (C15623), Lambda-PE (C15189), Lambda-PC7 (B90416), and Kappa-APC (B90420) by Beckman Coulter Life Sciences; Anti-Kappa light chain antibodies (e.g., ab134083, ab79558, and ab1936) and Anti-Lambda Light chain antibodies (e.g., ab124719, ab187370, ab185131, and ab200966) by Abcam; and Kappa Light Chain Monoclonal Antibody (TB28-2), FITC, and Lambda light chain Monoclonal Antibody (1-155-2), APC, by eBioscience™. These examples are not intended to be limiting, and any known anti-kappa and/or anti-lambda capture reagents can be used in the methods disclosed herein.

The term "capture reagent" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies, nanobodies, affirmers, other analyte binding proteins and aptamers, and any combination thereof. Where not expressly stated, and unless the context indicates otherwise, the term "capture reagent" also includes an antigen-binding fragment or an antigen-binding portion of any of the aforementioned immunoglobulins, and includes a monovalent and a divalent fragment or portion, and a single chain antibody.

As used herein, an antigen-binding "portion" or "fragment" of an antibody, e.g., a therapeutic antibody, refers to a part of the antibody that is less than the whole, which retains the ability to bind an antigen. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, or (v) any combination thereof.

A "therapeutic antibody," as used herein, refers to an antibody, or an antigen-binding portion thereof, that is capable of binding an antigen and eliciting an effect in vivo or in vitro.

An "isolated antibody" refers to an antibody that is substantially free of other antibodies having different antigenic specificities (e.g., an isolated antibody that binds specifically to SLAMF7 is substantially free of antibodies that bind specifically to antigens other than SLAMF7). An isolated antibody that binds specifically to SLAMF7 may, however, have cross-reactivity to other antigens, such as SLAMF7 molecules from different species. Moreover, an isolated antibody can be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies can be produced by hybridoma, recombinant, transgenic or other techniques known to those skilled in the art.

A "human antibody" (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibody" and "fully human antibody" and are used synonymously.

A "humanized antibody" refers to an antibody in which some, most or all of the amino acids outside the CDRs of a non-human antibody are replaced with corresponding amino acids derived from human immunoglobulins. In one aspect of a humanized form of an antibody, some, most or all of the amino acids outside the CDRs have been replaced with amino acids from human immunoglobulins, whereas some, most or all amino acids within one or more CDRs are unchanged. Small additions, deletions, insertions, substitutions or modifications of amino acids are permissible as long as they do not abrogate the ability of the antibody to bind to a particular antigen. A "humanized antibody" retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen antibody" refers to an antibody that binds specifically to the antigen. For example, an anti-SLAMF7 antibody binds specifically to SLAMF7.

A "cancer" refers a broad group of various diseases characterized by the uncontrolled growth of abnormal cells in the body. Unregulated cell division and growth divide and grow results in the formation of malignant tumors that invade neighboring tissues and can also metastasize to distant parts of the body through the lymphatic system or bloodstream.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some aspects, an immunotherapy comprises administering a therapeutic antibody to a subject.

"Signaling lymphocytic activation molecule F7," "SLAMF7," "CD319," or "CS-1" refers to an immunoregulator receptor expressed by natural killer (NK) cells, activated T cells, most B cells, and multiple myeloma cells. In cells co-expressing SH2D1B, SLAMF7 positively regulates NK cell functions by a mechanism dependent on phosphorylated SH2D1B. In the absence of SH2D1B, SLAMF7 inhibits NK cell function. The term "SLAMF7" as used herein includes human SLAMF7 (hSLAMF7), variants, isoforms, and species homologs of hSLAMF7, and analogs having at least one common epitope with hSLAMF7. The complete hSLAMF7 sequence can be found under UniProt No. Q9NQ25.

A "subject" includes any human or nonhuman animal. The term "nonhuman animal" includes, but is not limited to, vertebrates such as nonhuman primates, sheep, dogs, and rodents such as mice, rats and guinea pigs. In preferred aspects, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an "anti-cancer agent" promotes cancer regression in a subject. In preferred aspects, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4$^+$ cell, a CD8$^+$ T cell, or a Treg cell, or activation or inhibition of any other cell of the immune system, e.g., NK cell.

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

An "immunomodulator" or "immunoregulator" refers to an agent, e.g., an agent targeting a component of a signaling pathway that can be involved in modulating, regulating, or modifying an immune response. "Modulating," "regulating," or "modifying" an immune response refers to any alteration in a cell of the immune system or in the activity of such cell (e.g., an effector T cell, such as a Th1 cell). Such modulation includes stimulation or suppression of the immune system which can be manifested by an increase or decrease in the number of various cell types, an increase or decrease in the activity of these cells, or any other changes which can occur within the immune system. Both inhibitory and stimulatory immunomodulators have been identified, some of which can have enhanced function in a tumor microenvironment. In some aspects, the immunomodulator targets a molecule on the surface of a T cell. An "immunomodulatory target" or "immunoregulatory target" is a molecule, e.g., a cell surface molecule, that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying the immune system or an immune response. In certain aspects, the immunotherapy comprises administering an antibody to a subject. In other aspects, the immunotherapy comprises administering a small molecule to a subject. In other aspects, the immunotherapy comprises administering a cytokine or an analog, variant, or fragment thereof.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred aspects, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. Methods of the Disclosure

Certain aspects of the present disclosure are directed to methods of treating a subject having a plasma cell disorder, comprising: measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); and administering to a subject identified as having M-protein a therapeutically effective amount of an immunotherapy. In some aspects, the immunotherapy comprises an antibody or an antigen binding portion thereof that specifically binds SLAMF7 ("an anti-SLAMF7 antibody").

Some aspects of the present disclosure are directed to methods of treating a subject having a plasma cell disorder, comprising: (i) administering to the subject a therapeutically effective amount of an immunotherapy; (ii) measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); and (iii) administering to the subject an additional therapeutically effective amount of the immunotherapy. In some aspects, the immunotherapy comprises an anti-SLAMF7 antibody.

Some aspects of the present disclosure are directed to methods of identifying a subject suitable for an immunotherapy, comprising: (i) measuring M-proteins in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS). In some aspects, the method further comprises administering to a subject identified as having M-protein a therapeutically effective amount of the immunotherapy. In some aspects, the immunotherapy comprises an anti-SLAMF7 antibody. In some aspects, the subject has a plasma cell disorder.

Some aspects of the present disclosure are directed to methods of identifying a subject having a residual disease, comprising measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); wherein the subject was previously identified as having a plasma cell disorder.

Some aspects of the present disclosure are directed to methods of measuring M-protein in a biological sample obtained from a subject, comprising: (1) purifying immunoglobulins and free light chains in the biological sample by immunocapture, and (2) applying the purified immunoglobulins and free light chains to a liquid chromatography (LC) mass spectrometry (MS). In some aspects, the subject has a plasma cell disorder.

In some aspects, the methods disclosed herein reduce the occurrence of false positives. Among the treatment options for treating plasma cell disorders, including multiple myeloma, is the use of therapeutic antibodies, such as an anti-SLAMF7 antibody. However, existing methods for measuring M-protein are unable to distinguish between M-protein indicative of a plasma cell disorder, e.g., multiple myeloma, and therapeutic antibodies that remain in the serum of recently treated subjects. As a result, subjects are errantly classified as having positive M-protein levels even when no measurable M-protein remains. These false positives can lead to more invasive tests, such as bone marrow biopsy, to confirm the results or additional treatment that may not be necessary. The methods disclosed herein allow for the differentiation of M-protein indicative of disease and therapeutic antibodies, reducing the incidence of false positives.

In some aspects, the methods disclosed herein allow for earlier detection of M proteins in a sample obtained from a subject as compared to a standard method of measuring M proteins. In some aspects, the methods disclosed herein allow for earlier detection of M proteins in a sample obtained from a subject as compared to an SPEP assay. In some aspects, the methods disclosed herein allow for earlier detection of M proteins in a sample obtained from a subject as compared to an SIFE assay. In some aspects, the methods disclosed herein allow for earlier detection of M proteins in a sample obtained from a subject as compared to measuring sFLC ratio using standard methods. In some aspects, the methods disclosed herein allow for detection of M proteins at least about 10% earlier, at least about 20% earlier, at least about 25% earlier, at least about 30% earlier, at least about 40% earlier, at least about 50% earlier, at least about 60% earlier, at least about 70% earlier, at least about 80% earlier, at least about 90% earlier, at least about 95% earlier as compared to the standard method. In some aspects, the methods disclosed herein allow for detection of M proteins at least about 1 cycle earlier, at least about 2 cycles earlier, at least about 3 cycles earlier, at least about 4 cycles earlier, at least about 5 cycles earlier, at least about 6 cycles earlier, at least about 7 cycles earlier, at least about 8 cycles earlier, at least about 9 cycles earlier, at least about 10 cycles earlier, at least about 15 cycles earlier, at least about 20 cycles earlier, at least about 25 cycles earlier, at least about 30 cycles earlier than the standard method. In some aspects, the methods disclosed herein allow for detection of M proteins at least about 10 cycles earlier than the standard method.

A. Plasma Cell Disorders

Certain aspects of the present disclosure are directed to methods of diagnosing, monitoring, and/or treating a plasma cell disorder. Plasma cell disorders include a spectrum of progressively more severe monoclonal gammopathies in which a clone or multiple clones of pre-malignant or malignant plasma cells (sometimes in association with lympho-plasmacytoid cells or B lymphocytes) over-produce and secrete into the blood stream M-protein. Nonexclusive examples of plasma cell disorders include monoclonal gammopathy of undetermined significance (MGUS) and hematological malignancies, including, multiple myeloma, Waldenström's macroglobulinemia, and other B cell-associated neoplasm.

In certain aspects of the present disclosure, the plasma cell disease is MGUS. MGUS is an asymptomatic premalignant stage of clonal plasma cell proliferation. MGUS is present in approximately 3-5% of the population above the age of 50. Approximately 1% of subjects having MGUS progress to multiple myeloma each year.

In certain aspects of the present disclosure, the plasma cell disorder is multiple myeloma. Multiple myeloma (MM) is a clonal plasma cell malignancy that accounts for 10-15% of all hematologic cancers. MM is characterized by uncontrolled proliferation of monoclonal plasma cells in the bone marrow, leading to production of nonfunctional intact immunoglobulins or immunoglobulin chains (e.g., M-proteins) and end organ damage.

MM usually evolves from MGUS, at a rate of approximately 1% per year. An intermediate asymptomatic, more advanced premalignant stage, referred to as "smoldering multiple myeloma" (SMM), also occurs in some patients prior to progression to MM.

Standard diagnosis of MM includes thorough history-taking, physical examination, and various laboratory tests including analysis of a 24-hour urine sample, a bone-marrow biopsy, and skeletal radiography. MM is characterized by the presence of monoclonal protein (M-protein) in a patient's serum and urine along with marrow plasmacytosis and myeloma-related end-organ damage. In MM patients, the serum level of M-protein is at least 30 g/L. MGUS and SMM are also characterized by the presence of M-protein in the serum. In SMM patients, like MM, M-protein is found in serum at a concentration of at least 30 g/L. SMM patients, however, do not have M-protein in their urine and do not display end-organ damage. MGUS is characterized by a M-protein serum concentration less than 30 g/L.

Treatment for MM is based on an individual patient's age, comorbidities, and risk profile. Recent developments in MM treatments have raised the 5-year survival rate to approximately 50%. Most patients, however, will eventually suffer a fatal relapse. The standard treatment for most patients under 70 is autologous stem cell transplantation. Patients typically receive 2-6 cycles of induction treatment, aiming to achieve a complete or near complete response, prior to receiving their transplant. Following the transplant, patients typically receive maintenance thalidomide or lenalidomide, with or without prednisone or dexamethasone, for 12 months. If a patient is ineligible for transplant, treatment usually consists of a combination of steroids, a cytotoxic agent (such as cyclophosphamide), and thalidomide, lenalidomide, or bortezomib.

While recent developments have increased the 5-year survival rate, these advancements have not increased survival rates in patients with high-risk MM or relapse MM patients. The median survival of patients with high-risk MM is only two to three years. While there have been few advancements in treatments for high-risk and relapse MM patients, one advancement is the use of immunotherapy targeting tumor cell surface antigens.

Signaling lymphocyte activation molecule (SLAM) family receptors are one target for immunotherapeutic MM treatments. SLAM receptors have been implicated in the pathogenesis of different diseases such as cancer, specifically MM. Elotuzumab is an IgG1 humanized antibody against SLAMF7 that is used as an immunotherapeutic MM treatment. Combinations of elotuzumab, lenalidomide, and dexamethasone display significant anti-MM activity. Use of elotuzumab in combination with lenalidomide and dexamethasone has been approved in the treatment of relapse and refractory MM. The combination of elotuzumab, lenalidomide, and dexamethasone is also being studied for use in newly diagnosed MM patients who are not candidates for high-dose therapy and autologous stem cell transplantation due to either comorbidities or advanced age.

The methods described herein can be used to measure M-proteins in samples obtained from subjects having any known type of plasma cell disease. In certain aspects, the plasma cell disease is a MM. In some aspects, the MM comprises a light chain MM. In some aspects, the MM comprises a plasma cell leukemia. In some aspects, the plasma cell leukemia comprises a primary plasma cell leukemia or a secondary plasma cell leukemia. In some aspects, the plasma cell disease is an MGUS. In some aspects, the plasma cell disease is an SMM.

In some aspects, the biological sample is collected from a subject that has a plasma cell disease, e.g., MM. In some aspects, the subject was previously diagnosed with a plasma cell disease, e.g., MM. In some aspects, the subject is in remission. In some aspects, the subject is relapsed or refractory. In some aspects, the subject is relapsed or refractory following a standard therapy for the treatment of the plasma cell disease, e.g., MM. In some aspects, the subject has a residual disease, wherein the subject was previously diagnosed with a plasma cell disease, e.g., MM.

In some aspects, the subject received a previous therapy to treat a plasma cell disorder, e.g., MM. In some aspects, the previous therapy was a standard of care therapy for the treatment of the plasma cell disorder, e.g., MM. In some aspects, the previous therapy comprises an autologous stem cell transplantation. In some aspects, the previous therapy comprises a chimeric antigen receptor T cell (CAR-T cell) therapy. In some aspects, the previous therapy comprises a steroid, a cytotoxic agent (e.g., a chemotherapy, e.g., cyclophosphamide), an immunomodulatory (e.g., thalidomide, lenalidomide, pomalidomide), bortezomib, or any combination thereof. In some aspects, the prior therapy comprises an immunotherapy. In some aspects, the immunotherapy is any immunotherapy disclosed herein. In some aspects, the immunotherapy comprises an anti-SLAMF7 antibody or an antigen-binding portion thereof. In some aspects, the immunotherapy comprises elotuzumab.

In some aspects, the biological sample is tissue or fluid sample obtained from a subject. In some aspects, the biological sample is selected from a blood, blood plasma, serum, or urine sample. In certain aspects, the biological sample is a serum sample. In certain aspects, the biological sample is a urine sample. In some aspects, the biological sample is a bone marrow biopsy. The biological sample can be collected by any methods known in the art.

B. Methods of Diagnosing Disease

Certain aspects of the present disclosure are directed to methods of diagnosing a plasma cell disorder in a subject. Measurement of M-protein is necessary for the diagnosis of plasma cell disorders, such as multiple myeloma. However, current methods, including gel electrophoresis-based M-protein assays, have poor sensitivity and specificity and are not quantitative at M-protein concentrations below 10 mg/mL due to the presence of immunoglobulins or other serum proteins that co-migrate with M-protein. In addition, these electrophoresis-based assays have very limited utility for multiple myeloma patients who secrete free light chains (FLCs). Serum FLCs are rapidly excreted to urine; therefore, FLC have been measured in urine using Urine Protein Electrophoresis (UPEP) and Urine ImmunoFixation Electrophoresis (UIFE) tests. In addition, SPEP and SIFE assays do not discriminate well between normal polyclonal immunoglobulins, referred to as uninvolved immunoglobulins, and disease-related monoclonal immunoglobulin. As a result, a complex testing algorithm is needed to diagnose and monitor multiple myeloma patients.

Some aspects of the present disclosure are directed to a method of diagnosing a plasma cell disorder in a subject, comprising measuring M protein in a biological sample obtained from the subject, wherein the M protein is measured by: (1) purifying immunoglobulins and free light chains in the biological sample by immunocapture, and (2) applying the purified immunoglobulins and free light chains to a liquid chromatography (LC) mass spectrometry (MS). In some aspects, the subject has one or more marker indicative of a plasma cell disorder. In some aspects, the subject has previously presented with one or more symptom of a plasma cell disorder, e.g., multiple myeloma, selected from bone pain (e.g., spine or chest), nausea, constipation, loss of appetite, mental fogginess or confusion, fatigue, frequent infections, weight loss, weakness or numbness in the legs, excessive thirst. In some aspects, the subject is identified as having a plasma cell disorder if the measure M-protein level is greater than a threshold level.

Certain aspects of the present disclosure are directed to methods of identifying a subject having a residual disease, e.g., a minimal residual disease, comprising measuring M-protein in a biological sample obtained from the subject, wherein the M-protein is measured by: (1) purifying immunoglobulins and free light chains in the biological sample by immunocapture, and (2) applying the purified immunoglobulins and free light chains to a liquid chromatography (LC) mass spectrometry (MS); wherein the subject was previously identified as having a plasma cell disorder.

A minimal residual disease (MRD) is the name given to small numbers of cancer cells that remain in the person during treatment, or after treatment when the patient is in remission (no symptoms or signs of disease). It is the major cause of relapse in cancer. In cancer treatment, MRD testing has several important roles: determining whether treatment has eradicated the cancer or whether traces remain, comparing the efficacy of different treatments, monitoring patient remission status as well as detecting recurrence of cancer, and choosing the treatment that will best meet those needs. In some aspects, the MRD is a plasma cell MRD.

In some aspects, the subject received at least one prior therapy for the treatment of the plasma cell disorder. In some aspects, the subject received at least two, at least three, at least four, at least five prior, at least six prior, at least seven prior, at least eight prior, at least nine prior, or at least ten prior therapies for the treatment of the plasma cell disorder. In some aspects, the subject received eight prior therapies for the treatment of the plasma cell disorder. In some aspects, the subject presents with no other markers indicative of residual disease. In some aspects, the subject is identified as having a residual disease if the measure M-protein level is greater than a threshold level.

In some aspects, the prior therapy comprises cyclophosphamide, doxorubicin, etoposide, liposomal doxorubicin, melphalan, vincristine, bortezomib, lenalidomide, carfilzomib, pomalidomide, panobinostat, thalidomide, lenalidomide, pomalidomide, stem cell transplant, a CAR-T cell therapy, or any combination thereof.

In some aspects, the prior therapy comprises cyclophosphamide. Cyclophosphamide (CP), also known as cytophosphane among other names, is a medication used as chemotherapy and to suppress the immune system. As chemotherapy it is used to treat lymphoma, multiple myeloma, leukemia, ovarian cancer, breast cancer, small cell lung cancer, neuroblastoma, and sarcoma. It is taken by mouth or injection into a vein.

In some aspects, the prior therapy comprises doxorubicin. Doxorubicin, sold under the trade names Adriamycin among others, is a chemotherapy medication used to treat cancer. This includes breast cancer, bladder cancer, Kaposi's sarcoma, lymphoma, and acute lymphocytic leukemia. It is often used together with other chemotherapy agents. Doxorubicin is given by injection into a vein.

In some aspects, the prior therapy comprises etoposide. Etoposide, sold under the brand name Etopophos among others, is a chemotherapy medication used for the treatments of a number of types of cancer. This includes testicular cancer, lung cancer, lymphoma, leukemia, neuroblastoma, and ovarian cancer. It is used by mouth or injection into a vein.

In some aspects, the prior therapy comprises melphalan. Melphalan, sold under the trade name Alkeran among others, is a chemotherapy medication used to treat multiple myeloma, ovarian cancer, AL amyloidosis, and occasionally malignant melanoma. The agent was first investigated as a possible drug for use in melanoma, it was not found to be effective. In 2016, it was approved in the U.S. for: use as a high-dose conditioning treatment prior to hematopoietic progenitor (stem) cell transplantation in multiple myeloma (MM) patients the palliative treatment of MM patients for whom oral therapy is not appropriate.

In some aspects, the prior therapy comprises vincristine. Vincristine, also known as leurocristine and marketed under the brandname Oncovin among others, is a chemotherapy medication used to treat a number of types of cancer. This includes acute lymphocytic leukemia, acute myeloid leukemia, Hodgkin's disease, neuroblastoma, and small cell lung cancer among others. Vincristine is delivered via intravenous infusion for use in various types of chemotherapy regimens. Its main uses are in non-Hodgkin's lymphoma as part of the chemotherapy regimen CHOP, Hodgkin's lymphoma as part of MOPP, COPP, BEACOPP, or the less popular Stanford V chemotherapy regimen in acute lymphoblastic leukemia (ALL), and in treatment for nephroblastoma. It is also used to induce remission in ALL with dexamethasone and L-Asparaginase, and in combination with prednisone to treat childhood leukemia. Vincristine is occasionally used as an immunosuppressant, for example, in treating thrombotic thrombocytopenic purpura (TTP) or chronic idiopathic thrombocytopenic purpura (ITP).

In some aspects, the prior therapy comprises bortezomib. Bortezomib, sold under the brand name Velcade among others, is an anti-cancer medication used to treat multiple myeloma and mantle cell lymphoma. This includes multiple myeloma in those who have and have not previously received treatment. It is generally used together with other medications. It is given by injection. Two open-label trials established the efficacy of bortezomib (with or without dexamethasone) on days 1, 4, 8, and 11 of a 21-day cycle for a maximum of eight cycles in heavily pretreated people with relapsed/refractory multiple myeloma. The phase III demonstrated the superiority of bortezomib over a high-dose dexamethasone regimen (e.g. median TTP 6.2 vs 3.5 months, and 1-year survival 80% vs 66%).

In some aspects, the prior therapy comprises lenalidomide. Lenalidomide, sold under the trade name Revlimid among others, is a medication used to treat multiple myeloma (MM) and myelodysplastic syndromes (MDS). For MM it is used after at least one other treatment and generally together with dexamethasone. It is a more potent molecular analog of thalidomide, which inhibits tumor angiogenesis, tumor secreted cytokines and tumor proliferation through the induction of apoptosis.

Lenalidomide is effective at inducing a complete or "very good partial" response as well as improving progression-free survival. Adverse events more common in people receiving lenalidomide for myeloma were neutropenia (a decrease in the white blood cell count), deep vein thrombosis, infections, and an increased risk of other hematological malignancies. The risk of second primary hematological malignancies does not outweigh the benefit of using lenalidomide in relapsed or refractory multiple myeloma.

In some aspects, the prior therapy comprises carfilzomib. Carfilzomib (marketed under the trade name Kyprolis, developed by Onyx Pharmaceuticals) is an anti-cancer drug acting as a selective proteasome inhibitor. Chemically, it is a tetrapeptide epoxyketone and an analog of epoxomicin. The U.S. Food and Drug Administration (FDA) approved it on 20 Jul. 2012 for use in patients with multiple myeloma who have received at least two prior therapies, including treatment with bortezomib and an immunomodulatory therapy (such as lenalidomide) and have demonstrated disease progression on or within 60 days of completion of the last therapy. Initial approval was based on response rate. Data demonstrating an Overall Survival (OS) benefit was later demonstrated in the ENDEAVOR trial and approved by the FDA.

In some aspects, the prior therapy comprises pomalidomide. Pomalidomide (INN; marketed as Pomalyst in the U.S. and Imnovid in the EU and Russia) is a derivative of thalidomide marketed by Celgene. It is anti-angiogenic and also acts as an immunomodulator. Pomalidomide was approved in February 2013 by the U.S. Food and Drug Administration (FDA) as a treatment for relapsed and refractory multiple myeloma. It has been approved for use in people who have received at least two prior therapies including lenalidomide and bortezomib and have demonstrated disease progression on or within 60 days of completion of the last therapy. It received a similar approval from the European Commission in August 2013.

In some aspects, the prior therapy comprises panobinostat. Panobinostat (trade name Farydak) is a drug by Novartis for the treatment of various cancers. It is a hydroxamic acid and acts as a non-selective histone deacetylase inhibitor (pan-HDAC inhibitor). On 23 Feb. 2015 it received FDA accelerated approval for use in patients with multiple myeloma, and on 28 Aug. 2015 it was approved by the European Medicines Agency for the same use.

In some aspects, the prior therapy comprises thalidomide. Thalidomide, sold under the brand name Thalomid, among others, is an immunomodulatory drug and the prototype of the thalidomide class of drugs. It is mainly used as a treatment of certain cancers (multiple myeloma) and of a complication of leprosy. It is on the World Health Organization's List of Essential Medicines, the safest and most effective medicines needed in a health system.

In some aspects, the prior therapy comprises hematopoietic stem cell transplantation. Hematopoietic stem cell transplantation (HSCT) (stem cell transplant) is the transplantation of multipotent hematopoietic stem cells, usually derived from bone marrow, peripheral blood, or umbilical cord blood. It may be autologous (the patient's own stem cells are used), allogeneic (the stem cells come from a donor) or syngeneic (from an identical twin). In certain aspects, the prior therapy comprises a chimeric antigen receptor T cell (CAR-T cell) therapy.

It is most often performed for patients with certain cancers of the blood or bone marrow, such as multiple myeloma or leukemia. In these cases, the recipient's immune system is usually destroyed with radiation or chemotherapy before the transplantation. Infection and graft-versus-host disease are major complications of allogeneic HSCT.

In some aspects, the level of M-protein measured in a biological sample is indicative of the type of plasma cell disorder that a subject is afflicted with. In some aspects, if a serum sample obtained from the subject is determined to have (as measured using any method disclosed herein) at least about 30 g/L of M-protein, the subject is identified as having a plasma cell disease, e.g., multiple myeloma. In some aspects, if a serum sample obtained from the subject is determined to have (as measured using any method disclosed herein) at least about 5 g/L to at least about 30 g/L of M-protein, the subject is identified as a candidate at risk of having a plasma cell disease, e.g., multiple myeloma. In some aspects, if a serum sample obtained from the subject has M-protein levels below the limits of detection, the subject is identified as not having a plasma cell disease, e.g., multiple myeloma.

C. Methods of Measuring Responsiveness to a Plasma Cell Disease Therapy

Measurement of M-protein is necessary not only for the diagnosis of patients, but also for monitoring of multiple myeloma patients undergoing treatment. However, multiple myeloma patients treated with therapeutic monoclonal antibodies, such as anti-SLAMF7 antibodies, have a potential drug interference when monitoring treatment response using existing Serum Protein Electrophoresis (SPEP) and Serum ImmunoFixation Electrophoresis (SIFE) assays. Current M-protein tests are incapable of monitoring patients in complete remission (CR), as any remaining M-protein indicates less than a complete response.

Certain aspects of the present disclosure are directed to methods of identifying a subject having a complete response to a therapy for the treatment of a plasma cell disorder, comprising measuring M protein in a biological sample obtained from the subject, wherein the M protein is measured by: (1) purifying immunoglobulins and free light chains in the biological sample by immunocapture, and (2) applying the purified immunoglobulins and free light chains to a liquid chromatography (LC) mass spectrometry (MS). In certain aspects, the methods disclosed herein are capable of differentiating between M-proteins and therapeutic antibodies.

In some aspects, the therapy for the treatment of a plasma cell disorder comprises cyclophosphamide, doxorubicin, etoposide, liposomal doxorubicin, melphalan, vincristine, bortezomib, lenalidomide, carfilzomib, pomalidomide, panobinostat, thalidomide, stem cell transplant, a CAR-T cell therapy or any combination thereof.

In some aspects, the therapy for the treatment of a plasma cell disorder comprises cyclophosphamide. In some aspects, the therapy for the treatment of a plasma cell disorder comprises doxorubicin. In some aspects, the therapy for the treatment of a plasma cell disorder comprises liposomal doxorubicin. In some aspects, the therapy for the treatment of a plasma cell disorder comprises etoposide. In some aspects, the therapy for the treatment of a plasma cell disorder comprises melphalan. In some aspects, the therapy for the treatment of a plasma cell disorder comprises vincristine. In some aspects, the therapy for the treatment of a plasma cell disorder comprises bortezomib. In some aspects, the therapy for the treatment of a plasma cell disorder comprises lenalidomide. In some aspects, the therapy for the treatment of a plasma cell disorder comprises carfilzomib. In some aspects, the therapy for the treatment of a plasma cell disorder comprises pomalidomide. In some aspects, the therapy for the treatment of a plasma cell disorder comprises panobinostat. In some aspects, the therapy for the treatment of a plasma cell disorder comprises thalidomide. In some aspects, the therapy for the treatment of a plasma cell disorder comprises hematopoietic stem cell transplantation. In some aspects, the therapy for the treatment of a plasma cell disorder comprises a chimeric antigen receptor T cell (CAR-T cell) therapy.

In some aspects, the therapy comprises administering an immunotherapy. In some aspects, the therapy comprises administering a therapeutic antibody. Any immunotherapy useful for the treatment of plasma cell disorders can be used in the methods disclosed herein. In some aspects, the therapy comprises administering an anti-SLAMF7 antibody. In some aspects, the immunotherapy comprises a checkpoint inhibitor. Any checkpoint inhibitor known in the art can be used in the methods disclosed herein. In some aspects, the checkpoint inhibitor is any reagent that blocks, inhibits, or reduces the activity of one or more checkpoint protein. In some aspects, the checkpoint protein is selected from the group consisting of PD-1, CTLA-4, LAG3, TIGIT, TIM3, NKG2a, OX40, ICOS, CD137, KIR, TGFβ, IL-10, IL-8, IL-2, CD96, VISTA, B7-H4, Fas ligand, CXCR4, mesothelin, CD27, GITR, and any combination thereof.

In some aspects, the immunotherapy comprises an antibody or antigen-binding portion thereof that specifically binds PD-1. Anti-PD-1 antibodies that are known in the art can be used in the presently described compositions and methods. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1\times10^{-7}$ M or less, as determined by surface plasmon resonance using a Biacore biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present disclosure include monoclonal antibodies that bind specifically to human PD-1 and exhibit at least one, in some aspects, at least five, of the preceding characteristics.

Other anti-PD-1 monoclonal antibodies have been described in, for example, U.S. Pat. Nos. 6,808,710, 7,488, 802, 8,168,757 and 8,354,509, US Publication No. 2016/ 0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some aspects, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/ 112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; also known as toripalimab; see Si-Yang Liu et al., *J. Hematol. Oncol.* 10:136 (2017)), BGB-A317 (Beigene; also known as Tislelizumab; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/ 040790), MGA012 (Macrogenics, see WO 2017/19846), BCD-100 (Biocad; Kaplon et al., *mAbs* 10(2):183-203 (2018), and IBI308 (Innovent; see WO 2017/024465, WO 2017/025016, WO 2017/132825, and WO 2017/133540).

In some aspects, the checkpoint inhibitor is an antibody or antigen-binding portion thereof that specifically binds CTLA-4. In some aspects, the checkpoint inhibitor is an antibody or antigen-binding portion thereof that specifically binds LAG3. In some aspects, the checkpoint inhibitor is an antibody or antigen-binding portion thereof that specifically binds TIGIT. In some aspects, the checkpoint inhibitor is an antibody or antigen-binding portion thereof that specifically binds TIM3. In some aspects, the checkpoint inhibitor is an antibody or antigen-binding portion thereof that specifically binds NKG2a. In some aspects, the checkpoint inhibitor is an antibody or antigen-binding portion thereof that specifically binds OX40. In some aspects, the checkpoint inhibitor is an antibody or antigen-binding portion thereof that specifically binds ICOS. In some aspects, the checkpoint inhibitor is an antibody or antigen-binding portion thereof that specifically binds CD137. In some aspects, the checkpoint inhibitor is an antibody or antigen-binding portion thereof that specifically binds KIR. In some aspects, the checkpoint inhibitor is an antibody or antigen-binding portion thereof that specifically binds TGFβ. In some aspects, the checkpoint inhibitor is an antibody or antigen-binding portion thereof that specifically binds IL-10. In some aspects, the checkpoint inhibitor is an antibody or antigen-binding portion thereof that specifically binds IL-8. In some aspects, the checkpoint inhibitor is an antibody or antigen-binding portion thereof that specifically binds IL-2. In some aspects, the checkpoint inhibitor is an antibody or antigen-binding portion thereof that specifically binds CD96. In some aspects, the checkpoint inhibitor is an antibody or antigen-binding portion thereof that specifically binds VISTA. In some aspects, the checkpoint inhibitor is an antibody or antigen-binding portion thereof that specifically binds B7-H4. In some aspects, the checkpoint inhibitor is an antibody or antigen-binding portion thereof that specifically binds Fas ligand. In some aspects, the checkpoint inhibitor is an antibody or antigen-binding portion thereof that specifically binds CXCR4. In some aspects, the checkpoint inhibitor is an antibody or antigen-binding portion thereof that specifically binds mesothelin. In some aspects, the checkpoint inhibitor is an antibody or antigen-binding portion thereof that specifically binds CD27. In some aspects, the checkpoint inhibitor is an antibody or antigen-binding portion thereof that specifically binds GITR.

In some aspects, the immunotherapy comprises an antibody or an antigen-binding portion thereof that specifically binds a protein selected from CD40, CD56, CD38, CD229, CD200, CD28, CD19, BCMA, CD317, CD70, and B2M. In some aspects, the immunotherapy comprises an antibody or an antigen-binding portion thereof that specifically binds CD40. In some aspects, the immunotherapy comprises an antibody or an antigen-binding portion thereof that specifically binds CD56. In some aspects, the immunotherapy comprises an antibody or an antigen-binding portion thereof that specifically binds CD38. In some aspects, the immunotherapy comprises an antibody or an antigen-binding portion thereof that specifically binds CD229. In some aspects, the immunotherapy comprises an antibody or an antigen-binding portion thereof that specifically binds CD200. In some aspects, the immunotherapy comprises an antibody or an antigen-binding portion thereof that specifically binds CD28. In some aspects, the immunotherapy comprises an antibody or an antigen-binding portion thereof that specifically binds CD19. In some aspects, the immunotherapy comprises an antibody or an antigen-binding portion thereof that specifically binds BCMA. In some aspects, the immunotherapy comprises an antibody or an antigen-binding portion thereof that specifically binds CD317. In some aspects, the immunotherapy comprises an antibody or an antigen-binding portion thereof that specifically binds CD70. In some aspects, the immunotherapy comprises an antibody or an antigen-binding portion thereof that specifically binds B2M.

In some aspects, the subject is administered a monotherapy, e.g., an anti-PD-1 monotherapy, e.g., wherein the subject is not administered one or more additional anti-cancer agent. In some aspects, the subject is administered a combination therapy, e.g., wherein the subject is administered a first checkpoint inhibitor, e.g., an anti-PD-1 antibody, and one or more additional anti-cancer agents. In certain aspects, the subject is administered a combination therapy comprising an anti-PD-1 antibody and an anti-CTLA-4 antibody.

In other aspects of the present disclosure, an anti-PD-L1 antibody is substituted for the anti-PD-1 antibody. In certain aspects, the methods comprise administering an anti-PD-L1 antibody to a subject. In some aspects, the subject is administered an anti-PD-L1 monotherapy. In some aspects, the subject is administered a combination therapy comprising an anti-PD-L1 antibody and a second anti-cancer agent, e.g., an anti-CTLA-4 antibody.

In some aspects, the antibody is a chimeric, humanized or human monoclonal antibody or a portion thereof.

In some aspects, the therapy is administered prior to the measuring. In some aspects the therapy is ongoing at the time of the measuring. In some aspects, the therapy is administered at least one day prior to the measuring. In some aspects, the therapy is administered at least two days, at least three days, at least four days, at least five days, at least six days, at least one week, at least two weeks, or at least one month prior to the measuring. In some aspects, the therapy is administered less than one week before the measuring. In some aspects, the therapy is administered less than six days, less than five days, less than four days, less than three days, or less than two days before the measuring.

D. Immunoglobulin Purification

In certain aspects of the present disclosure, immunoglobulins are purified from a biological sample prior to LC-MS analysis. Any method known in the art for purifying immunoglobulins can be used in the methods disclosed herein. In certain aspects, immunoglobulins are purified from a biological sample using a ligand-binding technique. Ligand-binding purification of immunoglobulins involves the use of a capture reagent that interacts with a target immunoglobulin to enrich or purify the target immunoglobulin. In the methods disclosed herein, the target immunoglobulin is M-protein, which can be a very diverse population of immunoglobulins, comprised of M-proteins can belong to IgG, IgA, IgM and/or IgD class immunoglobulins. Further, M-proteins can comprise intact immunoglobulin molecule and/or immunoglobulin fragments such as free light chains (FLCs) also known as Bence Jones proteins.

In some aspects, the capture reagent comprises an antibody or an antigen-binding fragment thereof. In some aspects, the capture reagent comprises one or more monoclonal antibody. In some aspects, the capture reagent comprises one or more polyclonal antibody. In some aspects, the capture reagent comprises one or more monoclonal antibody and one or more polyclonal antibody. In some aspects, the capture reagent comprises one or more nanobody. In some aspects, the capture reagent comprises an antigen, e.g., a polypeptide that is capable of being bound by a target immunoglobulin.

In some aspects, a single capture reagent is used to capture and purify the target immunoglobulins (e.g., M-proteins). In some aspects more than one capture reagent is used to purify the target immunoglobulins (e.g., M-proteins). In some aspects, several capture reagents are used to purify the target immunoglobulins (e.g., M-proteins). In some aspects, the capture reagent is specific to a target class of immunoglobulin. In some aspects, the capture reagent is specific to IgG class immunoglobulins. In some aspects, the capture reagent is specific to IgA class immunoglobulins. In some aspects, the capture reagent is specific to IgM class immunoglobulins. In some aspects, the capture reagent is specific to IgD class immunoglobulins.

In some aspects, the capture reagent is a generic capture reagent. A "generic capture reagent," as used herein, is a ligand or other binding agent that is capable of binding to more than one human immunoglobulin. In some aspects, the generic capture reagent is capable of binding to at least two classes of human immunoglobulins. In some aspects, the generic capture reagent is capable of binding to at least three classes of human immunoglobulins. In some aspects, the generic capture reagent is capable of binding to at least four classes of human immunoglobulins. In some aspects, the generic capture reagent is capable of binding to all known classes of human immunoglobulins. In some aspects, the generic capture reagent is capable of binding to IgG, IgA, IgM, and IgD class immunoglobulins. In some aspects, the generic capture reagent is capable of biding to both intact immunoglobulin molecules and immunoglobulin fragments (e.g., free light chains).

In certain aspects, the capture reagent comprises an antibody or an antigen-binding fragment thereof that specifically binds an immunoglobulin light chain. In some aspects, the capture reagent comprises an antibody or an antigen-binding fragment thereof that specifically binds an immunoglobulin light chain constant region. In some aspects, the capture reagent comprises an antibody or an antigen-binding fragment thereof that specifically binds an immunoglobulin lambda light chain ("an anti-lambda antibody"). Any anti-lambda antibody capable of specifically binding human lambda light chain known in the art can be used in the methods disclosed herein, including but not limited to anti-lambda antibodies disclosed herein. In some aspects, the capture reagent comprises an antibody or an antigen-binding fragment thereof that specifically binds an immunoglobulin kappa light chain ("an anti-kappa antibody"). Any anti-kappa antibody capable of specifically binding human kappa light chain known in the art can be used in the methods disclosed herein, including but not limited to anti-kappa antibodies disclosed herein. In some aspects, the capture reagent comprises an anti-lambda antibody and an anti-kappa antibody.

In some aspects, the ratio of anti-lambda antibody to anti-kappa antibody is about 1:1, about 1.5:1, about 2:1, about 2.5:1, about 3:1, about 3.5:1, about 4:1 about, about 4.5:1, about 5:1 about, about 6:1, about 7:1 about, about 8:1, about 9:1 about, or about 10:1. In some aspects, the ratio of anti-kappa antibody to anti-lambda antibody is about 1:1, about 1.5:1, about 2:1, about 2.5:1, about 3:1, about 3.5:1, about 4:1 about, about 4.5:1, about 5:1 about, about 6:1, about 7:1 about, about 8:1, about 9:1 about, or about 10:1. In some aspects, the ratio of anti-lambda antibody to anti-kappa antibody is about 1:1. In certain aspects, capture reagent is incorporated into an affinity matrix. In some aspects, the affinity matrix comprises CAPTURESELECT® nanobody resin (THERMOFISHER). In particular aspects, the affinity matrix comprises CAPTURESELECT® nanobody resin (THERMOFISHER), comprising a 1:1 ratio of anti-lambda antibody to anti-kappa antibody.

In some aspects of the present disclosure, the affinity reagent, e.g., the affinity matrix, is packaged into a column. In some aspects, the column is amenable to automation. Automation of the purification of M-proteins by the immunocapture methods disclosed herein has several advantages, including, but not limited to, assay throughput and improved assay reproducibility. In certain aspects, the column is a tip column. In certain aspects, the column is a PHYTIP column (PHYNEXUS). In certain aspects, the column has a capacity to load at least about 10 μg, at least about 15 μg, at least about 20 μg, at least about 25 μg, at least about 30 μg, at least about 35 μg, at least about 40 μg, at least about 45 μg, at least about 50 μg, at least about 55 μg, at least about 60 μg, at least about 65 μg, at least about 70 μg, at least about 75 μg, at least about 80 μg, at least about 85 μg, at least about 90 μg, at least about 95 μg, at least about 100 μg, or at least about 150 μg of immunoglobulins. In certain aspects, the column has a capacity to load at least about 10 μg, at least about 15 μg, at least about 20 μg, at least about 25 μg, at least about 30 μg, at least about 35 μg, at least about 40 μg, at least about 45 μg, at least about 50 μg, at least about 55 μg, at least about 60 μg, at least about 65 μg, at least about 70 μg, at least about 75 μg, or at least about 80 μg at least about 85 μg, at least about 90 μg, at least about 95 μg, at least about 100 μg, or at least about 150 μg of lambda immunoglobulins. In certain aspects, the column has a capacity to load at least about 10 μg, at least about 15 μg, at least about 20 μg, at least about 25 μg, at least about 30 μg, at least about 35 μg, at least about 40 μg, at least about 45 μg, at least about 50 μg, at least about 55 μg, at least about 60 μg, at least about 65 μg, at least about 70 μg, at least about 75 μg, or at least about 80 μg at least about 85 μg, at least about 90 μg, at least about 95 μg, at least about 100 μg, or at least about 150 μg of kappa immunoglobulins. In certain aspects, the column has a capacity to load at least about 40 μg of lambda and at least about 40 μg of kappa immunoglobulins.

In certain aspects, the column is loaded into a multichannel device. In some aspects, the multichannel device is a multichannel pipette. In some aspects, the multichannel device is a robotic device. In some aspects, the multichannel device is a robotic device capable of automation. In some aspects, the multichannel device is a Freedom EVO® platform. In some aspects, the Freedom EVO® platform is equipped with 96 channels.

In some aspects, the column is loaded onto a single channel device, e.g., a single channel pipette.

In some aspects, the purified immunoglobulins are further dissociated into light chains and heavy chains. In some aspects, the purified immunoglobulins are dissociated by chemical reduction. In some aspects, the purified immunoglobulins are contacted with a denaturing agent. In some aspects, the purified immunoglobulins are dissociated by contacting the purified immunoglobulins with a reducing agent selected from tris(2-carboxyethyl)phosphine (TCEP); TCEP-HCl and other TCEP salts; DTT (2,3 dihydroxybutane-1,4-dithiol), DTE (2,3 dihydroxybutane-1,4-dithiol); thioglycolates; sulfites; bisulfites; sulfides; bisulfides; 2-Mercaptoethanol; 2-Mercaptoethanol-HCl; Bond-Breaker TCEP Solution, Neutral pH; Cysteine-HCl; Guanidine-HCl; urea; or any combination thereof. In some aspects, the purified immunoglobulins are dissociated by contacting the purified immunoglobulins with TCEP.

In certain aspects, the purified immunoglobulins are reduced by incubation in a reducing agent, e.g., TCEP, at a final concentration of at least about 1 mM to at least about 100 mM of the reducing agent, e.g., TCEP. In some aspects, the purified immunoglobulins are reduced by incubation in a reducing agent, e.g., TCEP, at a final concentration of at least about 10 mM to at least about 100 mM, at least about 20 mM to at least about 100 mM, at least about 30 mM to at least about 100 mM, at least about 40 mM to at least about 100 mM, at least about 50 mM to at least about 100 mM, at least about 2 mM to at least about 30 mM, at least about 3 mM to at least about 30 mM, at least about 4 mM to at least about 30 mM, at least about 5 mM to at least about 30 mM, at least about 6 mM to at least about 30 mM, at least about 7 mM to at least about 30 mM, at least about 8 mM to at least about 30 mM, at least about 9 mM to at least about 30 mM, at least about 10 mM to at least about 30 mM, at least about 15 mM to at least about 30 mM, at least about 20 mM to at least about 30 mM, at least about 10 mM to at least about 20 mM, at least about 10 mM to at least about 20 mM, at least about 15 mM to at least about 25 mM, or at least about 15 mM to at least about 20 mM of the reducing agent, e.g., TCEP. In certain aspects, the purified immunoglobulins are reduced by incubation in a reducing agent, e.g., TCEP, at a final concentration of at least about 10 mM, at least about mM, at least about 11 mM, at least about 12 mM, at least about 13 mM, at least about 14 mM, at least about 15 mM, at least about 16 mM, at least about 17 mM, at least about 18 mM, at least about 19 mM, at least about 20 mM, at least about 21 mM, at least about 22 mM, at least about 23 mM, at least about 24 mM, at least about 25 mM, at least about 26 mM, at least about 27 mM, at least about 28 mM, at least about 29 mM, or at least about 30 mM of the reducing agent, e.g., TCEP. In certain aspects, the purified immunoglobulins are reduced by incubation in a reducing agent, e.g., TCEP, at a final concentration of at least about 20 mM of the reducing agent, e.g., TCEP.

In some aspects, the purified immunoglobulins are reduced by incubation in TCEP at least about 20° C. to at least about 30° C. In some aspects, the purified immunoglobulins are reduced by incubation in TCEP at least about 21° C. to at least about 29° C., at least about 22° C. to at least about 28° C., at least about 23° C. to at least about 27° C., or at least about 24° C. to at least about 26° C. In some aspects, the purified immunoglobulins are reduced by incubation in TCEP at least about 20° C., at least about 21° C., at least about 22° C., at least about 23° C., at least about 24° C., at least about 25° C., at least about 26° C., at least about 27° C., at least about 28° C., at least about 29° C., or at least about 30. In some aspects, the purified immunoglobulins are reduced by incubation in TCEP at about 20° C.

In some aspects, the purified immunoglobulins are reduced by incubation in TCEP for at least about 20 to at least about 30 minutes, at least about 21 to at least about 30 minutes, at least about 22 to at least about 30 minutes, at least about 23 to at least about 30 minutes, at least about 24 to at least about 30 minutes, at least about 25 to at least about 30 minutes, at least about 26 to at least about 30 minutes, at least about 27 to at least about 30 minutes, at least about 28 to at least about 30 minutes, at least about 29 to at least about 30 minutes, at least about 20 to at least about 29 minutes, at least about 20 to at least about 28 minutes, at least about 20 to at least about 27 minutes, at least about 20 to at least about 26 minutes, at least about 20 to at least about 25 minutes, at least about 20 to at least about 24 minutes, at least about 20 to at least about 23 minutes, at least about 20 to at least about 22 minutes, at least about 20 to at least about 21 minutes, at least about 21 to at least about 29 minutes, at least about 22 to at least about 28 minutes, at least about 23 to at least about 27 minutes, or at least about 24 to at least about 26 minutes. The eluted samples were reduced immediately by adding 100 mM buffered TCEP solution to the final concentration of 20 mM followed by incubation at 25° C. for 30 min.

In some aspects, the purified immunoglobulins are reduced immediately after purification. In some aspects, the purified proteins are stored for a period of time prior to reduction.

E. Liquid Chromatography-Mass Spectrometry (LC-MS)

Mass spectrometry (MS) is a means of performing both qualitative and quantitative analysis of small molecules, macro-molecules, and mixed mode bio-polymeric samples. MS has been successfully used in a variety of different applications, including drug discovery, synthetic reaction monitoring, and nano-particle characterization. MS provides full service of samples, and allows one to perform method development, validation, and test sample analysis.

MS systems useful in the present disclosure generally provide one or more of the following non-limiting capabilities: peptide/protein molecular weight determination; accurate mass analysis/molecular formula verification; purity analysis of samples using LC-UV-MS; accurate mass analysis of complex mixtures with flow injection or UPLC separation; quantitation of organic compounds in biological or environmental samples; oligonucleotide molecular weight determination; imaging by mass spectrometry; clinical pharmacology and rapid pharmacokinetic (PK) analysis; or any combination thereof.

There are many different types of high resolution MS instruments used for the qualitative and quantitative analyses, any of which can be used in the methods disclosed herein. Non-limiting examples of MS instruments include Bruker Maxis or Impact systems, ABSciex TripleTOF 5600/6600, ABSciex X500R, Agilent 6545XT, Waters Xevo® G2 TOF or any other model.

Certain aspects of the present disclosure are directed to methods of measuring M-proteins in a biological sample by applying the sample to a liquid chromatography (LC) followed by MS. The combined technique between MS and LC is commonly known as LC-MS. The combination of LC and MS reduces experimental error and improves accuracy. In some aspects, the LC of the LC-MS comprises a high performance LC (HPLC). In some aspects, immunoglobulins are first purified by immunocapture, then the purified immunoglobulins are dissociated by chemical reduction, and then the purified, dissociated immunoglobulins are applied to a LC-MS. In some aspects, purified, dissociated immunoglobulins are applied to a LC-MS.

LC-MS provides a means of separating mixtures in accordance with their physical and chemical properties, then identifying the components within each peak and detecting based on their mass spectrum. In some aspects, the flow rates used in LC-MS are less than those used typically used for HPLC. Holding flow rates lower than HPLC can increase the likelihood of complete ionization and maintain the detection sensitivity of the MS, which starts to decrease beyond 200 μL/min. In some aspects, the column used in LC-MS is smaller than a column typically used for HPLC to accommodate the smaller solvent flow rates and sample volumes. In some aspects, a syringe pump is used in the LC-MS. Syringe pumps allow very accurate delivery even at low flow rates.

In certain aspects, the LC-MS comprises an Acquity UPLC H-Class Plus Bio System. The Acquity UPLC H-Class Plus Bio System provides high resolution, high sensitivity separations typically expected from UPLC technology. In addition, this system allows for flexibility and ruggedness to run all the chromatographic modes required, including by not limited to size exclusion (SEC) or reversed-phase (RP). This system further supports all existing HPLC, UHPLC, and UPLC methods. The Acquity UPLC H-Class Plus Bio System includes a bio-inert flow path made of non-stainless-steel materials. This allows keeps large molecules intact and on the move, for better sample recovery and no carryover.

In some aspects, the LC-MS comprises an LC column. In some aspects, the LC column is a C3 column. In some aspects, the LC column is a C4 column. Examples of C4 columns useful in the present disclosure include but are not limited to Acquity Protein BEH C4 300 Å, 1.7 μm, 2.1 mm×100 mm (Waters Corporation, MA);)(Bridge OBD Prep Column Reversed-Phase 5 μm (Waters Corporation), Aeris WIDEPORE 3.6u C4 (Phenomenex); ZORBAX SB-C3, 80 Å, 5 μm (Agilent); and Poroshell 300SB-C3 (Agilent). In certain aspects, the LC-MS comprises an Acquity UPLC H-Class Plus Bio System equipped with a C4 column. In some aspects, a sample is injected onto the column, e.g., the C4 column, with a column temperature set to about 70° C. to about 90° C., about 70° C. to about 85° C., about 70° C. to about 80° C., about 70° C. to about 75° C., about 75° C. to about 90° C., about 75° C. to about 85° C., about 75° C. to about 80° C., about 80° C. to about 90° C., or about 85° C. to about 90° C. In some aspects, the column temperature is set to about 75° C. to about 85° C. In some aspects, the column temperature is set to about 75° C. to about 80° C. In some aspects, the column temperature is set to about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., or about 90° C. In some aspects, a sample is injected onto the column, e.g., the C4 column, with a column temperature set to about 75° C. In some aspects, a sample is injected onto the column, e.g., the C4 column, with a column temperature set to about 76° C. In some aspects, a sample is injected onto the column, e.g., the C4 column, with a column temperature set to about 77° C. In some aspects, a sample is injected onto the column, e.g., the C4 column, with a column temperature set to about 78° C. In some aspects, a sample is injected onto the column, e.g., the C4 column, with a column temperature set to about 79° C. In some aspects, a sample is injected onto the column, e.g., the C4 column, with a column temperature set to about 80° C.

In some aspects, the mobile phase comprises a mobile phase A and a mobile phase B. In some aspects, the mobile phase A comprises about 0.01% to about 1.0%, about 0.02% to about 0.9%, about 0.03% to about 0.8%, about 0.04% to about 0.7%, about 0.05% to about 0.6%, about 0.06% to about 0.5%, about 0.07% to about 0.4%, about 0.08% to about 0.3%, about 0.09% to about 0.2%, about 0.1% to about 0.2%, about 0.01% to about 0.2%, about 0.02% to about 0.2%, about 0.03% to about 0.2%, about 0.04% to about 0.2%, about 0.05% to about 0.2%, about 0.06% to about 0.2%, about 0.07% to about 0.2%, about 0.08% to about 0.2%, about 0.09% to about 0.2%, about 0.01% to about 0.19%, about 0.02% to about 0.18%, about 0.03% to about 0.17%, about 0.04% to about 0.16%, about 0.05% to about 0.15%, about 0.06% to about 0.14%, about 0.07% to about 0.18%, about 0.08% to about 0.12%, about 0.09% to about 0.11%, about 0.05% to about 0.1%, or about 0.1% to about 0.15% formic acid (FA) in water. In some aspects, the mobile phase A comprises about 0.05% to about 0.15% FA in water. In some aspects, the mobile phase A comprises about 0.05%, about 0.06%, about 0.07%, about 0.08%, about 0.09%, about 0.10%, about 0.11%, about 0.12%, about 0.13%, about 0.14%, or about 0.15% FA in water. In some aspects, the mobile phase A comprises about 0.1% FA in water.

In some aspects, the mobile phase B comprises about 0.01% to about 1.0%, about 0.02% to about 0.9%, about 0.03% to about 0.8%, about 0.04% to about 0.7%, about 0.05% to about 0.6%, about 0.06% to about 0.5%, about 0.07% to about 0.4%, about 0.08% to about 0.3%, about 0.09% to about 0.2%, about 0.1% to about 0.2%, about 0.01% to about 0.2%, about 0.02% to about 0.2%, about 0.03% to about 0.2%, about 0.04% to about 0.2%, about 0.05% to about 0.2%, about 0.06% to about 0.2%, about 0.07% to about 0.2%, about 0.08% to about 0.2%, about 0.09% to about 0.2%, about 0.01% to about 0.19%, about 0.02% to about 0.18%, about 0.03% to about 0.17%, about 0.04% to about 0.16%, about 0.05% to about 0.15%, about 0.06% to about 0.14%, about 0.07% to about 0.18%, about 0.08% to about 0.12%, about 0.09% to about 0.11%, about 0.05% to about 0.1%, or about 0.1% to about 0.15% formic acid (FA) in acetonitrile. In some aspects, the mobile phase B comprises about 0.05% to about 0.15% FA in acetonitrile. In some aspects, the mobile phase B comprises about 0.05%, about 0.06%, about 0.07%, about 0.08%, about 0.09%, about 0.10%, about 0.11%, about 0.12%, about 0.13%, about 0.14%, or about 0.15% FA in acetonitrile. In some aspects, the mobile phase B comprises about 0.1% FA in acetonitrile.

In some aspects, a gradient separation program is used as following: 0-1.0 min 10% mobile phase B; 1.1-3.0 min 10-33% mobile phase B 3.0-10.0 min 33-40% mobile phase B; 10.1-10.5 min 40-90% mobile phase B; 10.5-13.0 min hold at 90% mobile phase B; 13.0-15.0 min 90-10% mobile phase B; and run stopped at 15.0 min. A gradient separation program allows a user to set up the time and delivery amount of one or more mobile phase, to run with desired setups, and to end the analysis properly.

In some aspects, the flow rate (i.e., the amount (volume) of mobile phase(s) delivered by the instrument per minute) is set at about 0.025 mL/min to about 1.0 mL/min, about 0.05 mL/min to about 1.0 mL/min, about 0.075 mL/min to about 1.0 mL/min, about 0.025 mL/min to about 0.9 mL/min, about 0.025 mL/min to about 0.8 mL/min, about 0.025 mL/min to about 0.7 mL/min, about 0.025 mL/min to about 0.6 mL/min, about 0.025 mL/min to about 0.5 mL/min, about 0.1 mL/min to about 0.9 mL/min, 0.1 mL/min to about 0.8 mL/min, 0.1 mL/min to about 0.7 mL/min, 0.1 mL/min to about 0.6 mL/min, 0.1 mL/min to about 0.5 mL/min, 0.1 mL/min to about 0.4 mL/min, 0.1 mL/min to about 0.3 mL/min, 0.2 mL/min to about 0.9 mL/min, 0.2 mL/min to about 0.8 mL/min, 0.2 mL/min to about 0.7 mL/min, 0.2 mL/min to about 0.6 mL/min, 0.2 mL/min to about 0.5 mL/min, 0.2 mL/min to about 0.4 mL/min, 0.2 mL/min to about 0.3 mL/min, 0.3 mL/min to about 0.9 mL/min, 0.3 mL/min to about 0.8 mL/min, 0.3 mL/min to about 0.7 mL/min, 0.3 mL/min to about 0.6 mL/min, 0.3 mL/min to about 0.5 mL/min, or 0.3 mL/min to about 0.4 mL/min. In some aspects, the flow rate is set to about 0.1 mL/min to 0.5 mL/min. In some aspects, the flow rate is set at about 0.025 mL/min, about 0.05 mL/min, about 0.075 mL/min, about 0.1 mL/min, about 0.2 mL/min, about 0.25 mL/min, about 0.26 mL/min, about 0.27 mL/min, about 0.28 mL/min, about 0.29 mL/min, about 0.30 mL/min, about 0.31 mL/min, about 0.32 mL/min, about 0.33 mL/min, about 0.34 mL/min, or about 0.35 mL/min. In some aspects, the flow rate is set at about 0.3 mL/min.

In some aspects, the injection volume (i.e., the amount (volume) of sample injected to the instrument for each run) is about 1.0 μL to about 3.0 μL, about 1.0 μL to about 2.5 μL, about 1.0 μL to about 2.0 μL, about 1.0 μL to about 1.5 μL, about 1.5 μL to about 3.0 μL, about 2.0 μL to about 3.0 μL, about 2.5 μL to about 3.0 μL, or about 1.5 μL to about 2.5 μL. In some aspects, the injection volume is about 1.5 μL to about 2.5 μL. In some aspects, the injection volume is about 1.0 μL, about 1.5 μL, about 2.0 μL, about 2.5 μL, or about 3.0 μL. In some aspects, the injection volume is about 2.0 μL.

In some aspects, the LC is on-line with an MS. In some aspects, immunoglobulins are analyzed directly by MS after separation on a high performance liquid chromatography column (HPLC). In some aspects, the MS comprises a time-of-flight MS high-resolution instrument. In some aspects, the MS comprises a time-of-flight MS. In some aspects, the MS comprises a laser desorption ionization (MALDI) MS. In certain aspects, the MS comprises a MALDI TOF MS. In particular aspects, the MS comprises a Maxis 4G Q-TOF (a.k.a. UHR) instrument. In some aspects, the MS does not comprise a MALDI MS. In some aspects, the MS does not comprise a microflow MS. In some aspects, the Maxis 4G Q-TOF comprises a standard Electrospray (ESI) Apollo-source (Bruker Daltonics, Hamburg, Germany). In some aspects, the instrument is calibrated before each run, e.g., by infusing ESI-L low concentration tuning mix (Agilent Technologies, CA). In some aspects, each 15-minute run is segmented as follows: a waste segment, a source segment, and an additional waste segment. In some aspects, each 15-minute run is segmented as follows: about 3 min to waste, followed by about 7 min to source, and the last about 5 min to waste.

In some aspects, the capillary voltage (i.e., the voltage applied to the electrospray) is set at about 4000 V to about 6000 V, about 4000 V to about 5900 V, about 4000 V to about 5800 V, about 4000 V to about 5700 V, 4000 V to about 5600 V, 4000 V to about 5500 V, 4000 V to about 5400 V, 4000 V to about 5300 V, 4000 V to about 5200 V, 4000 V to about 5100 V, 4000 V to about 5000 V, 4000 V to about 4900 V, 4000 V to about 4800 V, 4000 V to about 4700 V, about 4000 V to about 4600 V, about 4000 V to about 4500 V, about 4000 V to about 4400 V, about 4000 V to about 4300 V, about 4000 V to about 4200 V, about 4000 V to about 4100 V, about 4100 V to about 5000 V, about 4200 V to about 5000 V, about 4300 V to about 5000 V, about 4400 V to about 5000 V, about 4500 V to about 5000 V, about 4600 V to about 5000 V, about 4700 V to about 5000 V, about 4800 V to about 5000 V, about 4900 V to about 5000 V, about 4100 V to about 4900 V, about 4200 V to about 4800 V, about 4300 V to about 4700 V, or about 4400 V to about 4600 V. In some aspects, the capillary voltage is set at about 4000 V, about 4100 V, about 4200 V, about 4300 V, about 4400 V, about 4500 V, 4600 V, about 4700 V, about 4800 V, about 4900 V, or about 5000 V. In some aspects, the capillary voltage is set at about 4500 V.

In some aspects, the nebulizer (i.e., the apparatus that converts a liquid into a fine mist) is set at about 1.0 bar to about 2.2 bar, about 1.0 bar to about 2.1 bar, about 1.0 bar to about 2.0 bar, about 1.0 bar to about 1.9 bar, about 1.0 bar to about 1.8 bar, about 1.0 bar to about 1.7 bar, about 1.0 bar to about 1.6 bar, about 1.0 bar to about 1.5 bar, about 1.0 bar to about 1.4 bar, about 1.0 bar to about 1.3 bar, about 1.0 bar to about 1.2 bar, about 1.0 bar to about 1.1 bar, about 1.0 bar to about 2.2 bar, about 1.1 bar to about 2.2 bar, about 1.2 bar to about 2.2 bar, about 1.3 bar to about 2.2 bar, about 1.4 bar to about 2.2 bar, about 1.5 bar to about 2.2 bar, about 1.6 bar to about 2.2 bar, about 1.7 bar to about 2.2 bar, about 1.8 bar to about 2.2 bar, about 1.9 bar to about 2.2 bar, about 2.0 bar to about 2.2 bar, about 2.1 bar to about 2.2 bar, about 1.1 bar to about 2.1 bar, about 1.2 bar to about 2.0 bar, about 1.3 bar to about 1.9 bar, about 1.4 bar to about 1.8 bar, about 1.5 bar to about 1.7 bar, or about 1.5 bar to about 2.0 bar. In some aspects, the nebulizer is set at about 1.0 bar, about 1.1 bar, about 1.2 bar, about 1.3 bar, about 1.4 bar, about 1.5 bar, about 1.6 bar, about 1.7 bar, about 1.8 bar, about 1.9 bar, about 2.0 bar, about 2.1 bar, or about 2.2 bar. In some aspects, the nebulizer is set at about 1.6 bar.

In some aspects, the dry gas (i.e., high grade, low moisture gas) is set at about 7.5 L/min to about 9.5 L/min, about 7.6 L/min to about 9.5 L/min, about 7.7 L/min to about 9.5 L/min, about 7.8 L/min to about 9.5 L/min, about 7.9 L/min to about 9.5 L/min, about 8.0 L/min to about 9.5 L/min, about 8.1 L/min to about 9.5 L/min, about 8.2 L/min to about 9.5 L/min, about 8.3 L/min to about 9.5 L/min, about 8.4 L/min to about 9.5 L/min, about 8.5 L/min to about 9.5 L/min, about 8.6 L/min to about 9.5 L/min, about 8.7 L/min to about 9.5 L/min, about 8.8 L/min to about 9.5 L/min, about 8.9 L/min to about 9.5 L/min, about 9.0 L/min to about 9.5 L/min, about 9.1 L/min to about 9.5 L/min, about 9.2 L/min to about 9.5 L/min, about 9.3 L/min to about 9.5 L/min, about 9.4 L/min to about 9.5 L/min, at about 7.5 L/min to about 9.4 L/min, at about 7.5 L/min to about 9.3 L/min, at about 7.5 L/min to about 9.2 L/min, at about 7.5 L/min to about 9.1 L/min, at about 7.5 L/min to about 9.0 L/min, at about 7.5 L/min to about 8.9 L/min, at about 7.5 L/min to about 8.8 L/min, at about 7.5 L/min to about 8.7 L/min, at about 7.5 L/min to about 8.6 L/min, at about 7.5 L/min to about 8.5 L/min, at about 7.5 L/min to about 8.4 L/min, at about 7.5 L/min to about 8.3 L/min, at about 7.5 L/min to about 8.2 L/min, at about 7.5 L/min to about 8.1 L/min, at about 7.5 L/min to about 8.0, at about 7.5 L/min to about 7.9 L/min, at about 7.5 L/min to about 7.8 L/min, at about 7.5 L/min to about 7.7 L/min, at about 7.5 L/min to about 7.6 L/min, about 7.6 L/min to about 9.4 L/min, about 7.7 L/min to about 9.3 L/min, about 7.8 L/min to about 9.2 L/min, about 7.9 L/min to about 9.1 L/min, about 8.0 L/min to about 9.0 L/min, about 8.1 L/min to about 8.9 L/min, about 8.2 L/min to about 8.8 L/min, about 8.3 L/min to about 8.7 L/min, or about 8.4 L/min to about 8.6 L/min. In some aspects, the dry gas is set at about 8.0 L/min, about 8.1 L/min, about 8.2 L/min, about 8.3 L/min, about 8.4 L/min, about 8.5 L/min, about 8.6 L/min, about 8.7 L/min, about 8.8 L/min, about 8.9 L/min, or about 9.0 L/min. In some aspects, the dry gas is set at about 8.5 L/min.

In some aspects, the dry temperature (i.e., the air temperature shielded from radiation and moisture) is set at about 175° C. to about 225° C., about 180° C. to about 225° C., about 185° C. to about 225° C., about 190° C. to about 225° C., about 195° C. to about 225° C., about 200° C. to about 225° C., about 205° C. to about 225° C., about 210° C. to about 225° C., about 215° C. to about 225° C., about 220° C. to about 225° C., about 175° C. to about 220° C., about 175° C. to about 215° C., about 175° C. to about 210° C., about 175° C. to about 205° C., about 175° C. to about 200° C., about 175° C. to about 195° C., about 175° C. to about 190° C., about 175° C. to about 185° C., about 175° C. to about 180° C., about 180° C. to about 220° C., about 185° C. to about 215° C., about 190° C. to about 210° C., or about 195° C. to about 205° C. In some aspects, the dry temperature is set at about 175° C., about 180° C., about 185° C., about 190° C., about 195° C., about 200° C., about 205° C., about 210° C., about 215° C., about 220° C., or about 225° C. In some aspects, the dry temperature is set at about 200° C.

In some aspects, the transfer funnel radio frequency (RF) and/or multipole RF parameters are set at about 350 Vpp to about 450 Vpp, about 360 Vpp to about 450 Vpp, about 370 Vpp to about 450 Vpp, about 380 Vpp to about 450 Vpp, about 390 Vpp to about 450 Vpp, about 400 Vpp to about 450 Vpp, about 410 Vpp to about 450 Vpp, about 420 Vpp to about 450 Vpp, about 430 Vpp to about 450 Vpp, about 440 Vpp to about 450 Vpp, about 350 Vpp to about 440 Vpp, about 350 Vpp to about 435 Vpp, about 350 Vpp to about 430 Vpp, about 350 Vpp to about 420 Vpp, about 350 Vpp to about 410 Vpp, about 350 Vpp to about 400 Vpp, about 350 Vpp to about 390 Vpp, about 350 Vpp to about 380 Vpp, about 350 Vpp to about 370 Vpp, about 350 Vpp to about 360 Vpp, about 360 Vpp to about 440 Vpp, about 370 Vpp to about 430 Vpp, about 380 Vpp to about 420 Vpp, or about 390 Vpp to about 410 Vpp. In some aspects, the transfer funnel RF and/or multipole RF parameters are set at about 350 Vpp, about 360 Vpp, about 370 Vpp, about 380 Vpp, about 390 Vpp, about 400 Vpp, about 410 Vpp, about 420 Vpp, about 430 Vpp, about 440 Vpp, or about 450 Vpp. In some aspects, the transfer funnel RF and/or multipole RF parameters are set at about 400 Vpp.

In some aspects, in-source collision induced dissociation (isCID) energy is applied. In some aspects, no isCID energy is applied. isCID is a mass spectrometry technique to induce fragmentation of selected ions in the gas phase. The selected ions (typically molecular ions or protonated molecules) are usually accelerated by applying an electrical potential to increase the ion kinetic energy and then allowed to collide with neutral molecules (e.g., helium, nitrogen, or argon). In the collision, some of the kinetic energy is converted into internal energy which results in bond breakage and the fragmentation of the molecular ion into smaller fragments.

In some aspects, the ion cooler transfer time is about 50 µs to about 150 µs, about 60 µs to about 150 µs, about 70 µs to about 150 µs, about 80 µs to about 150 µs, about 90 µs to about 150 µs, about 100 µs to about 150 µs, about 110 µs to about 150 µs, about 120 µs to about 150 µs, about 130 µs to about 150 µs, about 140 µs to about 150 µs, about 50 µs to about 140 µs, about 50 µs to about 130 µs, about 50 µs to about 120 µs, about 50 µs to about 110 µs, about 50 µs to about 100 µs, about 50 µs to about 90 µs, about 50 µs to about 80 µs, about 50 µs to about 70 µs, about 50 µs to about 60 µs, about 60 µs to about 140 µs, about 70 µs to about 130 µs, about 80 µs to about 120 µs, or about 90 µs to about 110 µs. In some aspects, the ion cooler transfer time is about 50 µs, about 60 µs, about 70 µs, about 80 µs, about 90 µs, about 100 µs, about 110 µs, about 120 µs, about 130 µs, about 140 µs, or about 150 µs. In some aspects, the ion cooler transfer time is about 100 µs. Ion cooler transfer is a means of slowing down high energy ions during the analysis.

In some aspects, the ion cooler transfer has a prepulse storage of about 20 µs to about 30 µs, about 21 µs to about 30 µs, about 22 µs to about 30 µs, about 23 µs to about 30 µs, about 24 µs to about 30 µs, about 25 µs to about 30 µs, about 26 µs to about 30 µs, about 27 µs to about 30 µs, about 28 µs to about 30 µs, about 29 µs to about 30 µs, about 20 µs to about 29 µs, about 20 µs to about 28 µs, about 20 µs to about 27 µs, about 20 µs to about 26 µs, about 20 µs to about 25 µs, about 20 µs to about 24 µs, about 20 µs to about 23 µs, about 20 µs to about 22 µs, about 20 µs to about 21 µs, about 21 µs to about 29 µs, about 22 µs to about 28 µs, about 23 µs to about 27 µs, or about 24 µs to about 26 µs. In some aspects, the ion cooler transfer has a prepulse storage of about 20 µs, about 21 µs, about 22 µs, about 23 µs, about 24 µs, about 25 µs, about 26 µs, about 27 µs, about 28 µs, about 29 µs, or about 30 µs. In some aspects, the ion cooler transfer has a prepulse storage of about 25 µs.

In some aspects, TOF MS scans are acquired from m/z 700-2700 with an acquisition rate of about 1.0 Hz.

For the methods disclosed herein, any ESI Q-TOF mass spectrometer can be used. This includes, but is not limited to a Bruker Maxis, ABSciex TripleTOF 5600/6600, ABSciex X500R, Agilent 6545XT, Waters Xevo® G2 TOF spectrometer or any other model.

F. Methods of Treating

Some aspects of the present disclosure are directed to methods of treating a subject having a plasma cell disorder. Certain aspects of the present disclosure are directed to methods of treating a subject having a plasma cell disorder, comprising: measuring M-protein in a biological sample obtained from the subject using any method disclosed herein and administering to a subject identified as having M-protein, a therapeutically effective amount of an antibody or an antigen binding portion thereof that specifically binds SLAMF7 ("an anti-SLAMF7 antibody"). Other aspects of the present disclosure are directed to methods of treating a subject having a plasma cell disorder, comprising: (i) administering to the subject a therapeutically effective amount of an anti-SLAMF7 antibody; (ii) measuring M-protein in a biological sample obtained from the subject using any method disclosed herein; and (iii) administering to the subject an additional therapeutically effective amount of the anti-SLAMF7 antibody. Still other aspects of the present disclosure are directed to methods of identifying a subject suitable for an anti-SLAMF7 antibody therapy, comprising measuring M-proteins in a biological sample obtained from the subject using any method disclosed herein. In some aspects, the method further comprises administering to a subject identified as having M-protein a therapeutically effective amount of an anti-SLAMF7 antibody.

Any antibody or antigen-binding portion thereof that specifically binds human SLAMF7 can be used in the methods disclosed herein. In some aspects, the anti-SLAMF7 antibody cross-competes with elotuzumab for binding to human SLAMF7. In some aspects, the anti-SLAMF7 antibody binds the same epitope on human SLAMF7 as elotuzumab. In some aspects, the anti-SLAMF7 antibody binds an overlapping epitope on human SLAMF7 as elotuzumab. In some aspects, the anti-SLAMF7 antibody is a human antibody. In some aspects, the anti-SLAMF7 antibody is a humanized antibody. In some aspects, the anti-SLAMF7 antibody is a chimeric antibody. In certain aspects, the anti-SLAMF7 antibody is elotuzumab.

Elotuzumab (also referred to as BMS-901608 and HuLuc63) is a humanized monoclonal IgG1 antibody directed against SLAMF7 (also known as CS-1), a cell surface glycoprotein, which is highly and uniformly expressed in multiple myeloma (see U.S. Publication Nos. US 2006/024296, US 2010/168397, US 2009/246852, US 2009/238835, US 2012/064067, US 2012/070440, US 2012/064068, US 2012/064083, US 2012/064069, US 2014/065063, US 2016/002335, US 2005/025763, US 2009/238827, US 2008/124332, US 2011/165154, US 2016/206734, US 2008/152646, US 2014/322201, US 2016/137735, US 2017/342150, US 2008/095768, US 2011/206701, US 2013/052158, and US 2013/058921; and PCT Publication Nos. WO 2004/100898, WO 2005/102387, WO 2008/019376, WO 2008/019378, WO 2008/019379, WO 2010/051391, WO 2011/053321, and WO 2011/053322; each of which is incorporated by reference herein in its entirety). Elotuzumab induces significant antibody-dependent cellular cytotoxicity (ADCC) against primary multiple myeloma cells in the presence of peripheral lymphocytes (Tai et al., Blood, 112:1329-1337 (2008)). Elotuzumab is known to mediate ADCC through NK cells (van Rhee, F. et al., Mol. Cancer Ther., 8(9):2616-2624 (2009)). Results of three studies that evaluated the safety and efficacy of this drug administered alone (Zonder et al., Blood, 120(3):552-559 (2012)), in combination with bortezomib (Jakubowiak et al., J. Clin. Oncol., 30(16):1960-1965 (Jun. 1, 2012)), or lenalidomide and low-dose dexamethasone (Lonial et al., J. Clin. Oncol., 30:1953-1959 (2012); and Richardson et al., Blood (ASH Annual Meeting Abstracts) 116:986 (2010) for the treatment of patients with relapsed or refractory multiple myeloma, have been reported. All three combinations showed a manageable safety profile and encouraging activity. For example, a Phase I/II study evaluating the safety and efficacy of elotuzumab in combination lenalidomide and low-dose dexamethasone for the treatment of relapsed or refractory multiple myeloma demonstrated a 33 month PFS as well as a 92% response rate for patients receiving the 10 mg/kg dose (Lonial et al., J. Clin. Oncol., 31 (2013) (Suppl., Abstr. 8542)). Phase III clinical trials of lenalidomide/ dexamethasone with or without elotuzumab in previously untreated multiple myeloma patients is ongoing, while another phase III trial designed to evaluate this same combination in the first line setting is also ongoing.

In certain aspects, a therapeutically effective amount of the anti-SLAMF7 antibody, e.g., elotuzumab, is administered as a combination therapy with a therapeutically effective amount of an additional therapeutic agent. In some aspects, the anti-SLAMF7 antibody, e.g., elotuzumab, is administered concurrently with the additional therapeutic agent. In some aspects, the anti-SLAMF7 antibody, e.g., elotuzumab, is administered prior to the additional therapeutic agent. In some aspects, the anti-SLAMF7 antibody, e.g., elotuzumab, is administered after the additional therapeutic agent. In some aspects, the therapeutic agent is an anticancer agent. In some aspects, the additional therapeutic agent is selected from bortezomib, lenalidomide, pomalidomide, dexamethasone, or any combination thereof. In some aspects, the additional therapeutic agent is selected from bortezomib, lenalidomide, pomalidomide, dexamethasone, or any combination thereof. In some aspects, a therapeutically effective amount of the anti-SLAMF7 antibody is administered in combination with a therapeutically effective amount of bortezomib. In some aspects, a therapeutically effective amount of the anti-SLAMF7 antibody is administered in combination with a therapeutically effective amount of lenalidomide. In some aspects, a therapeutically effective amount of the anti-SLAMF7 antibody is administered in combination with a therapeutically effective amount of dexamethasone. In some aspects, a therapeutically effective amount of the anti-SLAMF7 antibody is administered in combination with a therapeutically effective amount of bortezomib and a therapeutically effective amount of lenalidomide. In some aspects, a therapeutically effective amount of the anti-SLAMF7 antibody is administered in combination with a therapeutically effective amount of bortezomib and a therapeutically effective amount of dexamethasone. In some aspects, a therapeutically effective amount of the anti-SLAMF7 antibody is administered in combination with a therapeutically effective amount of lenalidomide and a therapeutically effective amount of dexamethasone. In some aspects, a therapeutically effective amount of the anti-SLAMF7 antibody is administered in combination with a therapeutically effective amount of bortezomib, a therapeutically effective amount of lenalidomide, and a therapeutically effective amount of dexamethasone.

In some aspects, a therapeutically effective amount of the anti-SLAMF7 antibody is administered in combination with a therapeutically effective amount of diphenhydramine. In some aspects, a therapeutically effective amount of the anti-SLAMF7 antibody is administered in combination with a therapeutically effective amount of ranitidine. In some aspects, a therapeutically effective amount of the anti-SLAMF7 antibody is administered in combination with a therapeutically effective amount of acetaminophen.

In some aspects, a therapeutically effective amount of the anti-SLAMF7 antibody is administered in combination with a therapeutically effective amount of an agonistic CD137 antibody (see US 2016/0264670 A1, which is incorporated by reference herein in its entirety). In some aspects, a therapeutically effective amount of the anti-SLAMF7 antibody is administered in combination with a therapeutically effective amount of urelumab.

The anti-SLAMF7 antibody can be administered by any route. In some aspects, the anti-SLAMF7 antibody is administered intravenously, subcutaneously, intradermally, intraperitoneally, intramuscularly, or any combination thereof. In certain aspects, the anti-SLAMF7 antibody is administered intravenously.

In some aspects, an anti-SLAMF7 antibody is administered to a subject having M-proteins as determined using any method disclosed herein. In some aspects, the subject is administered an anti-SLAMF7 antibody if the M-proteins are above a threshold level of M-proteins. In some aspects, the threshold level of M-proteins is at least about 1 g/L, at least about 2 g/L, at least about 3 g/L, at least about 4 g/L, at least about 5 g/L, at least about 10 g/L, at least about 15 g/L, at least about 20 g/L, at least about 25 g/L, at least about 30 g/L, at least about 35 g/L, at least about 40 g/L, at least about 45 g/L, at least about 50 g/L of M-protein in a serum sample obtained from the subject. In certain aspects, the threshold level of M-proteins is about 30 g/L of M-protein in a serum sample obtained from the subject.

In some aspects, the threshold level indicated that the subject has a certain type of plasma cell disorder. In some aspects, if a serum sample obtained from the subject is determined to have (as measured using any method disclosed herein) at least about 30 g/L of M-protein, the subject is identified as having an MM. In some aspects, the method further comprises administering an anti-SLAMF7 antibody to the subject identified as having an MM. In some aspects, the method further comprises obtaining a bone marrow biopsy from the subject identified as having an MM.

In some aspects, if a serum sample obtained from the subject is determined to have (as measured using any method disclosed herein) at least about 1 g/L to at least about 30 g/L of M-protein, the subject is identified as a candidate at risk of having an MM. In some aspects, if a serum sample obtained from the subject is determined to have (as measured using any method disclosed herein) at least about 5 g/L to at least about 30 g/L of M-protein, the subject is identified as a candidate at risk of having an MM. In some aspects, if a serum sample obtained from the subject is determined to have (as measured using any method disclosed herein) at least about 10 g/L to at least about 30 g/L of M-protein, the subject is identified as a candidate at risk of having an MM. In some aspects, the method further comprises obtaining a bone marrow biopsy from the subject identified as candidate at risk of having an MM. In certain aspects, the bone marrow biopsy is further analyzed for markers of MM.

All of the references cited above, as well as all references cited herein, are incorporated herein by reference in their entireties.

The following examples are offered by way of illustration and not by way of limitation.

EXAMPLES

The present example describes an immunocapture (IC) liquid chromatography (LC) mass spectrometry (MS) assay, which uses a fully automated immunocapture step, analytical flow chromatography, and a simplified data extraction procedure to detect M-protein. The IC-LC-MS assay eliminates interference from therapeutic monoclonal antibodies when detecting M-proteins.

Materials and Methods

1. Materials

Purified immunoglobulin subtypes from human myeloma plasma, buffered tris(2-carboxyethyl)phosphine hydrochloride (TCEP) solution, zwittergent 3-12, hydrochloric acid, HPLC-grade acetonitrile and 2-propanol were purchased from Sigma-Aldrich (MO, USA). Monoclonal therapeutic antibodies were obtained from Bristol-Myers Squibb Research and Development. Formic acid (SupraPur grade) was purchased from EMD Chemicals (NJ, USA). ESI-Dulbecco's phosphate-buffered saline was obtained from Lonza Walkersville, Inc. (MD, USA). PhyTip columns containing 1:1 mixture of CaptureSelect LC-lambda (Hu) and CaptureSelect Kappa XL resin were custom-made by PhyNexus (CA, USA). Human sera were purchased by Bioreclamation IVT (NY, USA).

2. Serum Samples

A human serum pool with normal polyclonal background was prepared by combining four normal human serum pools. Serial dilutions of multiple myeloma samples were prepared from sera with a previously quantified M-protein concentration ($\geq 5000.0$ µg/mL and $\leq 35.0$ µg/mL). A total of fifty multiple myeloma serum samples were selected: thirty samples contained IgG(kappa); thirteen samples contained IgG(lambda); and seven samples contained IgA, four with kappa light chain, and three with lambda light chain. For each selected M-protein, sera were diluted to 1000.0 µg/mL of M-protein by mixing with a normal serum pool, followed by serial dilutions of the 1000.0 µg/mL sample to the analyte concentrations of 500.0, 250.0, 100.0, 50.0, 25.0, and 10.0 µg/mL.

3. Standards and Quality Control Samples

Elotuzumab is a humanized IgG1 monoclonal antibody for the treatment of multiple myeloma. It is a good surrogate analyte to mimic endogenous monoclonal antibodies, because it is pure, stable, and available in large quantities. The stock solution of Elotuzumab was prepared by adding pooled human serum to a drug vial containing lyophilized mAb to a final concentration of 25 mg/mL. Lots of pooled human serum were screened and those which did not contain any M-spike were pooled for quality control (QC) preparation. Elotuzumab and QC samples were prepared from the stock solution by serial dilution with the pooled blank human serum.

4. Sample Preparation

Serum samples, standards, and QCs were diluted 40-fold with PBS and 110 µL of diluted sample was used for the immunocapture. Custom made PhyTip columns containing a 1:1 mixture of CaptureSelect LC-lambda (Hu) and CaptureSelect Kappa XL resin were used for immunocapture of immunoglobulins. These PhyTip columns were used on the Freedom EVO® automation platform, equipped with 96 channels (TECAN, USA). The automated immunocapture process included the following steps: 1) four cycles of washing tips with PBS; 2) thirty-two cycles of capturing immunoglobulins from diluted sera; 3) a total of 8 cycles of washing the tips with wash buffer I (10 mM phosphate, 500 mM NaCl and 0.1% zwittergent, pH 7.4), PBS, and water; 4) 10 cycles of elution with 12 mM HCl containing 100 mM NaCl. The eluted samples were reduced immediately by adding 100 mM buffered TCEP solution to the final concentration of 20 mM followed by incubation at 25° C. for 30 min.

5. LC-MS

Chromatography was performed on Acquity UPLC H-class Bio system (Waters Corporation, MA). Samples were injected onto a C4 column (Acquity Protein BEH C4 300 Å, 1.7 µm, 2.1 mm×100 mm; Waters Corporation, MA) with the column temperature set to 80° C. Mobile phase A contained 0.1% formic acid (FA) in water and mobile phase B contained 0.1% FA in acetonitrile. A gradient separation program was used as following: 0-1.0 min 10% B; 1.1-3.0 min 10-33% B 3.0-10.0 min 33-40% B; 10.1-10.5 min 40-90% B; 10.5-13.0 min hold at 90% B; 13.0-15.0 min 90-100% B; and run stopped at 15.0 min. The flow rate was set at 0.3 mL/min and the injection volume was 2.0 µL.

The UPLC was done on-line with a Maxis 4G Q-TOF instrument with a standard Electrospray (ESI) Apollo-source (Bruker Daltonics, Hamburg, Germany). To ensure mass accuracy, the instrument was calibrated before each run by infusing ESI-L low concentration tuning mix (Agilent Technologies, CA). Each 15-min run was segmented as follows: 3 min to waste, followed by 7 min to source, and the last 5 min to waste. Capillary voltage was set at 4500 V. The nebulizer was set at 1.6 bar. The dry gas was set at 8.5 L/min. The dry temperature was set at 200° C. The transfer funnel RF and multipole RF parameters were set at 400 Vpp; no isCID energy was applied. The ion cooler transfer time was 100 µs, with a prepulse storage of 25 µs. The ion polarity was positive, the rolling average was activated and set at 2. TOF MS scans were acquired from m/z 700-2700 with an acquisition rate of 1.0 Hz.

6. MS Data Analysis

MS data files were processed using Compass DataAnalysis 4.3 software. Details of the method are as follows: analyte retention time (RT) was set to 5.6-6.8 min as all tested immunoglobulins were co-eluting in this retention window. MS peak spectrum extraction window was within 800 and 2400 m/z; smoothing and baseline subtraction for the mass spectra was disabled, and the maximum entropy deconvolution range was from 20,000 to 28,000 Da. Integration of deconvoluted spectra was analogous to integration of chromatographic peaks. Tian et al., 8 *Bioanalysis* 1679-1691 (2016). Peak finding parameters were adjusted as described above and peak heights of the analyte were calculated. Light chain molecular masses and spectral peak heights were exported to mgf files. Subsequent detection of monoclonal light chains (LCs) was performed by searching for the presence of a peak above the polyclonal background with a molecular mass within ±1.0 Da of pretreatment monoclonal LC. The light chain peak height was recorded as counts. The peak height of the LC in the polyclonal background adjacent to the analyte of interest was also recorded. In order to subtract the background and account for differences in polyclonal backgrounds, the peak height of the adjacent light chain was subtracted from the peak height of the analyte. For non-quantitative measurement of light chains the mass spectra was extracted using exact individual light chain retention time.

7. Serum Protein Electrophoresis

SPEP and SIFE analysis was performed on the Helena labs gel electrophoresis system (Helena laboratories, TX) following manufacturer's instructions. Negative SIFE was defined as the absence of distinct bands on the electrophoresis gel.

Results and Discussion

1. IC-LC-MS Assay Workflow

Figure 1:
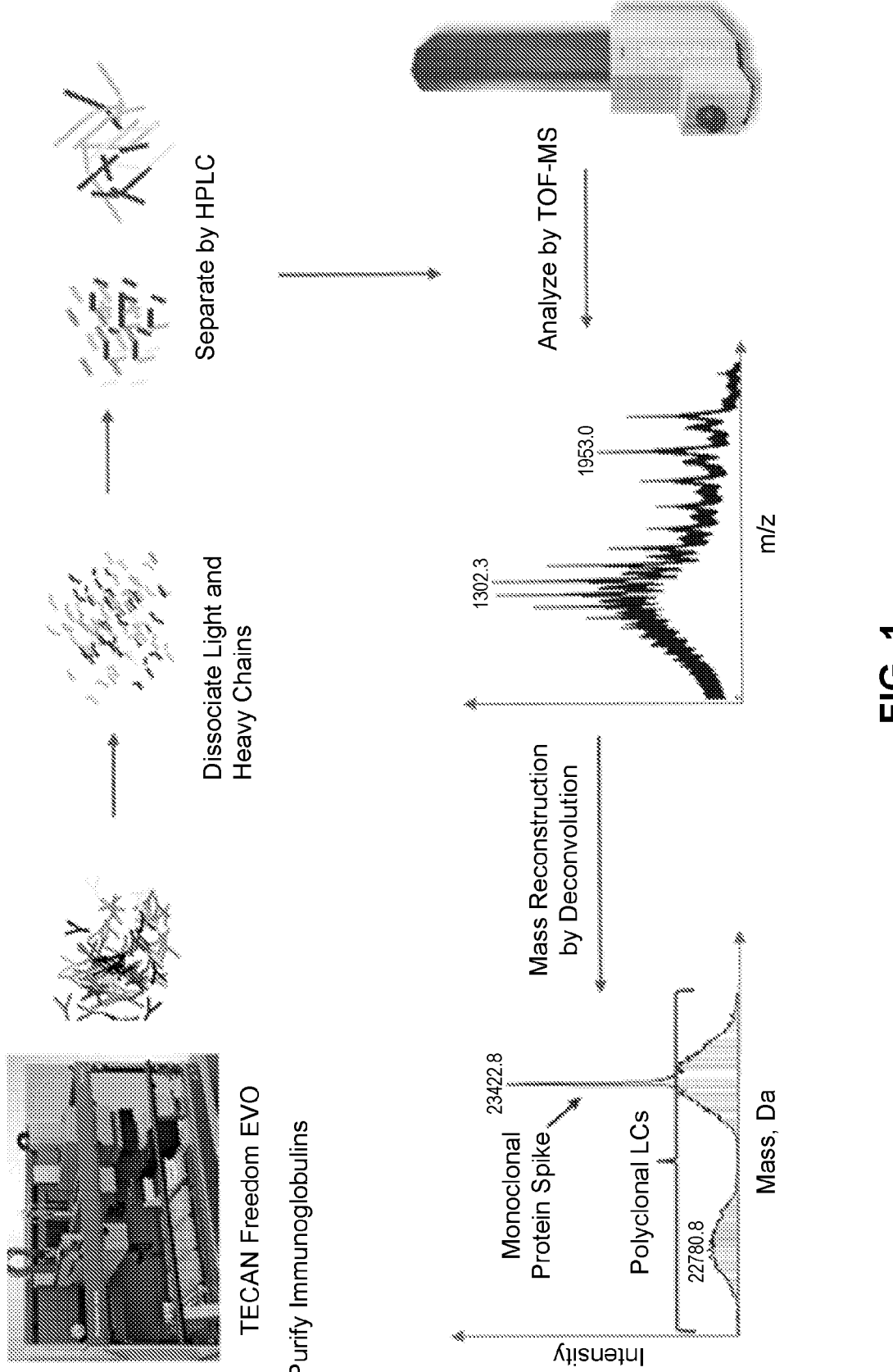
FIG. 1 is a flow chart illustrating the immunocapture (IC) liquid chromatography (LC) mass spectrometry (MS) methodology for measuring M-protein in a biological sample obtained from a human.

The described IC-LC-MS assay uses a fully automated immunocapture step and a simplified data extraction procedure. Immunoglobulins and free light chains are purified from serum using Phynexus tips filled with an anti-kappa/ anti-lambda resin mixture on TECAN Freedom EVO® robotic platform. After a purification step, intact antibodies are reduced and light chains are analyzed by LC-MS. The intensity of the deconvoluted peak height of M-protein is conveniently used to quantitate the analyte. A summary of the assay workflow is provided in FIG. 1.

2. LC-MS and Data Analysis

The liquid chromatography step was used to desalt and separate the light chains from co-purifying proteins; however, each of the individual light chain analytes was not separated. The defined chromatogram profile was 72 sec wide: all human immunoglobulins light chains tested were eluting in this retention window. The intensity of the deconvoluted spectral peak height of each M-protein was used for the measurement of the relative quantity of the analyte. FIGS. 2A-2I show simplified chromatograms, mass spectra, and deconvoluted/reconstructed spectra for immunoglobulins purified from normal human serum (FIGS. 2A-2C), multiple myeloma patient 01 (FIGS. 2D-2F), and multiple myeloma patient 02 (FIGS. 2G-2I) sera. Total ion chromatograms (TIC) represent a broad 1.2 min elution peak of reduced immunoglobulins (FIGS. 2A, 2D, and 2G. Mass spectra extracted from normal serum (FIG. 2A) show a wide range of unresolved peaks; while mass spectra extracted from multiple myeloma serum immunoglobulins (FIGS. 2E and 2H) represent well-defined multiple charged ions. Deconvoluted mass spectra of normal human immunoglobulins (FIG. 2C) have multiple low intensity peaks with no peaks above the polyclonal background. Whereas deconvolution of mass spectra of multiple myeloma immunoglobulins yields a single high intensity peak representing disease-associated light chain for each patient (FIGS. 2F and 2I). The masses of disease associated light chains are distinct and represent different immunoglobulins overproduced by malignant plasma cells by each individual. Mass spectra of leaching lambda/kappa nanobodies used for immunoglobulin purification are indicated with asterisks.

In current bioanalytical practice, multiply charged ions are summed to quantify intact proteins. These ions are processed to generate extracted ion chromatograms (XICs) for quantitation. Yet, the approach of selecting individual m/z ions for each patient's M-protein is not practical. In addition, the signal intensity is significantly diluted among extensively charged ions and the resolution of the analyte ions from potential interferences becomes very challenging. For the reasons described above, the deconvoluted light chain peak height was used for quantitation. The "deconvoluted peak height" approach was shown to be more robust and yield a better sensitivity than the use of multiple charged ions to generate XICs for quantitation.

3. Immunoglobulin Purification

To improve the analytical sensitivity of the method, immunoglobulins need to be purified from serum samples. Due to the diversity of the analyte, generic capture reagents that bind with a good affinity to all human immunoglobulins were needed. There are several routine methods available for antibody purification; however, most of them will bind only specific classes of immunoglobulins. Multiple myeloma M-proteins can be associated with any of the heavy or light chain immunoglobulin classes. Therefore, capture reagents that would bind all the antibody classes as well as free light chains were sought to develop a simple and robust assay. After careful technical considerations and initial experiments, anti-lambda/anti-kappa capture resins mixed in a 1:1 ratio were selected. The best performing affinity matrix for this application was CaptureSelect® nanobody resin available from ThermoFisher. This resin was packed into Phy- Tips™, which are completely amenable to automation. The selected PhyTips™ had capacity for loading of 40 μg of lambda and 40 μg of kappa immunoglobulins. To prevent over-saturation of the tips and to capture all endogenous immunoglobulins, serum samples were diluted forty-fold. The immunocapture procedure was tested using endogenous IgG, IgA, and IgM as well as therapeutic monoclonal antibodies: nine endogenous M-proteins purchased from Sigma, and eight therapeutic monoclonal antibodies were used to evaluate immunocapture recoveries. Immunocapture recoveries were evaluated by comparing the MS response (peak height) of the analyte purified from human serum with the peak height of the corresponding analyte that was post-spiked into polyclonal background purified from normal human serum without a spike. As shown in FIG. 3, quantitative recoveries for all the antibodies tested were consistently higher than 80.0%.

IC-LC-MS Assay Evaluation

1. Impact of the Analyte Heterogeneity on Signal Intensity

One of the major concerns for the heterogeneous analytes is that the MS response will vary greatly and be dependent on the nature of, and not solely the concentration of, the analyte. To explore if differences in ionization between the different light chains is significant, five non-identical IgG kappa therapeutic antibodies spiked into normal serum at concentrations of 10.0; 25.0; 50.0; 100.0; 250.0; 500.0, and 1000.0 μg/mL were tested to generate standard deconvoluted curves. The assay LLOQ for all the antibodies tested was 25.0 μg/mL and the LOD was 10.0 μg/mL. MS responses varied from 20-30% between the different analytes. This is an acceptable variation considering that biomarker concentrations are usually relative, since an analyte and a calibrator are rarely identical. Deconvoluted light chain standard curves for five non-identical therapeutic mAbs are shown in FIG. 4.

2. IC-LC-MS Assay Sensitivity

To test the sensitivity of the IC-LC-MS assay, three individual monoclonal antibodies (A, B, and C) were spiked into normal human serums and tested by immunocapture IC-LC-HRMS methodology (FIGS. 5A-5I). Each antibody was tested at concentrations of 1000 μg/mL (FIGS. 5A, 5D, and 5G), 100 μg/mL (FIGS. 5B, 5E, and 5H), and 10 μg/mL (FIGS. 5C, 5D, and 5I). To detect analytes at 10 μg/mL, mass spectra were extracted from a 0.2 min chromatographic window specific for the analyte of interest. The molecular masses of the antibodies tested matched their original peak masses within ±1.0 Da at all the concentrations tested. All three peaks had low signal to noise ratio, but could be detected with high confidence due to exact mass. Based on this data, an estimated limit of detection LOD of the immunocapture IC-LC-MS methodology is 100-fold lower than that of the clinical SPEP assay which has sensitivity of 1000 μg/mL. In order to achieve maximum sensitivity, the mass spectra were extracted using exact individual light chain retention time as described above.

Figures 5J, 5K, 5L, 5M:
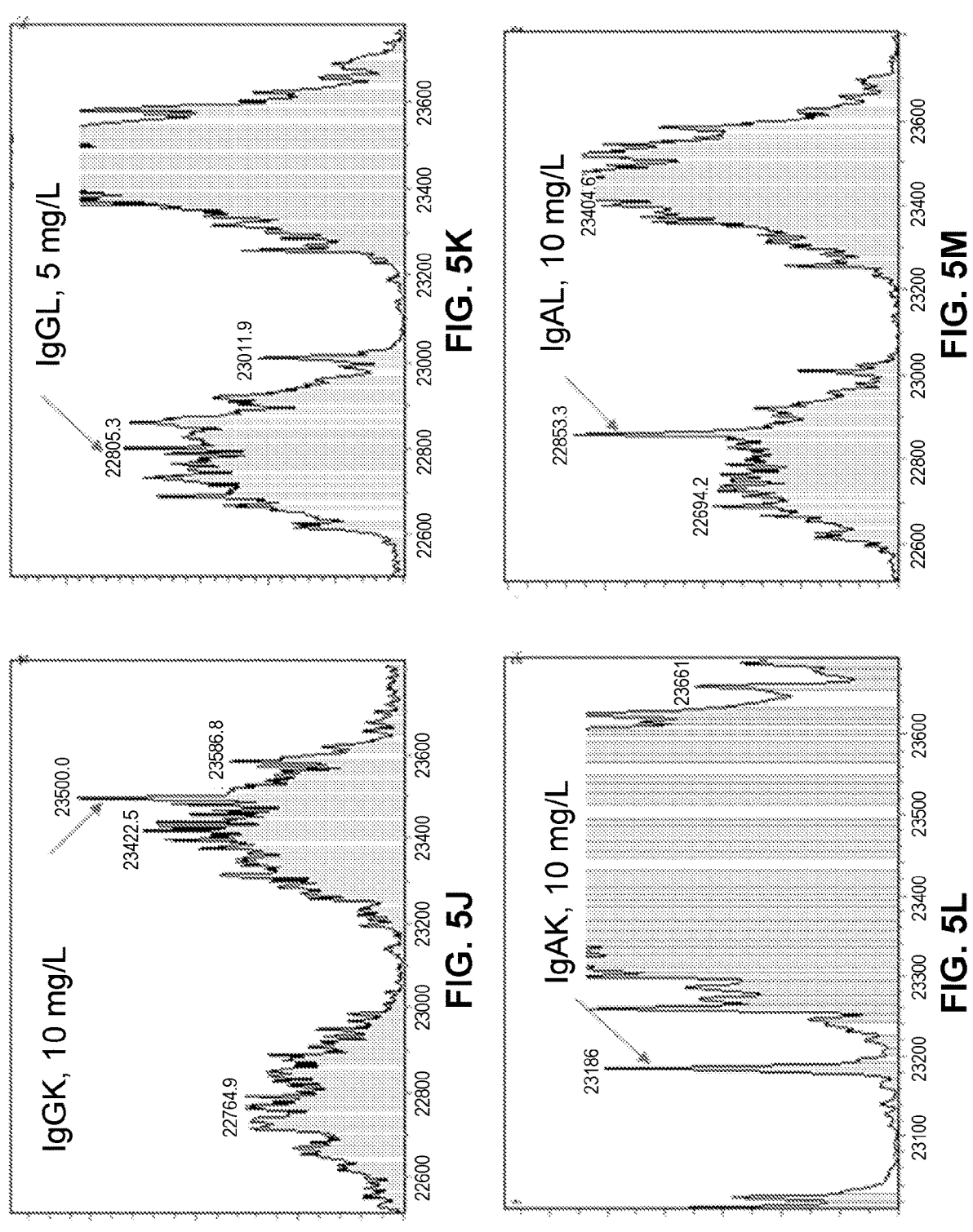

To test the limits of detection for the IC-LC-MS assay, health serum was spiked with different M proteins (FIGS. 5J-5M; Table 1). Peaks corresponding to IgGK (10 mg/L; FIG. 5J), IgGL (5 mg/L; FIG. 5K), IgAK (10 mg/L; FIG. 5L), and IgAL (10 mg/L; FIG. 5M) are indicated by an arrow in FIGS. 5J-5M.

TABLE 1

| IC-LC-MS Assay - Limit of Detection Analysis | | |
| --- | --- | --- |
| M-protein | Mass, Da | LOD μg/mL (=mg/L) |
| IgGK (1) | 23,500.7 | 10.0 |
| IgGK (2) | 23,996.8 | 5.0 |
| IgGL(1) | 22,805.0 | 5.0 |
| IgGL (2) | 22,793.5 | 5.0 |
| IgAK | 23,185.0 | 10.0 |
| IgAL | 22,863.8 | 10.0 |

3. Direct Comparison of SIFE and IC-LC-MS Assay Sensitivities

In order to compare LC-MS and SIFE assay sensitivities, fifty multiple myeloma sera were serially diluted to theoretical M-protein concentrations of 1000.0 to 50.0 μg/mL. All diluted samples were split into two and analyzed by both SIFE and IC-LC-MS. The SIFE LOD was calculated based on the concentration of the original sample and the dilution factor. And was determined as the last original sample dilution giving a distinct band on SIFE gel. As expected, SIFE sensitivity varied greatly depending on the analyte and was found to be between 250.0-1000.0 μg/mL. Sensitivity that is slightly lower than the literature reported SIFE sensitivity can be explained by the fact that all multiple myeloma sera were diluted in a normal human serum pool, which has higher polyclonal immunoglobulin concentrations than multiple myeloma serum. High polyclonal background naturally interferes with the analyst ability to see a distinct band on the heavily stained gel. A plot representing the distribution of the MS responses measured by IC-LC-method at the lowest serial dilution concentration measurable by SIFE is shown in FIG. 6. The estimated IC-LC-MS method LOD is 10-100-fold lower than SIFE LOD.

4. Addressing Therapeutic Antibody Interference

To show that the IC-LC-MS assay readily differentiates between endogenous antibodies and therapeutic antibodies, fifty multiple myeloma sera with endogenous monoclonal antibody concentrations were spiked with 200.0 μg/mL of Elotuzumab, the concentration equivalent to the pharmacokinetic $EC_{50}$ of this biological drug. In forty-nine cases endogenous antibody could be differentiated from Elotuzumab. Representative mass peaks of Elotuzumab and M-proteins are shown in FIGS. 7A-7N. FIG. 7E shows an M-protein control containing no Elotuzumab. The molecular mass of the M-protein light chain was accurately identified in all but one case. It was determined that one of the serums had Elotuzumab interference because the endogenous monoclonal antibody molecular weight was less than 2.0 Da apart from the Elotuzumab mass peak. An M-protein mass peak shift by more than 1.0 Da in the presence of the Elotuzumab peak demonstrated that this was a real interference case (data not shown).

5. IC-LC-MS Assay can Sensitively Monitor Myeloma Disease and Detect Increases in M-Protein Earlier than Standard Methods We investigated whether the IC-LC-MS assay could provide more accurate information on multiple myeloma disease monitoring when compared with standard SPEP/SIFE/sFLC tests. To determine at which cycle sustained increases in M-protein start for each subject, IC-LC-MS measurements in $\log_{10}$ scale and visually identified unambiguous inflexion points were inspected. For myeloma patients with very good partial response (VGPR) and complete response (CR) IC-LC-MS was more sensitive: M-protein was detectable at all the time points measured by the novel assay, disclosed herein. However, SPEP/SIFE were negative in cycles 5-29 for patient 1 (FIGS. 8A-8B) and cycles 8-28 for patient 2 (FIGS. 8E-8F). The IC-LC-MS assay could detect sustained increase in M-protein much earlier than both SPEP/SIFE. For patient 1 sustained increase was detected in cycle 20, or 10 cycles earlier than by SPEP (compare FIG. 8C to FIG. 8A). For patient 2 sustained increase was detected in cycle 16, or 13 cycles earlier than by SPEP (compare FIG. 8G to FIG. 8E).

FIGS. 9A-9F show IC-LC-MS profiles for selected time points in the subject, where M-protein was detected by IC-LC-MS peak analysis algorithm at all time-points due to superior specificity of the assay. The M-protein light chain mass signatures can be easily identified in the baseline sample and then followed in the sequential samples. This approach allows very specific tracking of the M-protein above the polyclonal background.

All publications, patents, and patent applications disclosed herein are incorporated by reference to the same extent as if each individual publication, patent or patent application was specifically and individually indicated to be incorporated by reference.

What is claimed is:

1. A method of measuring M-protein in a biological sample obtained from a subject having a plasma cell disorder, wherein the M-protein is measured by:
   (1) purifying immunoglobulins and free light chains in the biological sample by immunocapture,
   (2) dissociating the purified immunoglobulins, and
   (3) applying the dissociated purified immunoglobulins and free light chains to a liquid chromatography-mass spectrometer (LC-MS);
   wherein the biological sample is a blood sample or urine sample;
   wherein the liquid chromatography (LC) employs (i) a mobile phase A, comprising water with 0.1% formic acid, and (ii) a mobile phase B, comprising 0.1% formic acid in acetonitrile; and
   wherein the mass spectrometer (MS) employs a capillary voltage of about 4000 V to about 6000 V.

2. The method of claim 1, wherein the biological sample is a urine sample or a serum sample.

3. The method of claim 1, wherein the subject received a previous therapy to treat a plasma cell disorder.

4. The method of claim 1, wherein the M-protein comprises:
   (i) an IgG, an IgA, and IgM, an IgD, a fragment thereof, or any combination thereof;
   (ii) a kappa isotype or a lambda isotype;
   (iii) one or more free light chain; or
   (iv) any combination of (i) to (iii).

5. The method of claim 1, wherein the MS comprises:
   (i) an electrospray (ESI) time-of-flight (TOF) MS;
   (ii) a laser desorption ionization (MALDI) TOF;
   (iii) a MALDI TOF MS; or
   (iv) any combination of (i) to (iii).

6. The method of claim 1, wherein the immunocapture is an automated immunocapture.

7. The method of claim 1, wherein the purified immunoglobulins are dissociated by chemical reduction.

8. The method of claim 1, wherein:
   (i) the LC is an ultra-performance (UC) LC, or
   (ii) The LC is on-line with the MS.

9. The method of claim 1, wherein the plasma cell disorder comprises multiple myeloma.

10. The method of claim 9, wherein the multiple myeloma comprises:

(i) a light chain multiple myeloma, (ii) a plasma cell leukemia, or (iii) both (i) and (ii).

11. The method of claim 10, wherein the plasma cell leukemia comprises a primary plasma cell leukemia or a secondary plasma cell leukemia.

\* \* \* \* \*